(12) United States Patent
Hormann et al.

(10) Patent No.: US 7,304,162 B2
(45) Date of Patent: Dec. 4, 2007

(54) OXADIAZOLINE LIGANDS FOR MODULATING THE EXPRESSION OF EXOGENOUS GENES VIA AN ECDYSONE RECEPTOR COMPLEX

(75) Inventors: Robert Eugene Hormann, Melrose Park, PA (US); Orestes Chortyk, Thompson Station, TN (US); Dat Phat Le, North Wales, PA (US)

(73) Assignee: Intrexon Corporation, Blacksburg, VA (US)

( * ) Notice: Subject to any disclaimer, the term of this patent is extended or adjusted under 35 U.S.C. 154(b) by 526 days.

(21) Appl. No.: 10/783,810

(22) Filed: Feb. 19, 2004

(65) Prior Publication Data

US 2004/0171651 A1    Sep. 2, 2004

Related U.S. Application Data

(60) Provisional application No. 60/449,467, filed on Feb. 21, 2003.

(51) Int. Cl.
*A61K 31/4245*   (2006.01)
*C07D 271/07*    (2006.01)
*A61K 31/433*    (2006.01)
*C07D 285/08*    (2006.01)

(52) U.S. Cl. ............... 548/133; 514/361; 514/364; 514/128

(58) Field of Classification Search ........... 548/133
See application file for complete search history.

(56) References Cited

U.S. PATENT DOCUMENTS

| | | | |
|---|---|---|---|
| 4,814,349 A | 3/1989 | Addor et al. | |
| 4,906,280 A | 3/1990 | Sandler et al. | |
| 4,950,666 A | 8/1990 | Peake et al. | |
| 4,954,655 A | 9/1990 | Kelly | |
| 4,981,784 A | 1/1991 | Evans et al. | |
| 4,985,461 A | 1/1991 | Hsu et al. | |
| 5,075,471 A | 12/1991 | Michelotti et al. | |
| 5,283,173 A | 2/1994 | Fields et al. | |
| 5,358,966 A | 10/1994 | James, Jr. et al. | |
| 5,424,333 A | 6/1995 | Wing | |
| 5,482,962 A | 1/1996 | Hormann | |
| 5,530,028 A | 6/1996 | Lidert et al. | |
| 5,880,333 A | 3/1999 | Goff et al. | |
| 6,013,836 A | 1/2000 | Hsu et al. | |
| 6,147,282 A | 11/2000 | Goff et al. | |
| 6,245,531 B1 | 6/2001 | Hogness et al. | |
| 6,258,603 B1 | 7/2001 | Carlson et al. | |
| 6,265,173 B1 | 7/2001 | Evans et al. | |
| 6,300,488 B1 | 10/2001 | Gage et al. | |

OTHER PUBLICATIONS

Enders et al., Diastereo- and enantioselective synthesis of 2-1,2,4-oxadiazolines by 1,3-dipolar cycloaddition of nitrile oxides with chiral hydrazones, Heterocycles, 1999, 50(2), 995-1024.

Hussein et al. Ring transformation of heterocycles: Part 3. A conversion of 4-amino-•2-1,2,4-oxadiazolines into 2-arylamino-1,3,4-thiadiazoles and oxa-analogs. Heterocycles,1994, 38(5), 981-90.

El-Abadelah et al. Ring transformations of heterocycles. Part 1. Transformation of 4-amino-•2-1,2,4-oxadiazolines into 1,3,4-oxadiazoles. Journal of Heterocyclic Chemistry, 1991, 28(5), 1229-34.

Argyropoulos et al. 1,3-Dipolar cycloaddition reactions of 1,3,4-oxadiazin-6-ones with nitrile oxides. Journal of Heterocyclic Chemistry, 1990, 27(5), 1425-32.

El-Abadelah et al. Heterocycles from nitrile oxides. Part V. 4-Amino-•2-1,2,4-oxadiazolines. Heterocycles, 1989, 29(10), 1957-64.

Gibert et al. Competition between the dipolarophilic and nucleophilic reactivities of 2-pyrazolines in the presence of benzonitrile oxide. Synthesis, identification, and the chemical behavior of tetrahydropyrazolo[4,5-b]-1,2,4-oxadiazoles. Journal of Heterocyclic Chemistry, 1979, 16(2),p. 311-320.

Gibert et al. Action of benzonitrile oxide on 2-pyrazolines. Lab. Synth. Etud. Physicochem. Heterocycles Azotes, Univ. Sci. Technol. Languedoc, Montpellier, Fr. Tetrahedron Letters, 1974, (9), 755-7.

Andrianov et al. Derivatives of 4-amino-•2-1,2,4-oxadiazoline. Inst. Org. Sint., Riga, USSR. Khimiya Geterotsiklicheskikh Soedinenii, 1991, (2), 262-4.

Andrianov et al. Acid halides of 4-aminofurazan-3-carbohydroximic acid. Inst. Org. Sint., Riga, Latvia. Khimiya Geterotsiklicheskikh Soedinenii, 1992, (5), 687-91.

*Primary Examiner*—Laura L. Stockton
(74) *Attorney, Agent, or Firm*—Sughrue Mion PLLC

(57) ABSTRACT

The present invention relates to non-steroidal ligands for use in nuclear receptor-based inducible gene expression system, and a method to modulate exogenous gene expression in which an ecdysone receptor complex comprising: a DNA binding domain; a ligand binding domain; a transactivation domain; and a ligand is contacted with a DNA construct comprising: the exogenous gene and a response element; wherein the exogenous gene is under the control of the response element and binding of the DNA binding domain to the response element in the presence of the ligand results in activation or suppression of the gene.

5 Claims, No Drawings

SEQUENCE LISTING

<160> NUMBER OF SEQ ID NOS: 11

<210> SEQ ID NO 1
<211> LENGTH: 1054
<212> TYPE: DNA
<213> ORGANISM: Choristoneura fumiferana

<400> SEQUENCE: 1

```
cctgagtgcg tagtacccga gactcagtgc gccatgaagc ggaaagagaa gaaagcacag      60
aaggagaagg acaaactgcc tgtcagcacg acgacggtgg acgaccacat gccgcccatt     120
atgcagtgtg aacctccacc tcctgaagca gcaaggattc acgaagtggt cccaaggttt     180
ctctccgaca agctgttgga gacaaaccgg cagaaaaaca tcccccagtt gacagccaac     240
cagcagttcc ttatcgccag gctcatctgg taccaggacg ggtacgagca gccttctgat     300
gaagatttga agaggattac gcagacgtgg cagcaagcgg acgatgaaaa cgaagagtct     360
gacactccct tccgccagat cacagagatg actatcctca cggtccaact tatcgtggag     420
ttcgcgaagg gattgccagg gttcgccaag atctcgcagc ctgatcaaat tacgctgctt     480
aaggcttgct caagtgaggt aatgatgctc cgagtcgcgc gacgatacga tgcggcctca     540
```

```
gacagtgttc tgttcgcgaa caaccaagcg tacactcgcg acaactaccg caaggctggc      600
atggcctacg tcatcgagga tctactgcac ttctgccggt gcatgtactc tatggcgttg      660
gacaacatcc attacgcgct gctcacggct gtcgtcatct tttctgaccg gccaggggttg     720 gagcagccgc aactggtgga agaaatccag cggtactacc tgaatacgct ccgcatctat      780
atcctgaacc agctgagcgg gtcggcgcgt tcgtccgtca tatacggcaa gatcctctca      840
atcctctctg agctacgcac gctcggcatg caaaactcca acatgtgcat ctccctcaag      900
ctcaagaaca gaaagctgcc gcctttcctc gaggagatct gggatgtggc ggacatgtcg      960
cacacccaac cgccgcctat cctcgagtcc cccacgaatc tctagcccct gcgcgcacgc     1020
atcgccgatg ccgcgtccgg ccgcgctgct ctga                                 1054

<210> SEQ ID NO 2
<211> LENGTH: 441
<212> TYPE: DNA
<213> ORGANISM: Saccharomyces cerevisiae

<400> SEQUENCE: 2
atgaagctac tgtcttctat cgaacaagca tgcgatattt gccgacttaa aaagctcaag       60
tgctccaaag aaaaaccgaa gtgcgccaag tgtctgaaga caactgggga gtgtcgctac      120
tctcccaaaa ccaaaaggtc tccgctgact agggcacatc tgacagaagt ggaatcaagg      180 ctagaaaagac tggaacagct atttctactg attttcctc gagaagacct tgacatgatt      240
ttgaaaatgg attctttaca ggatataaaa gcattgttaa caggattatt tgtacaagat      300
aatgtgaata agatgccgt cacagataga ttggcttcag tggagactga tatgcctcta      360
acattgagac agcatagaat aagtgcgaca tcatcatcgg aagagagtag taacaaaggt      420
caaagacagt tgactgtatc g                                                441

<210> SEQ ID NO 3
<211> LENGTH: 538
<212> TYPE: DNA
<213> ORGANISM: Mus musculus

<400> SEQUENCE: 3
tcgagggccc ctgcaggtca attctaccgg gtaggggagg cgcttttccc aaggcagtct       60
ggagcatgcg ctttagcagc cccgctggca cttggcgcta cacaagtggc ctctggcctc      120
gcacacattc cacatccacc ggtagcgcca accggctccg ttctttggtg gcccctccgc      180
gccaccttct actcctcccc tagtcaggaa gttcccccc gccccgcagc tcgcgtcgtg       240
caggacgtga caaatggaag tagcacgtct cactagtctc gtgcagatgg acagcaccgc      300
tgagcaatgg aagcgggtag gcctttgggg cagcggccaa tagcagcttt gctccttcgc      360
tttctgggct cagaggctgg gaaggggtgg gtccgggggc gggctcaggg gcgggctcag      420
ggcgggggcg ggcgcgaagg tcctcccgag gcccggcatt ctcgcacgct tcaaaagcgc      480
acgtctgccg cgctgttctc ctcttcctca tctccgggcc tttcgacctg cagccaat       538

<210> SEQ ID NO 4
<211> LENGTH: 720
<212> TYPE: DNA
<213> ORGANISM: Homo sapiens

<400> SEQUENCE: 4
gcccccgagg agatgcctgt ggacaggatc ctggaggcag agcttgctgt ggaacagaag       60
```

```
agtgaccagg gcgttgaggg tcctggggga accgggggta gcggcagcag cccaaatgac        120
cctgtgacta acatctgtca ggcagctgac aaacagctat tcacgcttgt tgagtgggcg        180
aagaggatcc cacactttc ctccttgcct ctggatgatc aggtcatatt gctgcgggca        240
ggctggaatg aactcctcat tgcctccttt tcacaccgat ccattgatgt tcgagatggc        300
atcctccttg ccacaggtct tcacgtgcac cgcaactcag cccattcagc aggagtagga        360
gccatctttg atcgggtgct gacagagcta gtgtccaaaa tgcgtgacat gaggatggac        420
aagacagagc ttggctgcct gagggcaatc attctgttta atccagatgc caagggcctc        480
tccaacccta gtgaggtgga ggtcctgcgg gagaaagtgt atgcatcact ggagacctac        540
tgcaaacaga gtaccctga gcagcaggga cggtttgcca agctgctgct acgtcttcct        600
gccctccggt ccattggcct taagtgtcta gagcatctgt ttttcttcaa gctcattggt        660
gacaccccca tcgacacctt cctcatggag atgcttgagg ctccccatca actggcctga        720
```

<210> SEQ ID NO 5
<211> LENGTH: 635
<212> TYPE: DNA
<213> ORGANISM: Locusta migratoria

<400> SEQUENCE: 5

```
tgcatacaga catgcctgtt gaacgcatac ttgaagctga aaaacgagtg gagtgcaaag         60
cagaaaacca agtggaatat gagctggtgg agtgggctaa acacatcccg cacttcacat        120
ccctacctct ggaggaccag gttctcctcc tcagagcagg ttggaatgaa ctgctaattg        180
cagcattttc acatcgatct gtagatgtta agatggcat agtacttgcc actggtctca        240
cagtgcatcg aaattctgcc catcaagctg gagtcggcac aatatttgac agagttttga        300
cagaactggt agcaaagatg agagaaatga aaatggataa aactgaactt ggctgcttgc        360
gatctgttat tcttttcaat ccagaggtga ggggtttgaa atccgcccag gaagttgaac        420
ttctacgtga aaaagtatat gccgctttgg aagaatatac tagaacaaca catcccgatg        480
aaccaggaag atttgcaaaa cttttgcttc gtctgccttc tttacgttcc ataggcctta        540
agtgtttgga gcatttgttt ttcttttcgcc ttattggaga tgttccaatt gatacgttcc        600
tgatggagat gcttgaatca ccttctgatt cataa                                   635
```

<210> SEQ ID NO 6
<211> LENGTH: 271
<212> TYPE: DNA
<213> ORGANISM: herpes simplex virus 7

<400> SEQUENCE: 6

```
atgggcccta aaaagaagcg taaagtcgcc cccccgaccg atgtcagcct gggggacgag         60
ctccacttag acggcgagga cgtggcgatg gcgcatgccg acgcgctaga cgatttcgat        120
ctggacatgt tggggacgg ggattccccg gggccggat ttacccccca cgactccgcc         180
ccctacggcg ctctggatat ggccgacttc gagtttgagc agatgtttac cgatgccctt        240
ggaattgacg agtacggtgg ggaattcccg g                                       271
```

<210> SEQ ID NO 7
<211> LENGTH: 1167
<212> TYPE: DNA
<213> ORGANISM: Homo sapiens

<400> SEQUENCE: 7

```
tgaggctccg gtgcccgtca gtgggcagag cgcacatcgc ccacagtccc cgagaagttg         60
```

```
ggggagggg tcggcaattg aaccggtgcc tagagaaggt ggcgcggggt aaactgggaa      120
agtgatgtcg tgtactggct ccgcctttt cccgagggtg ggggagaacc gtatataagt      180
gcagtagtcg ccgtgaacgt tcttttcgc aacgggtttg ccgccagaac acaggtaagt     240
gccgtgtgtg gttcccgcgg gcctggcctc tttacgggtt atgcccttg cgtgccttga      300 attacttcca cctggctcca gtacgtgatt cttgatcccg agctggagcc aggggcgggc     360
cttgcgcttt aggagcccct tcgcctcgtg cttgagttga ggcctggcct gggcgctggg      420
gccgccgcgt gcgaatctgg tggcaccttc gcgcctgtct cgctgctttc gataagtctc     480
tagccattta aaattttga tgacctgctg cgacgctttt tttctggcaa gatagtcttg      540
taaatgcggg ccaggatctg cacactggta tttcggtttt tgggcccgcg gccggcgacg     600
gggcccgtgc gtcccagcgc acatgttcgg cgaggcgggg cctgcgagcg cggccaccga    660
gaatcggacg ggggtagtct caagctggcc ggcctgctct ggtgcctggc ctcgcgccgc    720
cgtgtatcgc cccgccctgg gcggcaaggc tggcccggtc ggcaccagtt gcgtgagcgg    780
aaagatggcc gcttcccggc cctgctccag ggggctcaaa atggaggacg cggcgctcgg    840
gagagcgggc gggtgagtca cccacacaaa ggaaaagggc ctttccgtcc tcagccgtcg   900
cttcatgtga ctccacggag taccgggcgc cgtccaggca cctcgattag ttctggagct    960
tttggagtac gtcgtctta ggttgggggg aggggtttta tgcgatggag tttccccaca     1020
ctgagtgggt ggagactgaa gttaggccag cttggcactt gatgtaattc tcgttggaat    1080
ttgccctttt tgagtttgga tcttggttca ttctcaagcc tcagacagtg gttcaaagtt    1140
tttttcttcc atttcaggtg tcgtgaa                                        1167
```

<210> SEQ ID NO 8
<211> LENGTH: 19
<212> TYPE: DNA
<213> ORGANISM: Artificial sequence
<220> FEATURE:
<223> OTHER INFORMATION: GAL4 response element

<400> SEQUENCE: 8

```
ggagtactgt cctccgagc                                                   19
```

<210> SEQ ID NO 9
<211> LENGTH: 6
<212> TYPE: DNA
<213> ORGANISM: Artificial sequence
<220> FEATURE:
<223> OTHER INFORMATION: synthetic promoter

<400> SEQUENCE: 9

```
tatata                                                                  6
```

<210> SEQ ID NO 10
<211> LENGTH: 1653
<212> TYPE: DNA
<213> ORGANISM: Artificial Sequence
<220> FEATURE:
<223> OTHER INFORMATION: luciferase gene

<400> SEQUENCE: 10

```
atggaagacg ccaaaaacat aaagaaaggc ccggcgccat tctatcctct agaggatgga      60
accgctggag agcaactgca taaggctatg aagagatacg ccctggttcc tggaacaatt    120
gcttttacag atgcacatat cgaggtgaac atcacgtacg cggaatactt cgaaatgtcc    180
```

```
gttcggttgg cagaagctat gaaacgatat gggctgaata caaatcacag aatcgtcgta    240
tgcagtgaaa actctcttca attctttatg ccggtgttgg gcgcgttatt tatcggagtt    300
gcagttgcgc ccgcgaacga catttataat gaacgtgaat tgctcaacag tatgaacatt    360
tcgcagccta ccgtagtgtt tgtttccaaa aagggggttgc aaaaaatttt gaacgtgcaa    420
aaaaaattac caataatcca gaaaattatt atcatggatt ctaaaacgga ttaccaggga    480
tttcagtcga tgtacacgtt cgtcacatct catctacctc ccggttttaa tgaatacgat    540
tttgtaccag agtcctttga tcgtgacaaa acaattgcac tgataatgaa ttcctctgga    600
tctactgggt tacctaaggg tgtggccctt ccgcatagaa ctgcctgcgt cagattctcg    660
catgccagag atcctatttt tggcaatcaa atcattccgg atactgcgat tttaagtgtt    720
gttccattcc atcacggttt tggaatgttt actacactcg atatttgat atgtggattt    780 cgagtcgtct taatgtatag atttgaagaa gagctgtttt tacgatccct tcaggattac    840
aaaattcaaa gtgcgttgct agtaccaacc ctatttcat tcttcgccaa aagcactctg    900
attgacaaat acgatttatc taatttacac gaaattgctt ctgggggcgc acctctttcg    960
aaagaagtcg gggaagcggt tgcaaaacgc ttccatcttc cagggatacg acaaggatat   1020
gggctcactg agactacatc agctattctg attacacccg aggggggatga taaaccgggc   1080 gcggtcggta agttgttcc atttttttgaa gcgaaggttg tggatctgga taccgggaaa   1140
acgctgggcg ttaatcagag aggcgaatta tgtgtcagag acctatgat tatgtccggt   1200 tatgtaaaca atccggaagc gaccaacgcc ttgattgaca aggatggatg gctacattct   1260
ggagacatag cttactggga cgaagacgaa cacttcttca tagttgaccg cttgaagtct   1320
ttaattaaat acaaaggata tcaggtggcc cccgctgaat tggaatcgat attgttacaa   1380
caccccaaca tcttcgacgc gggcgtggca ggtcttcccg acgatgacgc cggtgaactt   1440
cccgccgccg ttgttgtttt ggagcacgga aagacgatga cggaaaaaga gatcgtggat   1500
tacgtcgcca gtcaagtaac aaccgcgaaa aagttgcgcg gaggagttgt gtttgtggac   1560
gaagtaccga aggtcttac cggaaaaactc gacgcaagaa aaatcagaga gatcctcata   1620
aaggccaaga agggcggaaa gtccaaattg taa                                1653
```

<210> SEQ ID NO 11
<211> LENGTH: 786
<212> TYPE: DNA
<213> ORGANISM: Mus musculus

<400> SEQUENCE: 11

```
aagcgggaag ctgtgcagga ggagcggcag cggggcaagg accggaatga gaacgaggtg     60
gagtccacca gcagtgccaa cgaggacatg cctgtagaga agattctgga agccgagctt    120
gctgtcgagc ccaagactga gacatacgtg gaggcaaaca tggggctgaa ccccagctca    180
ccaaatgacc ctgttaccaa catctgtcaa gcagcagaca agcagctctt cactcttgtg    240
gagtgggcca agaggatccc acacttttct gagctgcccc tagacgacca ggtcatcctg    300
ctacgggcag gctggaacga gctgctgatc gcctccttct cccaccgctc catagctgtg    360
aaagatggga ttctcctggc caccggcctg cacgtacacc ggaacagcgc tcacagtgct    420
ggggtgggcg ccatctttga cagggtgcta acagagctgg tgtctaagat gcgtgacatg    480
cagatggaca agacggagct gggctgcctg cgagccattg tcctgttcaa ccctgactct    540 aagggggctct caaaccctgc tgaggtggag gcgttgaggg agaaggtgta tgcgtcacta    600
gaagcgtact gcaaacacaa gtaccctgag cagccgggca ggtttgccaa gctgctgctc    660
```

```
cgcctgcctg cactgcgttc catcgggctc aagtgcctgg agcacctgtt cttcttcaag    720
ctcatcgggg acacgcccat cgacaccttc ctcatggaga tgctggaggc accacatcaa    780
gccacc                                                                786
```

US 7,304,162 B2

OXADIAZOLINE LIGANDS FOR MODULATING THE EXPRESSION OF EXOGENOUS GENES VIA AN ECDYSONE RECEPTOR COMPLEX

This application claims priority to U.S. provisional application No. 60/449,467 filed Feb. 21, 2003.

FIELD OF THE INVENTION

This invention relates to the field of biotechnology or genetic engineering. Specifically, this invention relates to the field of gene expression. More specifically, this invention relates to non-steroidal ligands for natural and mutated nuclear receptors and their use in a nuclear receptor-based inducible gene expression system and methods of modulating the expression of a gene within a host cell using these ligands and inducible gene expression system.

BACKGROUND OF THE INVENTION

Various publications are cited herein, the disclosures of which are incorporated by reference in their entireties. However, the citation of any reference herein should not be construed as an admission that such reference is available as "Prior Art" to the instant application.

In the field of genetic engineering, precise control of gene expression is a valuable tool for studying, manipulating, and controlling development and other physiological processes. Gene expression is a complex biological process involving a number of specific protein-protein interactions. In order for gene expression to be triggered, such that it produces the RNA necessary as the first step in protein synthesis, a transcriptional activator must be brought into proximity of a promoter that controls gene transcription. Typically, the transcriptional activator itself is associated with a protein that has at least one DNA binding domain that binds to DNA binding sites present in the promoter regions of genes. Thus, for gene expression to occur, a protein comprising a DNA binding domain and a transactivation domain located at an appropriate distance from the DNA binding domain must be brought into the correct position in the promoter region of the gene.

The traditional transgenic approach utilizes a cell-type specific promoter to drive the expression of a designed transgene. A DNA construct containing the transgene is first incorporated into a host genome. When triggered by a transcriptional activator, expression of the transgene occurs in a given cell type.

Another means to regulate expression of foreign genes in cells is through inducible promoters. Examples of the use of such inducible promoters include the PR1-a promoter, prokaryotic repressor-operator systems, immunosuppressive-immunophilin systems, and higher eukaryotic transcription activation systems such as steroid hormone receptor systems and are described below.

The PR1-a promoter from tobacco is induced during the systemic acquired resistance response following pathogen attack. The use of PR1-a may be limited because it often responds to endogenous materials and external factors such as pathogens, UV-B radiation, and pollutants. Gene regulation systems based on promoters induced by heat shock, interferon and heavy metals have been described (Wurn et al., 1986, Proc. Natl. Acad. Sci. USA 83:5414-5418; Arnheiter et al., 1990 Cell 62:51-61; Filmus et al., 1992 Nucleic Acids Research 20:27550-27560). However, these systems have limitations due to their effect on expression of non-target genes. These systems are also leaky.

Prokaryotic repressor-operator systems utilize bacterial repressor proteins and the unique operator DNA sequences to which they bind. Both the tetracycline ("Tet") and lactose ("Lac") repressor-operator systems from the bacterium *Escherichia coli* have been used in plants and animals to control gene expression. In the Tet system, tetracycline binds to the TetR repressor protein, resulting in a conformational change that releases the repressor protein from the operator which as a result allows transcription to occur. In the Lac system, a lac operon is activated in response to the presence of lactose, or synthetic analogs such as isopropyl-b-D-thiogalactoside. Unfortunately, the use of such systems is restricted by unstable chemistry of the ligands, i.e. tetracycline and lactose, their toxicity, their natural presence, or the relatively high levels required for induction or repression. For similar reasons, utility of such systems in animals is limited.

Immunosuppressive molecules such as FK506, rapamycin and cyclosporine A can bind to immunophilins FKBP12, cyclophilin, etc. Using this information, a general strategy has been devised to bring together any two proteins simply by placing FK506 on each of the two proteins or by placing FK506 on one and cyclosporine A on another one. A synthetic homodimer of FK506 (FK1012) or a compound resulted from fusion of FK506-cyclosporine (FKCsA) can then be used to induce dimerization of these molecules (Spencer et al., 1993, *Science* 262:1019-24; Belshaw et al., 1996 *Proc Natl Acad Sci USA* 93:4604-7). Gal4 DNA binding domain fused to FKBP12 and VP16 activator domain fused to cyclophilin, and FKCsA compound were used to show heterodimerization and activation of a reporter gene under the control of a promoter containing Gal4 binding sites. Unfortunately, this system includes immunosuppressants that can have unwanted side effects and therefore, limits its use for various mammalian gene switch applications.

Higher eukaryotic transcription activation systems such as steroid hormone receptor systems have also been employed. Steroid hormone receptors are members of the nuclear receptor superfamily and are found in vertebrate and invertebrate cells. Unfortunately, use of steroidal compounds that activate the receptors for the regulation of gene expression, particularly in plants and mammals, is limited due to their involvement in many other natural biological pathways in such organisms. In order to overcome such difficulties, an alternative system has been developed using insect ecdysone receptors (EcR).

Growth, molting, and development in insects are regulated by the ecdysone steroid hormone (molting hormone) and the juvenile hormones (Dhadialla, et al., 1998. Annu. Rev. Entomol. 43: 545-569). The molecular target for ecdysone in insects consists of at least ecdysone receptor (EcR) and ultraspiracle protein (USP). EcR is a member of the nuclear steroid receptor super family that is characterized by signature DNA and ligand binding domains, and an activation domain (Koelle et al. 1991, Cell, 67:59-77). EcR receptors are responsive to a number of steroidal compounds such as ponasterone A and muristerone A. Recently, non-steroidal compounds with ecdysteroid agonist activity have been described, including the commercially available insecticides tebufenozide and methoxyfenozide that are marketed world wide by Rohm and Haas Company (see International Patent Application No. PCT/EP96/00686 and U.S. Pat. No. 5,530,028). Both analogs have exceptional safety profiles to other organisms.

The insect ecdysone receptor (EcR) heterodimerizes with Ultraspiracle (USP), the insect homologue of the mammalian RXR, and binds ecdysteroids and ecdysone receptor response elements and activate transcription of ecdysone responsive genes. The EcR/USP/ligand complexes play important roles during insect development and reproduction. The EcR is a member of the steroid hormone receptor superfamily and has five modular domains, A/B (transactivation), C (DNA binding, heterodimerization)), D (Hinge, heterodimerization), E (ligand binding, heterodimerization and transactivation and F (transactivation) domains. Some of these domains such as A/B, C and E retain their function when they are fused to other proteins.

Tightly regulated inducible gene expression systems or "gene switches" are useful for various applications such as gene therapy, large scale production of proteins in cells, cell based high throughput screening assays, functional genomics and regulation of traits in transgenic plants and animals.

The first version of EcR-based gene switch used *Drosophila melanogaster* EcR (DmEcR) and *Mus musculus* RXR (MmRXR) and showed that these receptors in the presence of steroid, ponasteroneA, transactivate reporter genes in mammalian cell lines and transgenic mice (Christopherson K. S., Mark M. R., Baja J. V., Godowski P. J. 1992, Proc. Natl. Acad. Sci. U.S.A. 89: 6314-6318; No D., Yao T. P., Evans R. M., 1996, Proc. Natl. Acad. Sci. U.S.A. 93: 3346-3351). Later, Suhr et al. 1998, Proc. Natl. Acad. Sci. 95:7999-8004 showed that non-steroidal ecdysone agonist, tebufenozide, induced high level of transactivation of reporter genes in mammalian cells through *Bombyx mori* EcR (BmEcR) in the absence of exogenous heterodimer partner.

International Patent Applications No. PCT/US97/05330 (WO 97/38117) and PCT/US99/08381 (WO99/58155) disclose methods for modulating the expression of an exogenous gene in which a DNA construct comprising the exogenous gene and an ecdysone response element is activated by a second DNA construct comprising an ecdysone receptor that, in the presence of a ligand therefor, and optionally in the presence of a receptor capable of acting as a silent partner, binds to the ecdysone response element to induce gene expression. The ecdysone receptor of choice was isolated from *Drosophila melanogaster*. Typically, such systems require the presence of the silent partner, preferably retinoid X receptor (RXR), in order to provide optimum activation. In mammalian cells, insect ecdysone receptor (EcR) heterodimerizes with retinoid X receptor (RXR) and regulates expression of target genes in a ligand dependent manner. International Patent Application No. PCT/US98/14215 (WO 99/02683) discloses that the ecdysone receptor isolated from the silk moth *Bombyx mori* is functional in mammalian systems without the need for an exogenous dimer partner.

U.S. Pat. No. 6,265,173 B1 discloses that various members of the steroid/thyroid superfamily of receptors can combine with *Drosophila melanogaster* ultraspiracle receptor (USP) or fragments thereof comprising at least the dimerization domain of USP for use in a gene expression system. U.S. Pat. No. 5,880,333 discloses a *Drosophila melanogaster* EcR and ultraspiracle (USP) heterodimer system used in plants in which the transactivation domain and the DNA binding domain are positioned on two different hybrid proteins. Unfortunately, these USP-based systems are constitutive in animal cells and therefore, are not effective for regulating reporter gene expression.

In each of these cases, the transactivation domain and the DNA binding domain (either as native EcR as in International Patent Application No. PCT/US98/14215 or as modified EcR as in International Patent Application No. PCT/US97/05330) were incorporated into a single molecule and the other heterodimeric partners, either USP or RXR, were used in their native state.

Drawbacks of the above described EcR-based gene regulation systems include a considerable background activity in the absence of ligands and non-applicability of these systems for use in both plants and animals (see U.S. Pat. No. 5,880,333). Therefore, a need exists in the art for improved EcR-based systems to precisely modulate the expression of exogenous genes in both plants and animals. Such improved systems would be useful for applications such as gene therapy, large-scale production of proteins and antibodies, cell-based high throughput screening assays, functional genomics and regulation of traits in transgenic animals. For certain applications such as gene therapy, it may be desirable to have an inducible gene expression system that responds well to synthetic non-steroid ligands and at the same is insensitive to the natural steroids. Thus, improved systems that are simple, compact, and dependent on ligands that are relatively inexpensive, readily available, and of low toxicity to the host would prove useful for regulating biological systems.

Recently, it has been shown that an ecdysone receptor-based inducible gene expression system in which the transactivation and DNA binding domains are separated from each other by placing them on two different proteins results in greatly reduced background activity in the absence of a ligand and significantly increased activity over background in the presence of a ligand (pending application PCT/US01/09050, incorporated herein in its entirety by reference). This two-hybrid system is a significantly improved inducible gene expression modulation system compared to the two systems disclosed in applications PCT/US97/05330 and PCT/US98/14215. The two-hybrid system exploits the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283,173). Briefly, the two-hybrid gene expression system comprises two gene expression cassettes; the first encoding a DNA binding domain fused to a nuclear receptor polypeptide, and the second encoding a transactivation domain fused to a different nuclear receptor polypeptide. In the presence of ligand, the interaction of the first polypeptide with the second polypeptide effectively tethers the DNA binding domain to the transactivation domain. Since the DNA binding and transactivation domains reside on two different molecules, the background activity in the absence of ligand is greatly reduced.

A two-hybrid system also provides improved sensitivity to non-steroidal ligands for example, diacylhydrazines, when compared to steroidal ligands for example, ponasterone A ("PonA") or muristerone A ("MurA"). That is, when compared to steroids, the non-steroidal ligands provide higher activity at a lower concentration. In addition, since transactivation based on EcR gene switches is often cell-line dependent, it is easier to tailor switching systems to obtain maximum transactivation capability for each application. Furthermore, the two-hybrid system avoids some side effects due to overexpression of RXR that often occur when unmodified RXR is used as a switching partner. In a preferred two-hybrid system, native DNA binding and transactivation domains of EcR or RXR are eliminated and as a result, these hybrid molecules have less chance of interacting with other steroid hormone receptors present in the cell resulting in reduced side effects.

With the improvement in ecdysone receptor-based gene regulation systems there is an increase in their use in various applications resulting in increased demand for ligands with higher activity than those currently exist. U.S. Pat. No. 6,258,603 B1 (and patents cited therein) disclosed dibenzoylhydrazine ligands, however, a need exists for additional ligands with different structures and physicochemical properties. We have discovered novel non-diacylhydrazine ligands which have not previously been described or shown to have the ability to modulate the expression of transgenes.

SUMMARY OF THE INVENTION

The present invention relates to non-steroidal ligands for use in nuclear receptor-based inducible gene expression system, and methods of modulating the expression of a gene within a host cell using these ligands with nuclear receptor-based inducible gene expression systems.

Applicants' invention also relates to methods of modulating gene expression in a host cell using a gene expression modulation system with a ligand of the present invention. Specifically, Applicants' invention provides a method of modulating the expression of a gene in a host cell comprising the steps of: a) introducing into the host cell a gene expression modulation system according to the invention; b) introducing into the host cell a gene expression cassette comprising i) a response element comprising a domain to which the DNA binding domain from the first hybrid polypeptide of the gene expression modulation system binds; ii) a promoter that is activated by the transactivation domain of the second hybrid polypeptide of the gene expression modulation system; and iii) a gene whose expression is to be modulated; and c) introducing into the host cell a ligand; whereby upon introduction of the ligand into the host cell, expression of the gene is modulated. Applicants' invention also provides a method of modulating the expression of a gene in a host cell comprising a gene expression cassette comprising a response element comprising a domain to which the DNA binding domain from the first hybrid polypeptide of the gene expression modulation system binds; a promoter that is activated by the transactivation domain of the second hybrid polypeptide of the gene expression modulation system; and a gene whose expression is to be modulated; wherein the method comprises the steps of: a) introducing into the host cell a gene expression modulation system according to the invention; and b) introducing into the host cell a ligand; whereby upon introduction of the ligand into the host, expression of the gene is modulated.

DETAILED DESCRIPTION OF THE INVENTION

Applicants have discovered novel ligands for natural and mutated nuclear receptors. Thus, Applicants' invention provides a ligand for use with ecdysone receptor-based inducible gene expression system useful for modulating expression of a gene of interest in a host cell. In a particularly desirable embodiment, Applicants' invention provides an inducible gene expression system that has a reduced level of background gene expression and responds to submicromolar concentrations of non-steroidal ligand. Thus, Applicants' novel ligands and inducible gene expression system and its use in methods of modulating gene expression in a host cell overcome the limitations of currently available inducible expression systems and provide the skilled artisan with an effective means to control gene expression.

The present invention is useful for applications such as gene therapy, large scale production of proteins and antibodies, cell-based high throughput screening assays, functional genomics, proteomics, metabolomics, and regulation of traits in transgenic organisms, where control of gene expression levels is desirable. An advantage of Applicants' invention is that it provides a means to regulate gene expression and to tailor expression levels to suit the user's requirements.

The present invention pertains to compounds of the general formula:

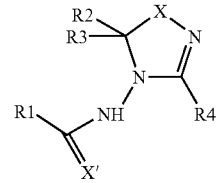

wherein X and X' are independently O or S;

$R^1$ is a) H, $(C_1-C_6)$alkyl, $(C_1-C_6)$haloalkyl, $(C_1-C_6)$cyanoalkyl, $(C_1-C_6)$alkoxycarbonyl$(C_1-C_6)$alkyl, $(C_1-C_6)$alkoxy, or benzyloxy;

b) unsubstituted or substituted phenyl wherein the substituents are independently 1 to 5 H; halo; nitro; cyano; hydroxy; amino (—$NR^aR^b$); $(C_1-C_6)$alkyl; $(C_1-C_6)$haloalkyl; $(C_1-C_6)$cyanoalkyl; $(C_1-C_6)$hydroxyalkyl; $(C_1-C_6)$alkoxy; phenoxy; $(C_1-C_6)$haloalkoxy; $(C_1-C_6)$alkoxy$(C_1-C_6)$alkyl; $(C_1-C_6)$alkoxy$(C_1-C_6)$alkoxy; $(C_1-C_6)$alkanoyloxy$(C_1-C_6)$alkyl; $(C_2-C_6)$alkenyl optionally substituted with halo, cyano, $(C_1-C_4)$ alkyl, or $(C_1-C_4)$ alkoxy; $(C_2-C_6)$alkynyl optionally substituted with halo or $(C_1-C_4)$alkyl; formyl; carboxy; $(C_1-C_6)$alkylcarbonyl; $(C_1-C_6)$haloalkylcarbonyl; benzoyl; $(C_1-C_6)$alkoxycarbonyl; $(C_1-C_6)$haloalkoxycarbonyl; $(C_1-C_6)$alkanoyloxy (—$OCOR^a$); carboxamido (—$CONR^aR^b$); amido (—$NR^aCOR^b$); alkoxycarbonylamino (—$NR^aCO_2R^b$); alkylaminocarbonylamino (—$NR^aCONR^bR^c$); mercapto; $(C_1-C_6)$alkylthio; $(C_1-C_6)$ alkylsulfonyl; $(C_1-C_6)$alkylsulfoxido (—$S(O)R^a$); sulfamido (—$SO_2NR^aR^b$); or unsubstituted or substituted phenyl wherein the substituents are independently 1 to 3 halo, nitro, $(C_1-C_6)$ alkoxy, $(C_1-C_6)$ alkyl, or amino; or when two adjacent positions on the phenyl ring are substituted with alkoxy groups, these groups, together with the carbon atoms to which they are attached, may be joined as a linkage (—$OCH_2O$—) or (—$OCH_2CH_2O$—) to form a 5- or 6-membered dioxolano or dioxano heterocyclic ring;

c) unsubstituted or substituted naphthyl wherein the substituents are independently 1 to 3 halo, nitro, $(C_1-C_6)$ alkoxy, $(C_1-C_6)$alkyl, or amino;

d) unsubstituted or substituted benzothiophene-2-yl, benzothiophene-3-yl, benzofuran-2-yl, or benzofuran-3-yl wherein the substituents are independently 1 to 3 halo, nitro, hydroxy, $(C_1-C_6)$alkyl, $(C_1-C_6)$alkoxy, carboxy, or $(C_1-C_6)$alkoxycarbonyl (—$CO_2R^a$);

e) unsubstituted or substituted 2, 3, or 4-pyridyl wherein the substituents are independently 1 to 3 halo, cyano, nitro, hydroxy, $(C_1-C_6)$alkyl, $(C_1-C_6)$alkoxy, or $(C_1-C_6)$haloalkoxy;

f) unsubstituted or substituted 5-membered heterocycle selected from furyl, thiophenyl, triazolyl, pyrrolyl, isopyrrolyl, pyrazolyl, isoimidazolyl, thiazolyl, isothiazolyl, oxazolyl, or isooxazolyl wherein the substituents are independently 1 to 3 halo, nitro, hydroxy, $(C_1-C_6)$alkyl, $(C_1-C_6)$alkoxy, carboxy, $(C_1-C_6)$alkoxycarbonyl ($-CO_2R^a$), or unsubstituted or substituted phenyl wherein the substituents are independently 1 to 3 halo, nitro, $(C_1-C_6)$alkyl, $(C_1-C_6)$haloalkyl, $(C_1-C_6)$alkoxy, $(C_1-C_6)$haloalkoxy, carboxy, $(C_1-C_4)$alkoxycarbonyl ($-CO_2R^a$), or amino ($-NR^aR^b$);

g) aromatic-substituted or unsubstituted phenyl$(C_1-C_6)$alkyl, phenyl$(C_1-C_6)$alkoxy$(C_1-C_6)$alkyl, or phenoxy$(C_1-C_6)$alkyl wherein the aromatic substituents are independently 1 to 3 halo, nitro, $(C_1-C_6)$ alkoxy, $(C_1-C_6)$alkyl, or amino; or h) aromatic-substituted or unsubstituted phenylamino, phenyl$(C_1-C_6)$alkylamino, or phenylcarbonylamino wherein the aromatic substituents are independently 1 to 3 halo, nitro, $(C_1-C_6)$alkoxy, $(C_1-C_6)$alkyl, or amino;

wherein $R^a$, $R^b$, and $R^c$ are independently H, $(C_1-C_6)$ alkyl, or phenyl;

$R^2$ and $R^3$ are independently H, $(C_1-C_6)$alkyl, $(C_1-C_6)$haloalkyl, $(C_1-C_6)$cyanoalkyl, $(C_1-C_6)$hydroxyalkyl, $(C_1-C_6)$alkoxy$(C_1-C_6)$alkyl, phenyl, or together as an alkane linkage ($-(CH_2)_x-$), an alkyloxyalkyl linkage ($-(CH_2)_yO(CH_2)_z-$), an alkylaminoalkyl linkage ($-(CH_2)_yNR^a(CH_2)_z-$), or an alkylbenzoalkyl linkage ($-(CH_2)_y$-1-benzo-2-$(CH_2)_z-$) form a ring with the carbon atom to which they are attached, wherein x=3 to 7, y=1 to 3, z=1 to 3, and $R^a$ is H, $(C_1-C_6)$alkyl, or phenyl; and $R^4$ is unsubstituted or substituted phenyl wherein the substituents are independently 1 to 5 H; halo; nitro; cyano; hydroxy; amino ($-NR^aR^b$); $(C_1-C_6)$alkyl; $(C_1-C_6)$haloalkyl; $(C_1-C_6)$cyanoalkyl; $(C_1-C_6)$hydroxyalkyl; $(C_1-C_6)$alkoxy; phenoxy; $(C_1-C_6)$haloalkoxy; $(C_1-C_6)$alkoxy$(C_1-C_6)$alkyl; $(C_1-C_6)$alkoxy$(C_1-C_6)$alkoxy; $(C_1-C_6)$alkanoyloxy$(C_1-C_6)$alkyl; $(C_2-C_6)$alkenyl optionally substituted with halo, cyano, $(C_1-C_4)$ alkyl, or $(C_1-C_4)$ alkoxy; $(C_2-C_6)$alkynyl optionally substituted with halo or $(C_1-C_4)$alkyl; formyl; carboxy; $(C_1-C_6)$alkylcarbonyl; $(C_1-C_6)$haloalkylcarbonyl; benzoyl; $(C_1-C_6)$alkoxycarbonyl; $(C_1-C_6)$haloalkoxycarbonyl; $(C_1-C_6)$alkanoyloxy ($-OCOR^a$); carboxamido ($-CONR^aR^b$); amido ($-NR^aCOR^b$); alkoxycarbonylamino ($-NR^aCO_2R^b$); alkylaminocarbonylamino ($-NR^aCONR^bR^c$); mercapto; $(C_1-C_6)$alkylthio; $(C_1-C_6)$ alkylsulfonyl; $(C_1-C_6)$alkylsulfoxido ($-S(O)R^a$); sulfamido ($-SO_2NR^aR^b$); or unsubstituted or substituted phenyl wherein the substituents are independently 1 to 3 halo, nitro, $(C_1-C_6)$ alkoxy, $(C_1-C_6)$ alkyl, or amino; or when two adjacent positions on the phenyl ring are substituted with alkoxy groups, these groups, together with the carbon atoms to which they are attached, may be joined to form a 5- or 6-membered dioxolano ($-OCH_2O-$) or dioxano ($-OCH_2CH_2O-$) heterocyclic ring; wherein $R^a$, $R^b$, and $R^c$ are independently H, $(C_1-C_6)$ alkyl, or phenyl;

provided that $R^4$ is not 3-nitrophenyl or 4-nitrophenyl, and when $R^4$ is phenyl, then $R^1$ is not phenyl, when $R^4$ is 3-chlorophenyl, then $R^1$ is not phenylamino, or when $R^4$ is 4-chlorophenyl, then $R^1$ is not methyl.

Compounds of the general formula are preferred when:

X and X' are independently O or S;

$R^1$ is a) H, $(C_1-C_6)$alkyl, $(C_1-C_6)$haloalkyl, $(C_1-C_6)$cyanoalkyl, $(C_1-C_6)$alkoxycarbonyl$(C_1-C_6)$alkyl, $(C_1-C_6)$alkoxy, or benzyloxy;

b) unsubstituted or substituted phenyl wherein the substituents are independently 1 to 5 H; halo; nitro; cyano; hydroxy; $(C_1-C_6)$alkyl; $(C_1-C_6)$haloalkyl; $(C_1-C_6)$cyanoalkyl; $(C_1-C_6)$hydroxyalkyl; $(C_1-C_6)$alkoxy; $(C_1-C_6)$haloalkoxy; $(C_1-C_6)$alkoxy$(C_1-C_6)$alkyl; $(C_1-C_6)$alkanoyloxy$(C_1-C_6)$alkyl; $(C_2-C_6)$alkenyl optionally substituted with halo, cyano, $(C_1-C_4)$ alkyl, or $(C_1-C_4)$ alkoxy; $(C_2-C_6)$alkynyl optionally substituted with halo or $(C_1-C_4)$alkyl; formyl; carboxy; $(C_1-C_6)$alkylcarbonyl; $(C_1-C_6)$haloalkylcarbonyl; benzoyl; $(C_1-C_6)$alkoxycarbonyl; $(C_1-C_6)$alkanoyloxy ($-OCOR^a$); carboxamido ($-CONR^aR^b$); amido ($-NR^aCOR^b$); $(C_1-C_6)$ alkylsulfonyl; $(C_1-C_6)$alkylsulfoxido ($-S(O)R^a$); sulfamido ($-SO_2NR^aR^b$); or unsubstituted or substituted phenyl wherein the substituents are independently 1 to 3 halo, nitro, $(C_1-C_6)$ alkoxy, $(C_1-C_6)$alkyl, or amino; or when two adjacent positions on the phenyl ring are substituted with alkoxy groups, these groups, together with the carbon atoms to which they are attached, may be joined as a linkage ($-OCH_2O-$) or ($-OCH_2CH_2O-$) to form a 5- or 6-membered dioxolano or dioxano heterocyclic ring;

c) unsubstituted or substituted benzothiophene-2-yl, or benzofuran-2-yl wherein the substituents are independently 1 to 3 halo, nitro, hydroxy, $(C_1-C_6)$alkyl, or $(C_1-C_6)$alkoxy;

d) unsubstituted or substituted 2, 3, or 4-pyridyl wherein the substituents are independently 1 to 3 halo, cyano, nitro, hydroxy, $(C_1-C_6)$alkyl, $(C_1-C_6)$alkoxy, or $(C_1-C_6)$ haloalkoxy;

e) unsubstituted or substituted 5-membered heterocycle selected from furyl, thiophenyl, triazolyl, pyrazolyl, thiazolyl, isothiazolyl, oxazolyl, or isooxazolyl wherein the substituents are independently 1 to 3 halo, nitro, hydroxy, $(C_1-C_6)$alkyl, $(C_1-C_6)$alkoxy, carboxy, $(C_1-C_6)$alkoxycarbonyl ($-CO_2R^a$), or unsubstituted or substituted phenyl wherein the substituents are independently 1 to 3 halo, nitro, $(C_1-C_6)$alkyl, $(C_1-C_6)$haloalkyl, $(C_1-C_6)$alkoxy, $(C_1-C_6)$haloalkoxy, carboxy, or $(C_1-C_4)$alkoxycarbonyl ($-CO_2R^a$);

f) aromatic-substituted or unsubstituted phenyl$(C_1-C_6)$alkyl, phenyl$(C_1-C_6)$alkoxy$(C_1-C_6)$alkyl, or phenoxy$(C_1-C_6)$alkyl wherein the aromatic substituents are independently 1 to 3 halo, nitro, $(C_1-C_6)$ alkoxy, or $(C_1-C_6)$alkyl; or g) aromatic-substituted or unsubstituted phenylamino, phenyl$(C_1-C_6)$alkylamino, or phenylcarbonylamino wherein the aromatic substituents are independently 1 to 3 halo, nitro, $(C_1-C_6)$ alkoxy, or $(C_1-C_6)$alkyl;

wherein $R^a$ and $R^b$ are independently H, $(C_1-C_6)$alkyl, or phenyl;

$R^2$ and $R^3$ are independently H, $(C_1-C_6)$alkyl, $(C_1-C_6)$haloalkyl, $(C_1-C_6)$cyanoalkyl, $(C_1-C_6)$hydroxyalkyl, $(C_1-C_6)$alkoxy$(C_1-C_6)$alkyl, phenyl, or together as an alkane linkage ($-(CH_2)_x-$), an alkyloxylalkyl linkage ($-(CH_2)_yO(CH_2)_z-$), an alkylaminoalkyl linkage ($-(CH_2)_yNR^a(CH_2)_z-$), or an alkylbenzoalkyl linkage ($-(CH_2)_y$-1-benzo-2-$(CH_2)_z-$) form a ring with the carbon atom to which they are attached, wherein x=3 to 7, y=1 to 3, z=1 to 3, and $R^a$ is H, $(C_1-C_6)$alkyl, or phenyl and $R^4$ is unsubstituted or substituted phenyl wherein the substituents are independently 1 to 5 H; halo; nitro; cyano; hydroxy; $(C_1-C_6)$alkyl; $(C_1-C_6)$haloalkyl; $(C_1-C_6)$cyanoalkyl; $(C_1-C_6)$hydroxyalkyl; $(C_1-C_6)$alkoxy; $(C_1-C_6)$haloalkoxy; $(C_1-C_6)$alkoxy$(C_1-C_6)$alkyl; $(C_1-C_6)$alkanoyloxy $(C_1-C_6)$alkyl; $(C_2-C_6)$alkenyl optionally substituted with halo, cyano, $(C_1-C_4)$ alkyl, or $(C_1-C_4)$alkoxy; $(C_2-C_6)$alkynyl optionally substituted with halo or $(C_1-C_4)$alkyl; formyl; carboxy; $(C_1-C_6)$alkylcarbonyl; $(C_1-C_6)$haloalkylcarbonyl; benzoyl; $(C_1-C_6)$alkoxycarbonyl; $(C_1-C_6)$alkanoyloxy ($-OCOR^a$); carboxamido ($-CONR^aR^b$); amido ($-NR^aCOR^b$); $(C_1-C_6)$ alkylsulfonyl; $(C_1-C_6)$alkylsulfoxido ($-S(O)R^a$); sulfamido ($-SO_2NR^aR^b$); or unsubstituted or substituted phenyl wherein the substituents are independently 1 to 3 halo, nitro, $(C_1-C_6)$ alkoxy, $(C_1-C_6)$alkyl, or amino; or when two adjacent positions on the phenyl ring are substituted with alkoxy groups, these groups, together with the carbon atoms to which they are attached, may be joined as a linkage ($-OCH_2O-$) or ($-OCH_2CH_2O-$) to form a 5- or 6-membered dioxolano or dioxano heterocyclic ring; wherein $R^a$ and $R^b$ are independently H, $(C_1-C_6)$alkyl, or phenyl;

provided that $R^4$ is not 3-nitrophenyl or 4-nitrophenyl, and when $R^4$ is phenyl, then $R^1$ is not phenyl, when $R^4$ is 3-chlorophenyl, then $R^1$ is not phenylamino, or when $R^4$ is 4-chlorophenyl, then $R^1$ is not methyl.

Compounds of the general formula are more preferred when:

X is O;

X' is O or S;

$R^1$ is a) H, $(C_1-C_6)$alkyl, $(C_1-C_6)$haloalkyl, or $(C_1-C_6)$alkoxycarbonyl$(C_1-C_6)$alkyl;

b) unsubstituted or substituted phenyl wherein the substituents are independently 1 to 5 H; halo; nitro; cyano; $(C_1-C_6)$alkyl; $(C_1-C_6)$haloalkyl; $(C_1-C_6)$alkoxy; $(C_1-C_6)$haloalkoxy; $(C_1-C_6)$alkylcarbonyl; $(C_1-C_6)$alkoxycarbonyl; carboxamido ($-CONR^aR^b$); amido ($-NR^aCOR^b$); or phenyl; or when two adjacent positions on the phenyl ring are substituted with alkoxy groups, these groups, together with the carbon atoms to which they are attached, may be joined as a linkage ($-OCH_2O-$) or ($-OCH_2CH_2O-$) to form a 5- or 6-membered dioxolano or dioxano heterocyclic ring;

c) unsubstituted or substituted benzothiophene-2-yl, or benzofuran-2-yl wherein the substituents are independently 1 to 3 halo, nitro, hydroxy, $(C_1-C_6)$alkyl, or $(C_1-C_6)$alkoxy;

d) unsubstituted or substituted furyl or thiophenyl wherein the substituents are independently 1 to 3 halo, nitro, $(C_1-C_6)$alkyl, $(C_1-C_6)$alkoxy, carboxy, $(C_1-C_6)$alkoxycarbonyl ($-CO_2R^a$), or phenyl;

e) aromatic-substituted or unsubstituted phenyl$(C_1-C_6)$alkyl, phenyl$(C_1-C_6)$alkoxy$(C_1-C_6)$alkyl, or phenoxy $(C_1-C_6)$alkyl wherein the aromatic substituents are independently 1 to 3 halo, nitro, $(C_1-C_6)$ alkoxy, or $(C_1-C_6)$alkyl; or f) aromatic-substituted or unsubstituted phenylamino, phenyl$(C_1-C_6)$alkylamino, or phenylcarbonylamino wherein the aromatic substituents are independently 1 to 3 halo, nitro, $(C_1-C_6)$ alkoxy, or $(C_1-C_6)$alkyl;

wherein $R^a$ and $R^b$ are independently H, $(C_1-C_6)$alkyl, or phenyl;

$R^2$ and $R^3$ are independently H, $(C_1-C_6)$alkyl, $(C_1-C_6)$haloalkyl, $(C_1-C_6)$alkoxy$(C_1-C_6)$alklyl, phenyl, or together as an alkane linkage ($-(CH_2)_x-$), an alkyloxylalkyl linkage ($-(CH_2)_yO(CH_2)_z-$), an alkylaminoalkyl linkage ($-(CH_2)_yNR^a(CH_2)_z-$), or an alkylbenzoalkyl linkage ($-(CH_2)_y$-1-benzo-2-$(CH_2)_z-$) form a ring with the carbon atom to which they are attached, wherein x=3 to 7, y=1 to 3, z=1 to 3, and $R^a$ is H, $(C_1-C_6)$alkyl, or phenyl; and $R^4$ is unsubstituted or substituted phenyl wherein the substituents are independently 1 to 5 H; halo; nitro; cyano; $(C_1-C_6)$alkyl; $(C_1-C_6)$haloalkyl; $(C_1-C_6)$alkoxy; $(C_1-C_6)$haloalkoxy; $(C_1-C_6)$alkylcarbonyl; $(C_1-C_6)$alkoxycarbonyl; carboxamido ($-CONR^aR^b$); amido ($-NR^aCOR^b$); or phenyl; or when two adjacent positions on the phenyl ring are substituted with alkoxy groups, these groups, together with the carbon atoms to which they are attached, may be joined as a linkage ($-OCH_2O-$) or ($-OCH_2CH_2O-$) to form a 5- or 6-membered dioxolano or dioxano heterocyclic ring; wherein $R^a$ and $R^b$ are independently H, $(C_1-C_6)$alkyl, or phenyl;

provided that $R^4$ is not 3-nitrophenyl or 4-nitrophenyl, and when $R^4$ is phenyl, then $R^1$ is not phenyl, when $R^4$ is 3-chlorophenyl, then $R^1$ is not phenylamino, or when $R^4$ is 4-chlorophenyl, then $R^1$ is not methyl.

Compounds of the general formula are even more preferred when:

X and X' are O;

$R^1$ is phenyl, 4-chlorophenyl-, 4-ethylphenyl-, 2-ethyl-3,4-ethylenedioxyphenyl, 3-fluorophenyl-, 2-fluoro-4-ethylphenyl-, 2-methyl-3-methoxyphenyl-, 2-ethyl-3-methoxyphenyl, 3-methylphenyl-, 2-methoxyphenyl-, 2-nitrophenyl-, 3-nitrophenyl-, 2-furanyl-, benzyl-, benzothiophene-2-yl-, phenylamino-, benzyloxymethyl, phenoxymethyl-, 3-toluoylamino-, benzylamino-, benzoylamino-, ethoxycarbonylethyl-, or 3-chloro-2,2,3,3-tetrafluoroethyl;

$R^2$ and $R^3$ are independently methyl, ethyl, or together as a tetramethylene ($-(CH2)_4-$), 4-pyrano ($-CH_2CH_2OCH_2CH_2-$), or methylenebenzoethylene ($-CH_2$-1-benzo-2-$CH_2CH_2-$) linkage form a ring with the carbon atom to which they are attached; and $R^4$ is phenyl, 4-biphenyl, 4-chlorophenyl, 2,4-dimethoxyphenyl, 3,5-dimethylphenyl, 2-methoxyphenyl, 3,4-methylenedioxyphenyl, 3-trifluoromethylphenyl, or 4-trifluromethoxyphenyl;

provided that when $R^4$ is phenyl, then $R^1$ is not phenyl.

The compounds of the present invention most preferred are the following:

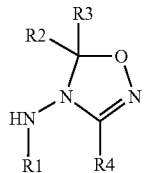

| Compound | R1 | R2 | R3 | R4 |
| --- | --- | --- | --- | --- |
| RG-120001 | PhNHC(O)— | CH₃— | CH₃— | 3-CF₃-Ph- |
| RG-120002 | 3-F-benzoyl- | CH₃— | CH₃— | 3,5-di-CH₃-Ph- |
| RG-120003 | 2-furanoyl- | —(CH₂)₄— | | 3,5-di-CH₃-Ph- |
| RG-120004 | CClF₂CF₂C(O)— | CH₃CH₂— | CH₃— | 3,5-di-CH₃-Ph- |
| RG-120005 | 4-CH₃CH₂-benzoyl- | —CH₂CH₂OCH₂CH₂— | | 3,5-di-CH₃-Ph- |
| RG-120006 | PhCH₂OCH₂C(O)— | CH₃— | CH₃— | 3-CF₃-Ph- |
| RG-120008 | 2-CH₃CH₂-3-CH₃O-benzoyl- | —CH₂CH₂OCH₂CH₂— | | 3,5-di-CH₃-Ph- |
| RG-120009 | PhCH₂OCH₂C(O)— | —CH₂CH₂OCH₂CH₂— | | 3,5-di-CH₃-Ph- |
| RG-120011 | Benzoyl- | —(CH₂)₄— | | 3,5-di-CH₃-Ph- |
| RG-120012 | 2-furanoyl- | CH₃— | CH₃— | 2-CH₃O-Ph- |
| RG-120013 | PhOCH₂C(O)— | —CH₂CH₂OCH₂CH₂— | | Ph- |
| RG-120014 | CH₃CH₂OC(O)CH₂CH₂C(O)— | —(CH₂)₄— | | Ph- |
| RG-120015 | Benzoyl- | CH₃— | CH₃— | 3-CF₃-Ph- |
| RG-120016 | 2-CH₃CH₂-3-CH₃O-benzoyl- | CH₃— | CH₃— | 2-CH₃O-Ph- |
| RG-120017 | PhNHC(O)— | CH₃— | CH₃— | 3,4-OCH₂O-Ph- |
| RG-120018 | PhCH₂OCH₂C(O)— | CH₃— | CH₃— | 2-CH₃O-Ph- |
| RG-120019 | Benzoyl- | —CH₂CH₂OCH₂CH₂— | | 3,5-di-CH₃-Ph- |
| RG-120020 | 2-CH₃CH₂-3-CH₃O-benzoyl- | CH₃— | CH₃— | 4-Ph-Ph- |
| RG-120021 | PhCH₂C(O)— | CH₃— | CH₃— | 3-CF₃-Ph- |
| RG-120022 | 2-CH₃CH₂-3-CH₃O-benzoyl- | CH₃— | CH₃— | 4-CF₃O-Ph- |
| RG-120023 | 2-CH₃CH₂-3-CH₃O-benzoyl- | CH₃— | CH₃— | 3,4-OCH₂O-Ph- |
| RG-120024 | 4-Cl-benzoyl- | CH₃— | CH₃— | 3,5-di-CH₃-Ph- |
| RG-120025 | PhNHC(O)— | CH₃— | CH₃— | 2-CH₃O-Ph- |
| RG-120026 | 4-CH₃CH₂-benzoyl- | CH₃— | CH₃— | 2-CH₃O-Ph- |
| RG-120027 | PhNHC(O)— | —CH2CH2OCH2CH2- | | Ph- |
| RG-120029 | PhOCH₂C(O)— | CH₃— | CH₃— | 4-CF₃O-Ph- |
| RG-120030 | PhCH₂C(O)— | —(CH₂)₄— | | Ph- |
| RG-120031 | CH3CH2OC(O)CH2CH2C(O)— | —(CH₂)₄— | | 3,5-di-CH₃-Ph- |
| RG-120033 | Benzoyl- | CH₃— | CH₃— | 4-CF₃O-Ph- |
| RG-120034 | PhCH₂OCH₂C(O)— | —CH₂CH₂OCH₂CH₂— | | Ph- |
| RG-120035 | 4-CH₃CH₂-benzoyl- | CH₃— | CH₃— | 4-Cl-Ph- |
| RG-120037 | 2-CH₃-3-CH₃O-benzoyl- | —CH₂-1-benzo-2-CH₂CH₂— | | 3,5-di-CH₃-Ph- |
| RG-120038 | CH₃CH₂OC(O)CH₂CH₂C(O)— | CH₃— | CH₃— | 2,4-di-CH₃O-Ph- |
| RG-120039 | Benzoyl- | CH₃CH₂— | CH₃— | 3,5-di-CH₃-Ph- |
| RG-120040 | 4-CH₃CH₂-benzoyl- | —(CH₂)₄— | | 3,5-di-CH₃-Ph- |
| RG-120041 | PhOCH₂C(O)— | —(CH₂)₄— | | 3,5-di-CH₃-Ph- |
| RG-120042 | 2-CH₃-3-CH₃O-benzoyl- | CH₃— | CH₃— | Ph- |
| RG-120044 | Benzoyl- | —CH₂CH₂OCH₂CH₂— | | Ph- |
| RG-120045 | 2-CH₃-3-CH₃O-benzoyl- | CH₃— | CH₃— | 3,5-di-CH₃-Ph- |
| RG-120046 | PhCH₂C(O)— | —(CH₂)₄— | | 3,5-di-CH₃-Ph- |
| RG-120047 | benzothiophene-2-C(O)— | CH₃— | CH₃— | 2-CH₃O-Ph- |
| RG-120048 | PhOCH₂C(O)— | —CH₂CH₂OCH₂CH₂— | | 3,5-di-CH₃-Ph- |
| RG-120049 | 2-CH₃CH₂-3-CH₃O-benzoyl- | —(CH₂)₄— | | 3,5-di-CH₃-Ph- |
| RH-120050 | PhCH₂OCH₂C(O)— | CH₃CH₂— | CH₃— | 3,5-di-CH₃-Ph- |
| RG-120051 | PhNHC(O)— | CH₃CH₂— | CH₃— | 3,5-di-CH₃-Ph- |
| RG-120052 | PhCH₂OCH₂C(O)— | —(CH₂)₄— | | 3,5-di-CH₃-Ph- |
| RG-120054 | PhNHC(O)— | —CH₂CH₂OCH₂CH₂— | | 3,5-di-CH₃-Ph- |
| RG-120055 | 4-CH₃CH₂-benzoyl- | CH₃— | | 4-CF₃O-Ph- |
| RG-120056 | 3-CH₃PhNHC(O)— | CH₃— | | 3,5-di-CH₃-Ph- |
| RG-120057 | PhOCH₂C(O)— | CH₃— | | 2-CH₃O-Ph- |
| RG-120058 | 2-CH₃CH₂-3-CH₃O-benzoyl- | CH₃— | | 2,4-di-CH₃O-Ph- |
| RG-120059 | CClF₂CF₂C(O)— | CH₃— | | 3-CF₃-Ph- |
| RG-120060 | 4-CH₃CH₂-benzoyl- | CH₃— | | 3,5-di-CH₃-Ph- |
| RG-120061 | 4-CH₃CH₂-benzoyl- | CH₃— | | 3,4-OCH₂O-Ph- |
| RG-120062 | CClF₂CF₂C(O)— | CH₃— | | 2-CH₃O-Ph- |
| RG-120063 | CClF₂CF₂C(O)— | —(CH₂)₄— | | Ph- |
| RG-120066 | PhCH₂OCH₂C(O)— | CH₃— | CH₃— | 4-CF₃O-Ph- |
| RG-120067 | PhNHC(O)— | CH₃— | CH₃— | 4-Cl-Ph- |
| RG-120069 | 2-CH₃CH₂-3-CH₃O-benzoyl- | CH₃CH₂— | CH₃— | 3,5-di-CH₃-Ph- |
| RG-120070 | 2-furanoyl- | CH₃— | CH₃— | 3-CF₃-Ph- |
| RG-120071 | 2-furanoyl | —(CH₂)₄— | | Ph- |
| RG-120072 | PhNHC(O)— | CH₃— | CH₃— | 3,5-di-CH₃-Ph- |
| RG-120073 | CClF₂CF₂C(O)— | CH₃— | CH₃— | 4-Cl-Ph- |
| RG-120075 | 2-CH₃O-benzoyl- | CH₃— | CH₃— | 3,5-di-CH₃-Ph- |

-continued

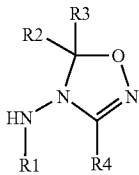

| Compound | R1 | R2 | R3 | R4 |
|---|---|---|---|---|
| RG-120076 | 2-CH$_3$CH$_2$-3-CH$_3$O-benzoyl- | CH$_3$CH$_2$— | CH$_3$— | Ph- |
| RG-120077 | 3-CH$_3$-benzoyl- | CH$_3$— | CH$_3$— | 3,5-di-CH$_3$-Ph- |
| RG-120078 | PhCH$_2$C(O)— | CH$_3$— | CH$_3$— | 2,4-di-CH$_3$O-Ph- |
| RG-120079 | PhOCH$_2$C(O)— | CH$_3$— | CH$_3$— | 2,4-di-CH$_3$O-Ph- |
| RG-120080 | 2-CH$_3$CH$_2$-3-CH$_3$O-benzoyl- | CH$_3$— | CH$_3$— | 3,5-di-CH$_3$-Ph- |
| RG-120081 | PhCH$_2$C(O)— | CH$_3$— | CH$_3$— | 3,4-OCH$_2$O-Ph- |
| RG-120082 | 2-furanoyl- | CH$_3$— | CH$_3$— | 4-Cl-Ph- |
| RG-120083 | CH$_3$CH$_2$OC(O)CH$_2$CH$_2$C(O)— | CH$_3$— | CH$_3$— | 3,4-OCH$_2$O-Ph- |
| RG-120084 | PhCH$_2$C(O)— | —CH$_2$CH$_2$OCH$_2$CH$_2$— | | 3,5-di-CH$_3$-Ph- |
| RG-120086 | 2-CH$_3$-3-CH$_3$O-benzoyl- | —CH$_2$CH$_2$OCH$_2$CH$_2$— | | 3,5-di-CH$_3$-Ph- |
| RG-120087 | benzothiophene-2-C(O)— | CH$_3$— | CH$_3$— | 4-Cl-Ph- |
| RG-120088 | PhCH$_2$NHC(O)— | CH$_3$— | CH$_3$— | 3,5-di-CH$_3$-Ph- |
| RG-120089 | Benzoyl- | —(CH$_2$)$_4$— | | Ph- |
| RG-120090 | CClF$_2$CF$_2$C(O)— | —(CH$_2$)$_4$— | | 3,5-di-CH$_3$-Ph- |
| RG-120091 | 3-NO$_2$-benzoyl- | CH$_3$— | CH$_3$— | 3,5-di-CH$_3$-Ph- |
| RG-120092 | 2-CH$_3$CH$_2$-3-CH$_3$O-benzoyl- | —(CH$_2$)$_4$— | | Ph- |
| RG-120093 | 2-CH$_3$CH$_2$-3-CH$_3$O-benzoyl- | CH$_3$— | CH$_3$— | 3-CF$_3$-Ph- |
| RG-120094 | 2-furanoyl- | CH$_3$— | CH$_3$— | 4-CF$_3$O-Ph- |
| RG-120095 | PhNHC(O)— | CH$_3$CH$_2$— | CH$_3$— | Ph- |
| RG-120096 | Benzoyl- | CH$_3$— | CH$_3$— | 2,4-di-CH$_3$O-Ph- |
| RG-120098 | 2-NO$_2$-benzoyl- | CH$_3$— | CH$_3$— | 3,5-di-CH$_3$-Ph- |
| RG-120099 | 2-CH$_3$CH$_2$-3-CH$_3$O-benzoyl- | CH$_3$— | CH$_3$— | 4-Cl-Ph- |
| RG-120100 | 2-furanoyl- | CH$_3$CH$_2$— | CH$_3$— | Ph- |
| RG-120102 | 2-furanoyl- | CH$_3$— | CH$_3$— | 2,4-di-CH$_3$O-Ph- |
| RG-120103 | PhOCH$_2$C(O)— | CH$_3$CH$_2$— | CH$_3$— | Ph- |
| RG-120106 | 2-furanoyl- | CH$_3$CH$_2$— | CH$_3$— | 3,5-di-CH$_3$-Ph- |
| RG-120108 | benzothiophene-2-C(O)— | CH$_3$— | CH$_3$— | 3-CF$_3$-Ph- |
| RG-120109 | benzothiophene-2-C(O)— | CH$_3$— | CH$_3$— | 4-CF$_3$O-Ph- |
| RG-120110 | PhCH$_2$OCH$_2$C(O)— | CH$_3$— | CH$_3$— | 2,4-di-CH$_3$O-Ph- |
| RG-120111 | PhC(O)NHC(O)— | CH$_3$— | CH$_3$— | 3,5-di-CH$_3$-Ph- |
| RG-120112 | PhNHC(O)— | —(CH$_2$)$_4$— | | 3,5-di-CH$_3$-Ph- |
| RG-120114 | PhNHC(O)— | CH$_3$— | CH$_3$— | 2,4-di-CH$_3$O-Ph- |
| RG-120115 | 4-CH$_3$CH$_2$-benzoyl- | CH$_3$— | CH$_3$— | Ph- |
| RG-120117 | PhCH$_2$OCH$_2$C(O)— | CH$_3$— | CH$_3$— | 4-Cl-Ph- |
| RG-120118 | Benzoyl- | CH$_3$CH$_2$— | CH$_3$— | Ph- |
| RG-120120 | PhCH$_2$C(O)— | CH$_3$CH$_2$— | CH$_3$— | 3,5-di-CH$_3$-Ph- |
| RG-120121 | PhCH$_2$C(O)— | CH$_3$— | CH$_3$— | 4-Cl-Ph- |
| RG-120122 | PhNHC(O)— | CH$_3$— | CH$_3$— | 4-CF$_3$O-Ph- |
| RG-120124 | 4-CH$_3$CH$_2$-benzoyl- | —CH$_2$CH$_2$OCH$_2$CH$_2$— | | Ph- |
| RG-120125 | 4-CH$_3$CH$_2$-benzoyl- | —(CH$_2$)$_4$— | | Ph- |
| RG-120126 | CH$_3$CH$_2$OC(O)CH$_2$CH$_2$C(O)— | CH3CH$_2$— | CH$_3$— | 3,5-di-CH$_3$-Ph- |
| RG-120127 | PhOCH$_2$C(O)— | CH$_3$— | CH$_3$— | 3,4-OCH$_2$O-Ph- |
| RG-120128 | 4-CH$_3$CH$_2$-benzoyl- | CH$_3$CH$_2$— | CH$_3$— | 3,5-di-CH$_3$-Ph- |
| RG-120129 | benzothiophene-2-C(O)— | CH$_3$— | CH$_3$— | 2,4-di-CH$_3$O-Ph- |
| RG-120130 | PhCH$_2$C(O)— | —CH$_2$CH$_2$OCH$_2$CH$_2$— | | Ph- |
| RG-120132 | PhNHC(O)— | —(CH$_2$)$_4$— | | Ph- |
| RG-120133 | benzothiophene-2-C(O)— | CH$_3$CH$_2$— | CH$_3$— | Ph- |
| RG-120135 | 4-CH$_3$CH$_2$-benzoyl- | CH$_3$— | CH$_3$— | 2,4-di-CH$_3$O-Ph- |
| RG-120137 | 4-CH$_3$CH$_2$-benzoyl- | CH$_3$CH$_2$— | CH$_3$— | Ph- |
| RG-120138 | 2-furanoyl- | —CH$_2$CH$_2$OCH$_2$CH$_2$— | | 3,5-di-CH$_3$-Ph- |
| RG-120140 | benzothiophene-2-C(O)— | CH$_3$— | CH$_3$— | 3,4-OCH$_2$O-Ph- |
| RG-120141 | PhOCH$_2$C(O)— | CH$_3$CH$_2$— | CH$_3$— | 3,5-di-CH$_3$—Ph- |
| RG-120142 | 4-CH$_3$CH$_2$-benzoyl- | CH$_3$'3 | CH$_3$— | 4-Ph-Ph- |
| RG-120144 | CH$_3$CH$_2$OC(O)CH$_2$CH$_2$C(O)— | CH$_3$— | CH$_3$— | 2-CH$_3$O-Ph- |
| RG-120145 | PhCH$_2$OCH$_2$C(O)— | CH$_3$— | CH$_3$— | 3,4-OCH$_2$O-Ph- |
| RG-120146 | PhCH$_2$C(O)— | CH$_3$CH$_2$— | CH$_3$— | Ph- |
| RG-120147 | Benzoyl- | CH$_3$— | CH$_3$— | 2-CH$_3$O-Ph- |
| RG-120148 | 4-CH$_3$CH$_2$-benzoyl- | CH$_3$'3 | CH$_3$— | 3-CF$_3$-Ph- |
| RG-120149 | 2-furanoyl- | CH$_3$— | CH$_3$— | 3,4-OCH$_2$O-Ph- |
| RG-120150 | benzothiophene-2-C(O)— | —(CH$_2$)$_4$— | | Ph- |
| RG-120151 | Benzoyl- | CH$_3$— | CH$_3$— | 4-Cl-Ph- |
| RG-120152 | benzothiophene-2-C(O)— | —(CH$_2$)$_4$— | | 3,5-di-CH$_3$-Ph- |
| RG-120153 | CH$_3$CH$_2$OC(O)CH$_2$CH$_2$C(O)— | CH$_3$— | CH$_3$— | 3-CF$_3$-Ph- |
| RG-120154 | PhCH$_2$OCH$_2$C(O)— | CH$_3$CH$_2$— | CH$_3$— | Ph- |
| RG-120155 | PhCH$_2$OCH$_2$C(O)— | —(CH$_2$)$_4$— | | Ph- |
| RG-120156 | Benzoyl- | CH$_3$— | CH$_3$— | 3,4-OCH$_2$O-Ph- |
| RG-120157 | PhCH$_2$C(O)— | CH$_3$— | CH$_3$— | 2-CH$_3$O-Ph- |

-continued

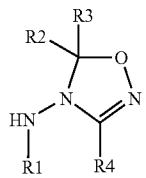

| Compound | R1 | R2 | R3 | R4 |
|---|---|---|---|---|
| RG-120158 | PhOCH$_2$C(O)— | —(CH$_2$)$_4$— | | Ph- |
| RG-120159 | 2-CH$_3$CH$_2$-3-CH$_3$O-benzoyl- | —CH$_2$CH$_2$OCH$_2$CH$_2$— | | Ph- |
| RG-120160 | PhCH$_2$C(O)— | CH$_3$— | CH$_3$— | 4-CF$_3$O-Ph- |
| RG-120161 | benzothiophene-2-C(O)— | CH$_3$CH$_2$— | CH$_3$— | 3,5-di-CH$_3$-Ph- |
| RG-120162 | PhOCH$_2$C(O)— | CH$_3$— | CH$_3$— | 4-Cl-Ph- |
| RG-120163 | PhOCH$_2$C(O)— | CH$_3$— | CH$_3$— | 3-CF$_3$-Ph- |
| RG-120164 | CH$_3$CH$_2$OC(O)CH$_2$CH$_2$C(O)— | CH$_3$— | CH$_3$— | 4-Cl-Ph- |
| RG-121513 | 2-F-4-CH$_3$CH$_2$-benzoyl- | CH$_3$— | CH$_3$CH$_2$— | 3,5-di-CH$_3$-Ph- |
| RG-121514 | 2-F-4-CH$_3$CH$_2$-benzoyl- | —(CH$_2$)$_4$— | | Ph- |
| RG-121515 | 2-F-4-CH$_3$CH$_2$-benzoyl- | —(CH$_2$)$_4$— | | 3,5-di-CH$_3$-Ph- |
| RG-121516 | 2-F-4-CH$_3$CH$_2$-benzoyl- | CH$_3$— | CH$_3$— | Ph- |
| RG-121517 | 2-CH$_3$CH$_2$-3,4-OCH$_2$CH$_2$O-benzoyl- | CH$_3$— | CH$_3$— | Ph- |
| RG-121518 | 2-CH$_3$CH2-3,4-OCH$_2$CH$_2$O-benzoyl- | CH$_3$— | CH$_3$CH$_2$— | 3,5-di-CH$_3$-Ph- |

Because the compounds of the general formula of the present invention may contain a number of stereogenic carbon atoms, the compounds may exist as enantiomers, diastereomers, stereoisomers, or their mixtures, even if a stereogenic center is explicitly specified.

Definitions

The term "alkyl" includes both branched and straight chain alkyl groups. Typical alkyl groups include, for example, methyl, ethyl, n-propyl, isopropyl, n-butyl, sec-butyl, isobutyl, tert-butyl, n-pentyl, isopentyl, n-hexyl, n-heptyl, isooctyl, nonyl, and decyl.

The term "halo" refers to fluoro, chloro, bromo or iodo.

The term "haloalkyl" refers to an alkyl group substituted with one or more halo groups such as, for example, chloromethyl, 2-bromoethyl, 3-iodopropyl, trifluoromethyl, and perfluoropropyl.

The term "cycloalkyl" refers to a cyclic aliphatic ring structure, optionally substituted with alkyl, hydroxy, or halo, such as cyclopropyl, methylcyclopropyl, cyclobutyl, 2-hydroxycyclopentyl, cyclohexyl, and 4-chlorocyclohexyl.

The term "hydroxyalkyl" refers to an alkyl group substituted with one or more hydroxy groups such as, for example, hydroxymethyl and 2,3-dihydroxybutyl.

The term "alkylsulfonyl" refers to a sulfonyl moiety substituted with an alkyl group such as, for example, mesyl, and n-propylsulfonyl.

The term "alkenyl" refers to an ethylenically unsaturated hydrocarbon group, straight or branched chain, having 1 or 2 ethylenic bonds such as, for example, vinyl, allyl, 1-butenyl, 2-butenyl, isopropenyl, and 2-pentenyl.

The term "haloalkenyl" refers to an alkenyl group substituted with one or more halo groups.

The term "alkynyl" refers to an unsaturated hydrocarbon group, straight or branched, having 1 or 2 acetylenic bonds such as, for example, ethynyl and propargyl.

The term "alkylcarbonyl" refers to an alkylketo functionality, for example acetyl, n-butyryl and the like.

The term "heterocyclyl" or "heterocycle" refers to an unsubstituted or substituted; saturated, partially unsaturated, or unsaturated 5 or 6-membered ring containing one, two or three heteroatoms, preferably one or two heteroatoms independently selected from the group consisting of oxygen, nitrogen and sulfur. Examples of heterocyclyls include, for example, pyridyl, thienyl, furyl, pyrimidinyl, pyrazinyl, quinolinyl, isoquinolinyl, pyrrolyl, indolyl, tetrahydrofuryl, pyrrolidinyl, piperidinyl, tetrahydropyranyl, morpholinyl, piperazinyl, dioxolanyl, and dioxanyl.

The term "alkoxy" includes both branched and straight chain alkyl groups attached to a terminal oxygen atom. Typical alkoxy groups include, for example, methoxy, ethoxy, n-propoxy, isopropoxy, and tert-butoxy.

The term "haloalkoxy" refers to an alkoxy group substituted with one or more halo groups such as, for example chloromethoxy, trifluoromethoxy, difluoromethoxy, and perfluoroisobutoxy.

The term "alkylthio" includes both branched and straight chain alkyl groups attached to a terminal sulfur atom such as, for example methylthio.

The term "haloalkylthio" refers to an alkylthio group substituted with one or more halo groups such as, for example trifluoromethylthio.

The term "alkoxyalkyl" refers to an alkyl group substituted with an alkoxy group such as, for example, isopropoxymethyl.

"Silica gel chromatography" refers to a purification method wherein a chemical substance of interest is applied as a concentrated sample to the top of a vertical column of silica gel or chemically-modified silica gel contained in a glass, plastic, or metal cylinder, and elution from such column with a solvent or mixture of solvents.

"Flash chromatography" refers to silica gel chromatography performed under air, argon, or nitrogen pressure typically in the range of 10 to 50 psi.

"Gradient chromatography" refers to silica gel chromatography in which the chemical substance is eluted from a column with a progressively changing composition of a solvent mixture.

"Rf" is a thin layer chromatography term which refers to the fractional distance of movement of a chemical substance of interest on a thin layer chromatography plate, relative to the distance of movement of the eluting solvent system.

The term "isolated" for the purposes of the present invention designates a biological material (nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated". The term "purified" does not require the material to be present in a form exhibiting absolute purity, exclusive of the presence of other compounds. It is rather a relative definition.

A polynucleotide is in the "purified" state after purification of the starting material or of the natural material by at least one order of magnitude, preferably 2 or 3 and preferably 4 or 5 orders of magnitude.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes but is not limited to cDNA, genomic DNA, plasmids DNA, synthetic DNA, and semi-synthetic DNA. DNA may be linear, circular, or supercoiled.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester anologs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

The term "fragment" will be understood to mean a nucleotide sequence of reduced length relative to the reference nucleic acid and comprising, over the common portion, a nucleotide sequence identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000 or 1500 consecutive nucleotides of a nucleic acid according to the invention.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "gene" refers to an assembly of nucleotides that encode a polypeptide, and includes cDNA and genomic DNA nucleic acids. "Gene" also refers to a nucleic acid fragment that expresses a specific protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Heterologous" DNA refers to DNA not naturally located in the cell, or in a chromosomal site of the cell. Preferably, the heterologous DNA includes a gene foreign to the cell.

The term "genome" includes chromosomal as well as mitochondrial, chloroplast and viral DNA or RNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989 infra). Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC.

Hybridization requires that the two nucleic acids contain complementary sequences, although depending on the stringency of the hybridization, mismatches between bases are possible. The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as disclosed or used herein as well as those substantially similar nucleic acid sequences.

In a specific embodiment of the invention, polynucleotides are detected by employing hybridization conditions comprising a hybridization step at $T_m$ of 55° C., and utilizing conditions as set forth above. In a preferred embodiment, the $T_m$ is 60° C.; in a more preferred embodiment, the $T_m$ is 63° C.; in an even more preferred embodiment, the $T_m$ is 65° C.

Post-hybridization washes also determine stringency conditions. One set of preferred conditions uses a series of washes starting with 6×SSC, 0.5% SDS at room temperature for 15 minutes (min), then repeated with 2×SSC, 0.5% SDS at 45° C. for 30 minutes, and then repeated twice with 0.2×SSC, 0.5% SDS at 50° C. for 30 minutes. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. Hybridization requires that the two nucleic acids comprise complementary sequences, although depending on the stringency of the hybridization, mismatches between bases are possible.

The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8).

In a specific embodiment of the invention, polynucleotides are detected by employing hybridization conditions comprising a hybridization step in less than 500 mM salt and at least 37 degrees Celsius, and a washing step in 2×SSPE at at least 63 degrees Celsius. In a preferred embodiment, the hybridization conditions comprise less than 200 mM salt and at least 37 degrees Celsius for the hybridization step. In a more preferred embodiment, the hybridization conditions comprise 2×SSPE and 63 degrees Celsius for both the hybridization and washing steps.

In one embodiment, the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "probe" refers to a single-stranded nucleic acid molecule that can base pair with a complementary single stranded target nucleic acid to form a double-stranded molecule.

As used herein, the term "oligonucleotide" refers to a nucleic acid, generally of at least 18 nucleotides, that is hybridizable to a genomic DNA molecule, a cDNA molecule, a plasmid DNA or an mRNA molecule. Oligonucleotides can be labeled, e.g., with $^{32}P$-nucleotides or nucleotides to which a label, such as biotin, has been covalently conjugated. A labeled oligonucleotide can be used as a probe to detect the presence of a nucleic acid. Oligonucleotides (one or both of which may be labeled) can be used as PCR primers, either for cloning full length or a fragment of a nucleic acid, or to detect the presence of a nucleic acid. An oligonucleotide can also be used to form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A "primer" is an oligonucleotide that hybridizes to a target nucleic acid sequence to create a double stranded nucleic acid region that can serve as an initiation point for DNA synthesis under suitable conditions. Such primers may be used in a polymerase chain reaction.

"Polymerase chain reaction" is abbreviated PCR and means an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

"Reverse transcription-polymerase chain reaction" is abbreviated RT-PCR and means an in vitro method for enzymatically producing a target cDNA molecule or molecules from an RNA molecule or molecules, followed by enzymatic amplification of a specific nucleic acid sequence or sequences within the target cDNA molecule or molecules as described above. RT-PCR also provides a means to detect the presence of the target molecule and, under quantitative or semi-quantitative conditions, to determine the relative amount of that target molecule within the starting pool of nucleic acids.

A DNA "coding sequence" is a double-stranded DNA sequence that is transcribed and translated into a polypeptide in a cell in vitro or in vivo when placed under the control of appropriate regulatory sequences. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure. The boundaries of the coding sequence are determined by a start codon at the 5' (amino) terminus and a translation stop codon at the 3' (carboxyl) terminus. A coding sequence can include, but is not limited to, prokaryotic sequences, cDNA from mRNA, genomic DNA sequences, and even synthetic DNA sequences. If the coding sequence is intended for expression in a eukaryotic cell, a polyadenylation signal and transcription termination sequence will usually be located 3' to the coding sequence.

"Open reading frame" is abbreviated ORF and means a length of nucleic acid sequence, either DNA, cDNA or RNA, that comprises a translation start signal or initiation codon, such as an ATG or AUG, and a termination codon and can be potentially translated into a polypeptide sequence.

The term "head-to-head" is used herein to describe the orientation of two polynucleotide sequences in relation to each other. Two polynucleotides are positioned in a head-to-head orientation when the 5' end of the coding strand of one polynucleotide is adjacent to the 5' end of the coding strand of the other polynucleotide, whereby the direction of transcription of each polynucleotide proceeds away from the 5' end of the other polynucleotide. The term "head-to-head" may be abbreviated (5')-to-(5') and may also be indicated by the symbols (←→) or (3'←5'5'→3').

The term "tail-to-tail" is used herein to describe the orientation of two polynucleotide sequences in relation to each other. Two polynucleotides are positioned in a tail-to-tail orientation when the 3' end of the coding strand of one polynucleotide is adjacent to the 3' end of the coding strand of the other polynucleotide, whereby the direction of transcription of each polynucleotide proceeds toward the other polynucleotide. The term "tail-to-tail" may be abbreviated (3')-to-(3') and may also be indicated by the symbols (→←) or (5'→3'3'←5').

The term "head-to-tail" is used herein to describe the orientation of two polynucleotide sequences in relation to each other. Two polynucleotides are positioned in a head-to-tail orientation when the 5' end of the coding strand of one polynucleotide is adjacent to the 3' end of the coding strand of the other polynucleotide, whereby the direction of transcription of each polynucleotide proceeds in the same direction as that of the other polynucleotide. The term "head-to-tail" may be abbreviated (5')-to-(3') and may also be indicated by the symbols (→→) or (5'→3'5'→3').

The term "downstream" refers to a nucleotide sequence that is located 3' to reference nucleotide sequence. In particular, downstream nucleotide sequences generally relate to sequences that follow the starting point of transcription. For example, the translation initiation codon of a gene is located downstream of the start site of transcription.

The term "upstream" refers to a nucleotide sequence that is located 5' to reference nucleotide sequence. In particular, upstream nucleotide sequences generally relate to sequences that are located on the 5' side of a coding sequence or starting point of transcription. For example, most promoters are located upstream of the start site of transcription.

The terms "restriction endonuclease" and "restriction enzyme" refer to an enzyme that binds and cuts within a specific nucleotide sequence within double stranded DNA.

"Homologous recombination" refers to the insertion of a foreign DNA sequence into another DNA molecule, e.g., insertion of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

Several methods known in the art may be used to propagate a polynucleotide according to the invention. Once a suitable host system and growth conditions are established, recombinant expression vectors can be propagated and prepared in quantity. As described herein, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

A "vector" is any means for the cloning of and/or transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication in vivo, i.e., capable of replication under its own control. The term "vector" includes both viral and nonviral means for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as pBR322 or pUC plasmid derivatives, or the Bluescript vector. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used include but are not limited to retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

The term "plasmid" refers to an extra chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "cloning vector" is a "replicon", which is a unit length of a nucleic acid, preferably DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector").

Vectors may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267: 963-967; Wu and Wu, 1988, J. Biol. Chem. 263: 14621-14624; and Hartmut et al., Canadian Patent Application No. 2,012,311, filed Mar. 15, 1990).

A polynucleotide according to the invention can also be introduced in vivo by lipofection. For the past decade, there has been increasing use of liposomes for encapsulation and transfection of nucleic acids in vitro. Synthetic cationic lipids designed to limit the difficulties and dangers encountered with liposome-mediated transfection can be used to prepare liposomes for in vivo transfection of a gene encoding a marker (Felgner et al., 1987, PNAS 84:7413; Mackey, et al., 1988. Proc. Natl. Acad. Sci. U.S.A. 85:8027-8031; and Ulmer et al., 1993, Science 259:1745-1748). The use of cationic lipids may promote encapsulation of negatively charged nucleic acids, and also promote fusion with negatively charged cell membranes (Felgner and Ringold, 1989, Science 337: 387-388). Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey, et al., 1988, supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a vector in vivo as a naked DNA plasmid (see U.S. Pat. Nos. 5,693,622, 5,589,466 and 5,580,859). Receptor-mediated DNA delivery approaches can also be used (Curiel et al., 1992, Hum. Gene Ther. 3: 147-154; and Wu and Wu, 1987, J. Biol. Chem. 262: 4429-4432).

The term "transfection" means the uptake of exogenous or heterologous RNA or DNA by a cell. A cell has been "transfected" by exogenous or heterologous RNA or DNA when such RNA or DNA has been introduced inside the cell. A cell has been "transformed" by exogenous or heterologous RNA or DNA when the transfected RNA or DNA effects a phenotypic change. The transforming RNA or DNA can be integrated (covalently linked) into chromosomal DNA making up the genome of the cell.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The term "genetic region" will refer to a region of a nucleic acid molecule or a nucleotide sequence that comprises a gene encoding a polypeptide.

In addition, the recombinant vector comprising a polynucleotide according to the invention may include one or more origins for replication in the cellular hosts in which their amplification or their expression is sought, markers or selectable markers.

The term "selectable marker" means an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term "reporter gene" means a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), β-glucuronidase (Gus), and the like. Selectable marker genes may also be considered reporter genes.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". Promoters that cause a gene to be expressed in a specific cell type are commonly referred to as "cell-specific promoters" or "tissue-specific promoters". Promoters that cause a gene to be expressed at a specific stage of development or cell differentiation are commonly referred to as "developmentally-specific promoters" or "cell differentiation-specific promoters". Promoters that are induced and cause a gene to be expressed following exposure or treatment of the cell with an agent, biological molecule, chemical, ligand, light, or the like that induces the promoter are commonly referred to as "inducible promoters" or "regulatable promoters". It is further recognized that since in most cases the exact boundaries of regulatory sequences have not been completely defined, DNA fragments of different lengths may have identical promoter activity.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

The term "response element" means one or more cis-acting DNA elements which confer responsiveness on a promoter mediated through interaction with the DNA-binding domains of the first chimeric gene. This DNA element may be either palindromic (perfect or imperfect) in its sequence or composed of sequence motifs or half sites separated by a variable number of nucleotides. The half sites can be similar or identical and arranged as either direct or inverted repeats or as a single half site or multimers of adjacent half sites in tandem. The response element may comprise a minimal promoter isolated from different organisms depending upon the nature of the cell or organism into which the response element will be incorporated. The DNA binding domain of the first hybrid protein binds, in the presence or absence of a ligand, to the DNA sequence of a response element to initiate or suppress transcription of downstream gene(s) under the regulation of this response element. Examples of DNA sequences for response elements of the natural ecdysone receptor include: RRGG/TTCANT-GAC/ACYY (see Cherbas L., et. al., (1991), *Genes Dev.* 5, 120-131); AGGTCAN$_{(n)}$AGGTCA,where N$_{(n)}$ can be one or more spacer nucleotides (see D'Avino PP., et. al., (1995), *Mol. Cell. Endocrinol*, 113, 1-9); and GGGTTGAAT-GAATTT (see Antoniewski C., et. al., (1994). Mol. Cell Biol. 14, 4465-4474).

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from a nucleic acid or polynucleotide. Expression may also refer to translation of mRNA into a protein or polypeptide.

The terms "cassette", "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest, and the cassette and restriction sites are designed to ensure insertion of the cassette in the proper reading frame for transcription and translation. "Transformation cassette" refers to a specific vector comprising a polynucleotide that encodes a polypeptide of interest and having elements in addition to the polynucleotide that facilitate transformation of a particular host cell. Cassettes, expression cassettes, gene expression cassettes and transformation cassettes of the invention may also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

For purposes of this invention, the term "gene switch" refers to the combination of a response element associated with a promoter, and an EcR based system which in the presence of one or more ligands, modulates the expression of a gene into which the response element and promoter are incorporated.

The terms "modulate" and "modulates" mean to induce, reduce or inhibit nucleic acid or gene expression, resulting in the respective induction, reduction or inhibition of protein or polypeptide production.

The plasmids or vectors according to the invention may further comprise at least one promoter suitable for driving expression of a gene in a host cell. The term "expression vector" means a vector, plasmid or vehicle designed to enable the expression of an inserted nucleic acid sequence following transformation into the host. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving these genes is suitable for the present invention including but not limited to: viral promoters, bacterial promoters, animal promoters, mammalian promoters, synthetic promoters, constitutive promoters, tissue specific promoter, developmental specific promoters, inducible promoters, light regulated promoters; CYC1, HIS3, GAL1, GAL4, GAL10, ADH1, PGK, PHO5, GAPDH, ADC1, TRP1, URA3, LEU2, ENO, TPI, alkaline phosphatase promoters (useful for expression in Saccharomyces); AOX1 promoter (useful for expression in Pichia); β-lactamase, lac, ara, tet, trp, lP$_L$, lP$_R$, T7, tac, and trc promoters (useful for expression in *Escherichia coli*); light regulated-, seed specific-, pollen specific-, ovary specific-, pathogenesis or disease related-, cauliflower mosaic virus 35S, CMV 35S minimal, cassava vein mosaic virus (CsVMV), chlorophyll a/b binding protein, ribulose 1, 5-bisphosphate carboxylase, shoot-specific, root specific, chitinase, stress inducible, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells); animal and mammalian promoters known in the art include, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, a baculovirus IE1 promoter, an elongation factor 1 alpha (EF 1) promoter, a phosphoglycerate kinase (PGK) promoter, a ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in liver, alpha 1-antitrypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell α-actin, and the like. In addition, these expression sequences may be modified by addition of enhancer or regulatory sequences and the like.

Enhancers that may be used in embodiments of the invention include but are not limited to: an SV40 enhancer, a cytomegalovirus (CMV) enhancer, an elongation factor 1 (EF1) enhancer, yeast enhancers, viral gene enhancers, and the like.

Termination control regions, i.e., terminator or polyadenylation sequences, may also be derived from various genes native to the preferred hosts. Optionally, a termination site may be unnecessary, however, it is most preferred if included. In a preferred embodiment of the invention, the termination control region may be comprise or be derived from a synthetic sequence, synthetic polyadenylation signal, an SV40 late polyadenylation signal, an SV40 polyadenylation signal, a bovine growth hormone (BGH) polyadenylation signal, viral terminator sequences, or the like.

The terms "3' non-coding sequences" or "3' untranslated region (UTR)" refer to DNA sequences located downstream (3') of a coding sequence and may comprise polyadenylation [poly(A)] recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Regulatory region" means a nucleic acid sequence that regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

A regulatory region from a "heterologous source" is a regulatory region that is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene. The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

A "polypeptide" is a polymeric compound comprised of covalently linked amino acid residues. Amino acids have the following general structure:

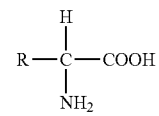

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. A polypeptide of the invention preferably comprises at least about 14 amino acids.

A "protein" is a polypeptide that performs a structural or functional role in a living cell.

An "isolated polypeptide" or "isolated protein" is a polypeptide or protein that is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

A "substitution mutant polypeptide" or a "substitution mutant" will be understood to mean a mutant polypeptide comprising a substitution of at least one (1) wild-type or naturally occurring amino acid with a different amino acid relative to the wild-type or naturally occurring polypeptide. A substitution mutant polypeptide may comprise only one (1) wild-type or naturally occurring amino acid substitution and may be referred to as a "point mutant" or a "single point mutant" polypeptide. Alternatively, a substitution mutant polypeptide may comprise a substitution of two (2) or more wild-type or naturally occurring amino acids with 2 or more amino acids relative to the wild-type or naturally occurring polypeptide. According to the invention, a Group H nuclear receptor ligand binding domain polypeptide comprising a substitution mutation comprises a substitution of at least one (1) wild-type or naturally occurring amino acid with a different amino acid relative to the wild-type or naturally occurring Group H nuclear receptor ligand binding domain polypeptide.

Wherein the substitution mutant polypeptide comprises a substitution of two (2) or more wild-type or naturally occurring amino acids, this substitution may comprise either an equivalent number of wild-type or naturally occurring amino acids deleted for the substitution, i.e., 2 wild-type or naturally occurring amino acids replaced with 2 non-wild-type or non-naturally occurring amino acids, or a non-equivalent number of wild-type amino acids deleted for the substitution, i.e., 2 wild-type amino acids replaced with 1 non-wild-type amino acid (a substitution+deletion mutation), or 2 wild-type amino acids replaced with 3 non-wild-type amino acids (a substitution+insertion mutation).

Substitution mutants may be described using an abbreviated nomenclature system to indicate the amino acid residue and number replaced within the reference polypeptide sequence and the new substituted amino acid residue. For example, a substitution mutant in which the twentieth ($20^{th}$) amino acid residue of a polypeptide is substituted may be abbreviated as "x20z", wherein "x" is the amino acid to be replaced, "20" is the amino acid residue position or number within the polypeptide, and "z" is the new substituted amino acid. Therefore, a substitution mutant abbreviated interchangeably as "E20A" or "Glu20Ala" indicates that the mutant comprises an alanine residue (commonly abbreviated in the art as "A" or "Ala") in place of the glutamic acid (commonly abbreviated in the art as "E" or "Glu") at position 20 of the polypeptide.

A substitution mutation may be made by any technique for mutagenesis known in the art, including but not limited to, in vitro site-directed mutagenesis (Hutchinson, C., et al., 1978, J. Biol. Chem. 253: 6551; Zoller and Smith, 1984, DNA 3: 479-488; Oliphant et al., 1986, Gene 44: 177; Hutchinson et al., 1986, Proc. Natl. Acad. Sci. U.S.A. 83: 710), use of TAB® linkers (Pharmacia), restriction endonuclease digestion/fragment deletion and substitution, PCR-mediated/oligonucleotide-directed mutagenesis, and the like. PCR-based techniques are preferred for site-directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61-70).

"Fragment" of a polypeptide according to the invention will be understood to mean a polypeptide whose amino acid sequence is shorter than that of the reference polypeptide and which comprises, over the entire portion with these reference polypeptides, an identical amino acid sequence. Such fragments may, where appropriate, be included in a larger polypeptide of which they are a part. Such fragments of a polypeptide according to the invention may have a length of at least 2, 3, 4, 5, 6, 8, 10, 13, 14, 15, 16, 17, 18, 19, 20, 21, 22, 25, 26, 30, 35, 40, 45, 50, 100, 200, 240, or 300 amino acids.

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art. A variant polypeptide preferably comprises at least about 14 amino acids.

A "heterologous protein" refers to a protein not naturally produced in the cell.

A "mature protein" refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

The term "signal peptide" refers to an amino terminal polypeptide preceding the secreted mature protein. The signal peptide is cleaved from and is therefore not present in the mature protein. Signal peptides have the function of directing and translocating secreted proteins across cell membranes. Signal peptide is also referred to as signal protein.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

The term "homology" refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667.). Such proteins (and their encoding genes) have sequence homology, as reflected by their high degree of sequence similarity. However, in common usage and in the instant application, the term "homologous," when modified with an adverb such as "highly," may refer to sequence similarity and not a common evolutionary origin.

Accordingly, the term "sequence similarity" in all its grammatical forms refers to the degree of identity or correspondence between nucleic acid or amino acid sequences of proteins that may or may not share a common evolutionary origin (see Reeck et al., 1987, Cell 50: 667).

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Sambrook et al., 1989, supra.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences. Each of the proposed modifications is well within the routine skill in the art, as is determination of retention of biological activity of the encoded products.

Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Substantially similar nucleic acid fragments of the instant invention are those nucleic acid fragments whose DNA sequences are at least 70% identical to the DNA sequence of the nucleic acid fragments reported herein. Preferred substantially nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Even more preferred are nucleic acid fragments that are at least 95% identical to the DNA sequence of the nucleic acid fragments reported herein.

Two amino acid sequences are "substantially homologous" or "substantially similar" when greater than about 40% of the amino acids are identical, or greater than 60% are similar (functionally identical). Preferably, the similar or homologous sequences are identified by alignment using, for example, the GCG (Genetics Computer Group, Program Manual for the GCG Package, *Version* 7, Madison, Wis.) pileup program.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215: 403-410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method may be selected: KTUPLE 1, GAP PENALTY=3, WINDOW=5 and DIAGONALS SAVED=5.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

"Synthetic genes" can be assembled from oligonucleotide building blocks that are chemically synthesized using procedures known to those skilled in the art. These building blocks are ligated and annealed to form gene segments that are then enzymatically assembled to construct the yentire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, two or more individually operable gene regulation systems are said to be "orthogonal" when; a) modulation of each of the given systems by its respective ligand, at a chosen concentration, results in a measurable change in the magnitude of expression of the gene of that system, and b) the change is statistically significantly different than the change in expression of all other systems simultaneously operable in the cell, tissue, or organism, regardless of the simultaneity or sequentially of the actual modulation. Preferably, modulation of each individually operable gene regulation system effects a change in gene expression at least 2-fold greater than all other operable systems in the cell, tissue, or organism. More preferably, the change is at least 5-fold greater. Even more preferably, the change is at least 10-fold greater. Still more preferably, the change is at least 100 fold greater. Even still more preferably, the change is at least 500-fold greater. Ideally, modulation of each of the given systems by its respective ligand at a chosen concentration results in a measurable change in the magnitude of expression of the gene of that system and no measurable change in expression of all other systems operable in the cell, tissue, or organism. In such cases the multiple inducible gene regulation system is said to be "fully orthogonal". The present invention is useful to search for orthogonal ligands and orthogonal receptor-based gene expression systems such as those described in co-pending U.S. application Ser. No. 09/965,697, which is incorporated herein by reference in its entirety.

The term "modulate" means the ability of a given ligand/receptor complex to induce or suppress the transactivation of an exogenous gene.

The term "exogenous gene" means a gene foreign to the subject, that is, a gene which is introduced into the subject through a transformation process, an unmutated version of an endogenous mutated gene or a mutated version of an endogenous unmutated gene. The method of transformation is not critical to this invention and may be any method suitable for the subject known to those in the art. For example, transgenic plants are obtained by regeneration from the transformed cells. Numerous transformation procedures are known from the literature such as agroinfection using *Agrobacterium tumefaciens* or its $T_1$ plasmid, electroporation, microinjection of plant cells and protoplasts, and microprojectile transformation. Complementary techniques are known for transformation of animal cells and regeneration of such transformed cells in transgenic animals. Exogenous genes can be either natural or synthetic genes and therapeutic genes which are introduced into the subject in the form of DNA or RNA which may function through a DNA intermediate such as by reverse transcriptase. Such genes can be introduced into target cells, directly introduced into the subject, or indirectly introduced by the transfer of transformed cells into the subject. The term "therapeutic gene" means a gene which imparts a beneficial function to the host cell in which such gene is expressed. Therapeutic genes are not naturally found in host cells.

The term "ecdysone receptor complex" generally refers to a heterodimeric protein complex consisting of two members of the steroid receptor family, ecdysone receptor ("EcR") and ultraspiracle ("USP") proteins (see Yao, T. P.,et. al. (1993) Nature 366, 476-479; Yao, T.-P.,et. al., (1992) Cell 71, 63-72). The functional ecdysteroid receptor complex may also include additional protein(s) such as immunophilins. Additional members of the steroid receptor family of proteins, known as transcriptional factors (such as DHR38, beta FTZ-1 or other insect homologs), may also be ligand dependent or independent partners for EcR and/or USP. The ecdysone receptor complex can also be a heterodimer of ecdysone receptor protein and the vertebrate homolog of ultraspiracle protein, retinoic acid-X-receptor ("RXR") protein. Homodimer complexes of the ecdysone receptor protein or USP may also be functional under some circumstances.

An ecdysteroid receptor complex can be activated by an active ecdysteroid or non-steroidal ligand bound to one of the proteins of the complex, inclusive of EcR, but not excluding other proteins of the complex.

The ecdysone receptor complex includes proteins which are members of the steroid receptor superfamily wherein all members are characterized by the presence of an amino-terminal transactivation domain, a DNA binding domain ("DBD"), and a ligand binding domain ("LBD") separated by a hinge region. Some members of the family may also have another transactivation domain on the carboxy-terminal side of the LBD. The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins.

The DNA sequences making up the exogenous gene, the response element, and the ecdysone receptor complex may be incorporated into archaebacteria, procaryotic cells such as *Escherichia coli, Bacillus subtilis*, or other enterobacteria, or eucaryotic cells such as plant or animal cells. However, because many of the proteins expressed by the gene are processed incorrectly in bacteria, eucaryotic cells are preferred. The cells may be in the form of single cells or multicellular organisms. The nucleotide sequences for the exogenous gene, the response element, and the receptor complex can also be incorporated as RNA molecules, preferably in the form of functional viral RNAs such as tobacco mosaic virus. Of the eucaryotic cells, vertebrate cells are preferred because they naturally lack the molecules which confer responses to the ligands of this invention for the ecdysone receptor. As a result, they are insensitive to the ligands of this invention. Thus, the ligands of this invention will have negligible physiological or other effects on transformed cells, or the whole organism. Therefore, cells can grow and express the desired product, substantially unaffected by the presence of the ligand itself.

The term "subject" means an intact plant or animal or a cell from a plant or animal. It is also anticipated that the ligands will work equally well when the subject is a fungus or yeast. When the subject is an intact animal, preferably the animal is a vertebrate, most preferably a mammal.

The ligands of the present invention, when used with the ecdysone receptor complex which in turn is bound to the response element linked to an exogenous gene, provide the means for external temporal regulation of expression of the exogenous gene. The order in which the various components bind to each other, that is, ligand to receptor complex and receptor complex to response element, is not critical. Typically, modulation of expression of the exogenous gene is in response to the binding of the ecdysone receptor complex to a specific control, or regulatory, DNA element. The ecdysone receptor protein, like other members of the steroid receptor family, possesses at least three domains, a transactivation domain, a DNA binding domain, and a ligand binding domain. This receptor, like a subset of the steroid receptor family, also possesses less well-defined regions responsible for heterodimerization properties. Binding of the ligand to the ligand binding domain of ecdysone receptor protein, after heterodimerization with USP or RXR protein, enables the DNA binding domains of the heterodimeric proteins to bind to the response element in an activated form, thus resulting in expression or suppression of the exogenous gene. This mechanism does not exclude the potential for ligand binding to either EcR or USP, and the resulting formation of active homodimer complexes (e.g. EcR+EcR or USP+USP). Preferably, one or more of the receptor domains can be varied producing a chimeric gene switch. Typically, one or more of the three domains may be chosen from a source different than the source of the other domains so that the chimeric receptor is optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski, et. al. (1988) Nature, 335, 563-564) or LexA protein from *E. coli* (see Brent and Ptashne (1985), Cell, 43, 729-736) to accommodate chimeric ecdysone receptor complexes. Another advantage of chimeric systems is that they allow choice of a promoter used to drive the exogenous gene according to a desired end result. Such double control can be particularly important in areas of gene therapy, especially when cytotoxic proteins are produced, because both the timing of expression as well as the cells wherein expression occurs can be controlled. The term "promoter" means a specific nucleotide sequence recognized by RNA polymerase. The sequence is the site at which transcription can be specifically initiated under proper conditions. When exogenous genes, operatively linked to a suitable promoter, are introduced into the cells of the subject, expression of the exogenous genes is controlled by the presence of the ligand of this invention. Promoters may be constitutively or inducibly regulated or may be tissue-specific (that is, expressed only in a particular type of cell) or specific to certain developmental stages of the organism.

Another aspect of this invention is a method to modulate the expression of one or more exogenous genes in a subject, comprising administering to the subject an effective amount, that is, the amount required to elicit the desired gene expression or suppression, of a ligand comprising a compound of the present invention and wherein the cells of the subject contain:

a) an ecdysone receptor complex comprising:
   1) a DNA binding domain;
   2) a binding domain for the ligand; and
   3) a transactivation domain; and b) a DNA construct comprising:
   1) the exogenous gene; and
   2) a response element;

wherein the exogenous gene is under the control of the response element; and binding of the DNA binding domain to the response element in the presence of the ligand results in activation or suppression of the gene.

A related aspect of this invention is a method for regulating endogenous or heterologous gene expression in a transgenic subject comprising contacting a ligand comprising a compound of the present invention with an ecdysone receptor within the cells of the subject wherein the cells contain a DNA binding sequence for the ecdysone receptor and wherein formation of an ecdysone receptor-ligand-DNA binding sequence complex induces expression of the gene.

A fourth aspect of the present invention is a method for producing a polypeptide comprising the steps of:
   a) selecting a cell which is substantially insensitive to exposure to a ligand comprising a compound of the present invention;
   b) introducing into the cell:
      1) a DNA construct comprising:
         i) an exogenous gene encoding the polypeptide; and
         ii) a response element;

wherein the gene is under the control of the response element; and
      2) an ecdysone receptor complex comprising:
         i) a DNA binding domain;
         ii) a binding domain for the ligand; and
         iii) a transactivation domain; and
   c) exposing the cell to the ligand.

As well as the advantage of temporally controlling polypeptide production by the cell, this aspect of the invention provides a further advantage, in those cases when accumulation of such a polypeptide can damage the cell, in that expression of the polypeptide may be limited to short periods. Such control is particularly important when the exogenous gene is a therapeutic gene. Therapeutic genes may be called upon to produce polypeptides which control needed functions, such as the production of insulin in diabetic patients. They may also be used to produce damaging or even lethal proteins, such as those lethal to cancer cells. Such control may also be important when the protein levels produced may constitute a metabolic drain on growth or reproduction, such as in transgenic plants.

Numerous genomic and cDNA nucleic acid sequences coding for a variety of polypeptides are well known in the art. Exogenous genetic material useful with the ligands of this invention include genes that encode biologically active proteins of interest, such as, for example, secretory proteins that can be released from a cell; enzymes that can metabolize a substrate from a toxic substance to a non-toxic substance, or from an inactive substance to an active substance; regulatory proteins; cell surface receptors; and the like. Useful genes also include genes that encode blood clotting factors, hormones such as insulin, parathyroid hormone, luteinizing hormone releasing factor, alpha and beta seminal inhibins, and human growth hormone; genes that encode proteins such as enzymes, the absence of which leads to the occurrence of an abnormal state; genes encoding cytokines or lymphokines such as interferons, granulocytic macrophage colony stimulating factor, colony stimulating factor-1, tumor necrosis factor, and erythropoietin; genes encoding inhibitor substances such as alpha$_1$-antitrypsin, genes encoding substances that function as drugs such as diphtheria and cholera toxins; and the like. Useful genes also include those useful for cancer therapies and to treat genetic disorders. Those skilled in the art have access to nucleic acid sequence information for virtually all known genes and can either obtain the nucleic acid molecule directly from a public depository, the institution that published the sequence, or employ routine methods to prepare the molecule.

For gene therapy use, the ligands described herein may be taken up in pharmaceutically acceptable carriers, such as, for example, solutions, suspensions, tablets, capsules, ointments, elixirs, and injectable compositions. Pharmaceutical preparations may contain from 0.01% to 99% by weight of the ligand. Preparations may be either in single or multiple dose forms. The amount of ligand in any particular pharmaceutical preparation will depend upon the effective dose, that is, the dose required to elicit the desired gene expression or suppression.

Suitable routes of administering the pharmaceutical preparations include oral, rectal, topical (including dermal, buccal and sublingual), vaginal, parenteral (including subcutaneous, intramuscular, intravenous, intradermal, intrathecal and epidural) and by naso-gastric tube. It will be understood by those skilled in the art that the preferred route of administration will depend upon the condition being treated and may vary with factors such as the condition of the recipient.

The ligands described herein may also be administered in conjunction with other pharmaceutically active compounds. It will be understood by those skilled in the art that pharmaceutically active compounds to be used in combination with the ligands described herein will be selected in order to avoid adverse effects on the recipient or undesirable interactions between the compounds. Examples of other pharmaceutically active compounds which may be used in combination with the ligands include, for example, AIDS chemotherapeutic agents, amino acid derivatives, analgesics, anesthetics, anorectal products, antacids and antiflatulents, antibiotics, anticoagulants, antidotes, antifibrinolytic agents, antihistamines, anti-inflammatory agents, antineoplastics, antiparasitics, antiprotozoals, antipyretics, antiseptics, antispasmodics and anticholinergics, antivirals, appetite suppressants, arthritis medications, biological response modifiers, bone metabolism regulators, bowel evacuants, cardiovascular agents, central nervous system stimulants, cerebral metabolic enhancers, cerumenolytics, cholinesterase inhibitors, cold and cough preparations, colony stimulating factors, contraceptives, cytoprotective agents, dental preparations, deodorants, dermatologicals, detoxifying agents, diabetes agents, diagnostics, diarrhea medications, dopamine receptor agonists, electrolytes, enzymes and digestants, ergot preparations, fertility agents, fiber supplements, antifungal agents, galactorrhea inhibitors, gastric acid secretion inhibitors, gastrointestinal prokinetic agents, gonadotropin inhibitors, hair growth stimulants, hematinics, hemorrheologic agents, hemostatics, histamine $H_2$ receptor antagonists, hormones, hyperglycemic agents, hypolipidemics, immunosuppressants, laxatives, leprostatics, leukapheresis adjuncts, lung surfactants, migraine preparations, mucolytics, muscle relaxant antagonists, muscle relaxants, narcotic antagonists, nasal sprays, nausea medications nucleoside analogues, nutritional supplements, osteoporosis preparations, oxytocics, parasympatholytics, parasympathomimetics, Parkinsonism drugs, Penicillin adjuvants, phospholipids, platelet inhibitors, porphyria agents, prostaglandin analogues, prostaglandins, proton pump inhibitors, pruritus medications psychotropics, quinolones, respiratory stimulants, saliva stimulants, salt substitutes, sclerosing agents, skin wound preparations, smoking cessation aids, sulfonamides, sympatholytics, thrombolytics, Tourette's syndrome agents, tremor preparations, tuberculosis preparations, uricosuric agents, urinary tract agents, uterine contractants, uterine relaxants, vaginal preparations, vertigo agents, vitamin D analogs, vitamins, and medical imaging contrast media. In some cases the ligands may be useful as an adjunct to drug therapy, for example, to "turn off" a gene that produces an enzyme that metabolizes a particular drug.

For agricultural applications, in addition to the applications described above, the ligands of this invention may also be used to control the expression of pesticidal proteins such as *Bacillus thuringiensis* (Bt) toxin. Such expression may be tissue or plant specific. In addition, particularly when control of plant pests is also needed, one or more pesticides may be combined with the ligands described herein, thereby providing additional advantages and effectiveness, including fewer total applications, than if the pesticides are applied separately. When mixtures with pesticides are employed, the relative proportions of each component in the composition will depend upon the relative efficacy and the desired application rate of each pesticide with respect to the crops, pests, and/or weeds to be treated. Those skilled in the art will recognize that mixtures of pesticides may provide advantages such as a broader spectrum of activity than one pesticide used alone. Examples of pesticides which can be combined in compositions with the ligands described herein include fungicides, herbicides, insecticides, miticides, and microbicides.

The ligands described herein can be applied to plant foliage as aqueous sprays by methods commonly employed, such as conventional high-liter hydraulic sprays, low-liter sprays, air-blast, and aerial sprays. The dilution and rate of application will depend upon the type of equipment employed, the method and frequency of application desired, and the ligand application rate. It may be desirable to include additional adjuvants in the spray tank. Such adjuvants include surfactants, dispersants, spreaders, stickers, antifoam agents, emulsifiers, and other similar materials described in *McCutcheon's Emulsifiers and Detergents, McCutcheon's Emulsifiers and Detergents/Functional Materials*, and *McCutcheon's Functional Materials*, all published annually by McCutcheon Division of MC Publishing Company (New Jersey). The ligands can also be mixed with fertilizers or fertilizing materials before their application. The ligands and solid fertilizing material can also be admixed in mixing or blending equipment, or they can be incorporated with fertilizers in granular formulations. Any relative proportion of fertilizer can be used which is suitable for the crops and weeds to be treated. The ligands described herein will commonly comprise from 5% to 50% of the fertilizing composition. These compositions provide fertilizing materials which promote the rapid growth of desired plants, and at the same time control gene expression.

Host Cells and Non-Human Organisms of the Invention

As described above, ligands for modulating gene expression system of the present invention may be used to modulate gene expression in a host cell. Expression in transgenic host cells may be useful for the expression of various genes of interest. The present invention provides ligands for modulation of gene expression in prokaryotic and eukaryotic host cells. Expression in transgenic host cells is useful for the expression of various polypeptides of interest including but not limited to antigens produced in plants as vaccines, enzymes like alpha-amylase, phytase, glucanes, and xylanse, genes for resistance against insects, nematodes, fungi, bacteria, viruses, and abiotic stresses, antigens, nutraceuticals, pharmaceuticals, vitamins, genes for modifying amino acid content, herbicide resistance, cold, drought, and heat tolerance, industrial products, oils, protein, carbohydrates, antioxidants, male sterile plants, flowers, fuels, other output traits, therapeutic polypeptides, pathway intermediates; for the modulation of pathways already existing in the host for the synthesis of new products heretofore not possible using the host; cell based assays; functional genomics assays, biotherapeutic protein production, proteomics assays, and the like. Additionally the gene products may be useful for conferring higher growth yields of the host or for enabling an alternative growth mode to be utilized.

Thus, the present invention provides ligands for modulating gene expression in an isolated host cell according to the invention. The host cell may be a bacterial cell, a fungal cell, a nematode cell, an insect cell, a fish cell, a plant cell, an avian cell, an animal cell, or a mammalian cell. In still another embodiment, the invention relates to ligands for modulating gene expression in an host cell, wherein the method comprises culturing the host cell as described above in culture medium under conditions permitting expression of a polynucleotide encoding the nuclear receptor ligand binding domain comprising a substitution mutation, and isolating the nuclear receptor ligand binding domain comprising a substitution mutation from the culture.

In a specific embodiment, the isolated host cell is a prokaryotic host cell or a eukaryotic host cell. In another specific embodiment, the isolated host cell is an invertebrate host cell or a vertebrate host cell. Preferably, the host cell is selected from the group consisting of a bacterial cell, a fungal cell, a yeast cell, a nematode cell, an insect cell, a fish cell, a plant cell, an avian cell, an animal cell, and a mammalian cell. More preferably, the host cell is a yeast cell, a nematode cell, an insect cell, a plant cell, a zebrafish cell, a chicken cell, a hamster cell, a mouse cell, a rat cell, a rabbit cell, a cat cell, a dog cell, a bovine cell, a goat cell, a cow cell, a pig cell, a horse cell, a sheep cell, a simian cell, a monkey cell, a chimpanzee cell, or a human cell. Examples of preferred host cells include, but are not limited to, fungal or yeast species such as *Aspergillus, Trichoderma, Saccharomyces, Pichia, Candida, Hansenula*, or bacterial species such as those in the genera *Synechocystis, Synechococcus, Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium* and *Klebsiella*; plant species selected from the group consisting of an apple, *Arabidopsis*, bajra, banana, barley, beans, beet, blackgram, chickpea, chili, cucumber, eggplant, favabean, maize, melon, millet, mungbean, oat, okra, *Panicum*, papaya, peanut, pea, pepper, pigeonpea, pineapple, *Phaseolus*, potato, pumpkin, rice, sorghum, soybean, squash, sugarcane, sugarbeet, sunflower, sweet potato, tea, tomato, tobacco, watermelon, and wheat; animal; and mammalian host cells.

In a specific embodiment, the host cell is a yeast cell selected from the group consisting of a *Saccharomyces*, a *Pichia*, and a *Candida* host cell.

In another specific embodiment, the host cell is a *Caenorhabdus elegans* nematode cell.

In another specific embodiment, the host cell is an insect cell.

In another specific embodiment, the host cell is a plant cell selected from the group consisting of an apple, *Arabidopsis*, bajra, banana, barley, beans, beet, blackgram, chickpea, chili, cucumber, eggplant, favabean, maize, melon, millet, mungbean, oat, okra, *Panicum*, papaya, peanut, pea, pepper, pigeonpea, pineapple, *Phaseolus*, potato, pumpkin, rice, sorghum, soybean, squash, sugarcane, sugarbeet, sunflower, sweet potato, tea, tomato, tobacco, watermelon, and wheat cell.

In another specific embodiment, the host cell is a zebrafish cell.

In another specific embodiment, the host cell is a chicken cell.

In another specific embodiment, the host cell is a mammalian cell selected from the group consisting of a hamster cell, a mouse cell, a rat cell, a rabbit cell, a cat cell, a dog cell, a bovine cell, a goat cell, a cow cell, a pig cell, a horse cell, a sheep cell, a monkey cell, a chimpanzee cell, and a human cell.

Host cell transformation is well known in the art and may be achieved by a variety of methods including but not limited to electroporation, viral infection, plasmid/vector transfection, non-viral vector mediated transfection, *Agrobacterium*-mediated transformation, particle bombardment, and the like. Expression of desired gene products involves culturing the transformed host cells under suitable conditions and inducing expression of the transformed gene. Culture conditions and gene expression protocols in prokaryotic and eukaryotic cells are well known in the art (see General Methods section of Examples). Cells may be harvested and the gene products isolated according to protocols specific for the gene product.

In addition, a host cell may be chosen which modulates the expression of the inserted polynucleotide, or modifies and processes the polypeptide product in the specific fashion desired. Different host cells have characteristic and specific mechanisms for the translational and post-translational processing and modification [e.g., glycosylation, cleavage (e.g., of signal sequence)] of proteins. Appropriate cell lines or host systems can be chosen to ensure the desired modification and processing of the foreign protein expressed. For example, expression in a bacterial system can be used to produce a non-glycosylated core protein product. However, a polypeptide expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, the polypeptide's activity. Furthermore, different vector/host expression systems may affect processing reactions, such as proteolytic cleavages, to a different extent. The present invention also relates to a non-human organism comprising an isolated host cell according to the invention. In a specific embodiment, the non-human organism is a prokaryotic organism or a eukaryotic organism. In another specific embodiment, the non-human organism is an invertebrate organism or a vertebrate organism.

Preferably, the non-human organism is selected from the group consisting of a bacterium, a fungus, a yeast, a nematode, an insect, a fish, a plant, a bird, an animal, and a mammal. More preferably, the non-human organism is a yeast, a nematode, an insect, a plant, a zebrafish, a chicken, a hamster, a mouse, a rat, a rabbit, a cat, a dog, a bovine, a goat, a cow, a pig, a horse, a sheep, a simian, a monkey, or a chimpanzee.

In a specific embodiment, the non-human organism is a yeast selected from the group consisting of Saccharomyces, Pichia, and Candida.

In another specific embodiment, the non-human organism is a Caenorhabdus *elegans* nematode.

In another specific embodiment, the non-human organism is a plant selected from the group consisting of an apple,

*Arabidopsis*, bajra, banana, barley, beans, beet, blackgram, chickpea, chili, cucumber, eggplant, favabean, maize, melon, millet, mungbean, oat, okra, *Panicum*, papaya, peanut, pea, pepper, pigeonpea, pineapple, *Phaseolus*, potato, pumpkin, rice, sorghum, soybean, squash, sugarcane, sugarbeet, sunflower, sweet potato, tea, tomato, tobacco, watermelon, and wheat.

In another specific embodiment, the non-human organism is a *Mus musculus* mouse.

Gene Expression Modulation System of the Invention

The present invention relates to a group of ligands that are useful in an ecdysone receptor-based inducible gene expression system. As presented herein, a novel group of ligands provides an improved inducible gene expression system in both prokaryotic and eukaryotic host cells. Thus, the present invention relates to ligands that are useful to modulate expression of genes. In particular, the present invention relates to ligands having the ability to transactivate a gene expression modulation system comprising at least one gene expression cassette that is capable of being expressed in a host cell comprising a polynucleotide that encodes a polypeptide comprising a Group H nuclear receptor ligand binding domain. Preferably, the Group H nuclear receptor ligand binding is from an ecdysone receptor, a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a farnesol receptor. More preferably, the Group H nuclear receptor ligand binding domain is from an ecdysone receptor.

In a specific embodiment, the gene expression modulation system comprises a gene expression cassette comprising a polynucleotide that encodes a polypeptide comprising a transactivation domain, a DNA-binding domain that recognizes a response element associated with a gene whose expression is to be modulated; and a Group H nuclear receptor ligand binding domain comprising a substitution mutation. The gene expression modulation system may further comprise a second gene expression cassette comprising: i) a response element recognized by the DNA-binding domain of the encoded polypeptide of the first gene expression cassette; ii) a promoter that is activated by the transactivation domain of the encoded polypeptide of the first gene expression cassette; and iii) a gene whose expression is to be modulated.

In another specific embodiment, the gene expression modulation system comprises a gene expression cassette comprising a) a polynucleotide that encodes a polypeptide comprising a transactivation domain, a DNA-binding domain that recognizes a response element associated with a gene whose expression is to be modulated; and a Group H nuclear receptor ligand binding domain comprising a substitution mutation, and b) a second nuclear receptor ligand binding domain selected from the group consisting of a vertebrate retinoid X receptor ligand binding domain, an invertebrate retinoid X receptor ligand binding domain, an ultraspiracle protein ligand binding domain, and a chimeric ligand binding domain comprising two polypeptide fragments, wherein the first polypeptide fragment is from a vertebrate retinoid X receptor ligand binding domain, an invertebrate retinoid X receptor ligand binding domain, or an ultraspiracle protein ligand binding domain, and the second polypeptide fragment is from a different vertebrate retinoid X receptor ligand binding domain, invertebrate retinoid X receptor ligand binding domain, or ultraspiracle protein ligand binding domain. The gene expression modulation system may further comprise a second gene expression cassette comprising: i) a response element recognized by the DNA-binding domain of the encoded polypeptide of the first gene expression cassette; ii) a promoter that is activated by the transactivation domain of the encoded polypeptide of the first gene expression cassette; and iii) a gene whose expression is to be modulated.

In another specific embodiment, the gene expression modulation system comprises a first gene expression cassette comprising a polynucleotide that encodes a first polypeptide comprising a DNA-binding domain that recognizes a response element associated with a gene whose expression is to be modulated and a nuclear receptor ligand binding domain, and a second gene expression cassette comprising a polynucleotide that encodes a second polypeptide comprising a transactivation domain and a nuclear receptor ligand binding domain, wherein one of the nuclear receptor ligand binding domains is a Group H nuclear receptor ligand binding domain comprising a substitution mutation. In a preferred embodiment, the first polypeptide is substantially free of a transactivation domain and the second polypeptide is substantially free of a DNA binding domain. For purposes of the invention, "substantially free" means that the protein in question does not contain a sufficient sequence of the domain in question to provide activation or binding activity. The gene expression modulation system may further comprise a third gene expression cassette comprising: i) a response element recognized by the DNA-binding domain of the first polypeptide of the first gene expression cassette; ii) a promoter that is activated by the transactivation domain of the second polypeptide of the second gene expression cassette; and iii) a gene whose expression is to be modulated.

Wherein when only one nuclear receptor ligand binding domain is a Group H ligand binding domain comprising a substitution mutation, the other nuclear receptor ligand binding domain may be from any other nuclear receptor that forms a dimer with the Group H ligand binding domain comprising the substitution mutation. For example, when the Group H nuclear receptor ligand binding domain comprising a substitution mutation is an ecdysone receptor ligand binding domain comprising a substitution mutation, the other nuclear receptor ligand binding domain ("partner") may be from an ecdysone receptor, a vertebrate retinoid X receptor (RXR), an invertebrate RXR, an ultraspiracle protein (USP), or a chimeric nuclear receptor comprising at least two different nuclear receptor ligand binding domain polypeptide fragments selected from the group consisting of a vertebrate RXR, an invertebrate RXR, and a USP (see co-pending application Ser. Nos. PCT/US01/09050, PCT/US02/05235, and PCT/US02/05706, incorporated herein by reference in their entirety). The "partner" nuclear receptor ligand binding domain may further comprise a truncation mutation, a deletion mutation, a substitution mutation, or another modification.

Preferably, the vertebrate RXR ligand binding domain is from a human *Homo sapiens*, mouse *Mus musculus*, rat *Rattus norvegicus*, chicken *Gallus gallus*, pig *Sus scrofa domestica*, frog *Xenopus laevis*, zebrafish *Danio rerio*, tunicate *Polyandrocarpa misakiensis*, or jellyfish *Tripedalia cysophora* RXR.

Preferably, the invertebrate RXR ligand binding domain is from a locust *Locusta migratoria* ultraspiracle polypeptide ("LmUSP"), an ixodid tick *Amblyomma americanum* RXR homolog 1 ("AmaRXR1"), a ixodid tick *Amblyomma americanum* RXR homolog 2 ("AmaRXR2"), a fiddler crab

*Celuca pugilator* RXR homolog ("CpRXR"), a beetle *Tenebrio molitor* RXR homolog ("TmRXR"), a honeybee *Apis mellifera* RXR homolog ("AmRXR"), an aphid *Myzus persicae* RXR homolog ("MpRXR"), or a non-Dipteran/non-Lepidopteran RXR homolog.

Preferably, the chimeric RXR ligand binding domain comprises at least two polypeptide fragments selected from the group consisting of a vertebrate species RXR polypeptide fragment, an invertebrate species RXR polypeptide fragment, and a non-Dipteran/non-Lepidopteran invertebrate species RXR homolog polypeptide fragment. A chimeric RXR ligand binding domain for use in the present invention may comprise at least two different species RXR polypeptide fragments, or when the species is the same, the two or more polypeptide fragments may be from two or more different isoforms of the species RXR polypeptide fragment.

In a preferred embodiment, the chimeric RXR ligand binding domain comprises at least one vertebrate species RXR polypeptide fragment and one invertebrate species RXR polypeptide fragment.

In a more preferred embodiment, the chimeric RXR ligand binding domain comprises at least one vertebrate species RXR polypeptide fragment and one non-Dipteran/non-Lepidopteran invertebrate species RXR homolog polypeptide fragment.

In a specific embodiment, the gene whose expression is to be modulated is a homologous gene with respect to the host cell. In another specific embodiment, the gene whose expression is to be modulated is a heterologous gene with respect to the host cell.

The ligands for use in the present invention as described below, when combined with the ligand binding domain of the nuclear receptor(s), which in turn are bound to the response element linked to a gene, provide the means for external temporal regulation of expression of the gene. The binding mechanism or the order in which the various components of this invention bind to each other, that is, for example, ligand to ligand binding domain, DNA-binding domain to response element, transactivation domain to promoter, etc., is not critical.

In a specific example, binding of the ligand to the ligand binding domain of a Group H nuclear receptor and its nuclear receptor ligand binding domain partner enables expression or suppression of the gene. This mechanism does not exclude the potential for ligand binding to the Group H nuclear receptor (GHNR) or its partner, and the resulting formation of active homodimer complexes (e.g. GHNR+GHNR or partner+partner). Preferably, one or more of the receptor domains is varied producing a hybrid gene switch. Typically, one or more of the three domains, DBD, LBD, and transactivation domain, may be chosen from a source different than the source of the other domains so that the hybrid genes and the resulting hybrid proteins are optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski, et al. (1988) Nature, 335: 563-564) or LexA protein from *Escherichia coli* (see Brent and Ptashne (1985), Cell, 43: 729-736), or synthetic response elements specific for targeted interactions with proteins designed, modified, and selected for such specific interactions (see, for example, Kim, et al. (1997), *Proc. Natl. Acad. Sci., USA*, 94: 3616-3620) to accommodate hybrid receptors. Another advantage of two-hybrid systems is that they allow choice of a promoter used to drive the gene expression according to a desired end result. Such double control can be particularly important in areas of gene therapy, especially when cytotoxic proteins are produced, because both the timing of expression as well as the cells wherein expression occurs can be controlled. When genes, operably linked to a suitable promoter, are introduced into the cells of the subject, expression of the exogenous genes is controlled by the presence of the system of this invention. Promoters may be constitutively or inducibly regulated or may be tissue-specific (that is, expressed only in a particular type of cells) or specific to certain developmental stages of the organism.

The ecdysone receptor is a member of the nuclear receptor superfamily and classified into subfamily 1, group H (referred to herein as "Group H nuclear receptors"). The members of each group share 40-60% amino acid identity in the E (ligand binding) domain (Laudet et al., A Unified Nomenclature System for the Nuclear Receptor Subfamily, 1999; Cell 97: 161-163). In addition to the ecdysone receptor, other members of this nuclear receptor subfamily 1, group H include: ubiquitous receptor (UR), orphan receptor 1 (OR-1), steroid hormone nuclear receptor 1 (NER-1), retinoid X receptor interacting protein -15 (RIP-15), liver X receptor β (LXRβ), steroid hormone receptor like protein (RLD-1), liver X receptor (LXR), liver X receptor α (LXRα), farnesoid X receptor (FXR), receptor interacting protein 14 (RIP-14), and farnesol receptor (HRR-1

In particular, described herein are novel ligands useful in a gene expression modulation system comprising a Group H nuclear receptor ligand binding domain comprising a substitution mutation. This gene expression system may be a "single switch"-based gene expression system in which the transactivation domain, DNA-binding domain and ligand binding domain are on one encoded polypeptide. Alternatively, the gene expression modulation system may be a "dual switch"- or "two-hybrid"-based gene expression modulation system in which the transactivation domain and DNA-binding domain are located on two different encoded polypeptides.

An ecdysone receptor-based gene expression modulation system of the present invention may be either heterodimeric or homodimeric. A functional EcR complex generally refers to a heterodimeric protein complex consisting of two members of the steroid receptor family, an ecdysone receptor protein obtained from various insects, and an ultraspiracle (USP) protein or the vertebrate homolog of USP, retinoid X receptor protein (see Yao, et al. (1993) Nature 366, 476-479; Yao, et al., (1992) Cell 71, 63-72). However, the complex may also be a homodimer as detailed below. The functional ecdysteroid receptor complex may also include additional protein(s) such as immunophilins. Additional members of the steroid receptor family of proteins, known as transcriptional factors (such as DHR38 or betaFTZ-1), may also be ligand dependent or independent partners for EcR, USP, and/or RXR. Additionally, other cofactors may be required such as proteins generally known as coactivators (also termed adapters or mediators). These proteins do not bind sequence-specifically to DNA and are not involved in basal transcription. They may exert their effect on transcription activation through various mechanisms, including stimulation of DNA-binding of activators, by affecting chromatin structure, or by mediating activator-initiation complex interactions. Examples of such coactivators include RIP140, TIF1, RAP46/Bag-1, ARA70, SRC-1/NCoA-1, TIF2/GRIP/NCoA-2, ACTR/AIB1/RAC3/pCIP as well as the promiscuous coactivator C response element B binding protein, CBP/p300 (for review see Glass et al., Curr. Opin. Cell Biol. 9:222-232, 1997). Also, protein cofactors generally known as corepressors (also known as repressors, silencers, or silencing mediators) may be required to effectively inhibit transcriptional activation in the absence of ligand. These corepressors may interact with the unliganded ecdysone receptor to silence the activity at the response element. Current evidence suggests that the binding of ligand changes the conformation of the receptor, which results in release of the corepressor and recruitment of the above described coactivators, thereby abolishing their silencing activity. Examples of corepressors include N-CoR and SMRT (for review, see Horwitz et al. Mol Endocrinol. 10: 1167-1177, 1996). These cofactors may either be endogenous within the cell or organism, or may be added exogenously as transgenes to be expressed in either a regulated or unregulated fashion. Homodimer complexes of the ecdysone receptor protein, USP, or RXR may also be functional under some circumstances.

The ecdysone receptor complex typically includes proteins that are members of the nuclear receptor superfamily wherein all members are generally characterized by the presence of an amino-terminal transactivation domain, a DNA binding domain ("DBD"), and a ligand binding domain ("LBD") separated from the DBD by a hinge region. As used herein, the term "DNA binding domain" comprises a minimal polypeptide sequence of a DNA binding protein, up to the entire length of a DNA binding protein, so long as the DNA binding domain functions to associate with a particular response element. Members of the nuclear receptor superfamily are also characterized by the presence of four or five domains: A/B, C, D, E, and in some members F (see U.S. Pat. No. 4,981,784 and Evans, Science 240:889-895 (1988)). The "A/B" domain corresponds to the transactivation domain, "C" corresponds to the DNA binding domain, "D" corresponds to the hinge region, and "E" corresponds to the ligand binding domain. Some members of the family may also have another transactivation domain on the carboxy-terminal side of the LBD corresponding to "F".

The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins. The EcR receptor, like a subset of the steroid receptor family, also possesses less well-defined regions responsible for heterodimerization properties. Because the domains of nuclear receptors are modular in nature, the LBD, DBD, and transactivation domains may be interchanged.

Gene switch systems are known that incorporate components from the ecdysone receptor complex. However, in these known systems, whenever EcR is used it is associated with native or modified DNA binding domains and transactivation domains on the same molecule. USP or RXR are typically used as silent partners. It has previously been shown that when DNA binding domains and transactivation domains are on the same molecule the background activity in the absence of ligand is high and that such activity is dramatically reduced when DNA binding domains and transactivation domains are on different molecules, that is, on each of two partners of a heterodimeric or homodimeric complex (see PCT/US01/09050).

Method of Modulating Gene Expression of the Invention

The present invention also relates to methods of modulating gene expression in a host cell using a gene expression modulation system according to the invention. Specifically, the present invention provides a method of modulating the expression of a gene in a host cell comprising the steps of: a) introducing into the host cell a gene expression modulation system according to the invention; and b) introducing into the host cell a ligand; wherein the gene to be modulated is a component of a gene expression cassette comprising: i) a response element comprising a domain recognized by the DNA binding domain of the gene expression system; ii) a promoter that is activated by the transactivation domain of the gene expression system; and iii) a gene whose expression is to be modulated, whereby upon introduction of the ligand into the host cell, expression of the gene is modulated.

The invention also provides a method of modulating the expression of a gene in a host cell comprising the steps of: a) introducing into the host cell a gene expression modulation system according to the invention; b) introducing into the host cell a gene expression cassette according to the invention, wherein the gene expression cassette comprises i) a response element comprising a domain recognized by the DNA binding domain from the gene expression system; ii) a promoter that is activated by the transactivation domain of the gene expression system; and iii) a gene whose expression is to be modulated; and c) introducing into the host cell a ligand; whereby upon introduction of the ligand into the host cell, expression of the gene is modulated.

The present invention also provides a method of modulating the expression of a gene in a host cell comprising a gene expression cassette comprising a response element comprising a domain to which the DNA binding domain from the first hybrid polypeptide of the gene expression modulation system binds; a promoter that is activated by the transactivation domain of the second hybrid polypeptide of the gene expression modulation system; and a gene whose expression is to be modulated; wherein the method comprises the steps of: a) introducing into the host cell a gene expression modulation system according to the invention; and b) introducing into the host cell a ligand; whereby upon introduction of the ligand into the host, expression of the gene is modulated.

Genes of interest for expression in a host cell using methods disclosed herein may be endogenous genes or heterologous genes. Nucleic acid or amino acid sequence information for a desired gene or protein can be located in one of many public access databases, for example, GENBANK, EMBL, Swiss-Prot, and PIR, or in many biology related journal publications. Thus, those skilled in the art have access to nucleic acid sequence information for virtually all known genes. Such information can then be used to construct the desired constructs for the insertion of the gene of interest within the gene expression cassettes used in the methods described herein.

Examples of genes of interest for expression in a host cell using methods set forth herein include, but are not limited to: antigens produced in plants as vaccines, enzymes like alpha-amylase, phytase, glucanes, and xylanse, genes for resistance against insects, nematodes, fungi, bacteria, viruses, and abiotic stresses, nutraceuticals, pharmaceuticals, vitamins, genes for modifying amino acid content, herbicide resistance, cold, drought, and heat tolerance, industrial products, oils, protein, carbohydrates, antioxidants, male sterile plants, flowers, fuels, other output traits, genes encoding therapeutically desirable polypeptides or products that may be used to treat a condition, a disease, a disorder, a dysfunction, a genetic defect, such as monoclonal antibodies, enzymes, proteases, cytokines, interferons, insulin, erthropoietin, clotting factors, other blood factors or components, viral vectors for gene therapy, virus for vaccines, targets for drug discovery, functional genomics, and proteomics analyses and applications, and the like.

Measurion Gene Expression/Transcription

One useful measurement of the methods of the invention is that of the transcriptional state of the cell including the identities and abundances of RNA, preferably mRNA species. Such measurements are conveniently conducted by measuring cDNA abundances by any of several existing gene expression technologies.

Nucleic acid array technology is a useful technique for determining differential mRNA expression. Such technology includes, for example, oligonucleotide chips and DNA microarrays. These techniques rely on DNA fragments or oligonucleotides which correspond to different getnes or cDNAs which are immobilized on a solid support and hybridized to probes prepared from total mRNA pools extracted from cells, tissues, or whole organisms and converted to cDNA. Oligonucleotide chips are arrays of oligonucleotides synthesized on a substrate using photolithographic techniques. Chips have been produced which can analyze for up to 1700 genes. DNA microarrays are arrays of DNA samples, typically PCR products, that are robotically printed onto a microscope slide. Each gene is analyzed by a full or partial-length target DNA sequence. Microarrays with up to 10,000 genes are now routinely prepared commercially. The primary difference between these two techniques is that oligonucleotide chips typically utilize 25-mer oligonucleotides which allow fractionation of short DNA molecules whereas the larger DNA targets of microarrays, approximately 1000 base pairs, may provide more sensitivity in fractionating complex DNA mixtures.

Another useful measurement of the methods of the invention is that of determining the translation state of the cell by measuring the abundances of the constituent protein species present in the cell using processes well known in the art.

Where identification of genes associated with various physiological functions is desired, an assay may be employed in which changes in such functions as cell growth, apoptosis, senescence, differentiation, adhesion, binding to a specific molecules, binding to another cell, cellular organization, organogenesis, intracellular transport, transport facilitation, energy conversion, metabolism, myogenesis, neurogenesis, and/or hematopoiesis is measured.

In addition, selectable marker or reporter gene expression may be used to measure gene expression modulation using the present invention.

Other methods to detect the products of gene expression are well known in the art and include Southern blots (DNA detection), dot or slot blots (DNA, RNA), northern blots (RNA), RT-PCR (RNA), western blots (polypeptide detection), and ELISA (polypeptide) analyses. Although less preferred, labeled proteins can be used to detect a particular nucleic acid sequence to which it hybidizes.

In some cases it is necessary to amplify the amount of a nucleic acid sequence. This may be carried out using one or more of a number of suitable methods including, for example, polymerase chain reaction ("PCR"), ligase chain reaction ("LCR"), strand displacement amplification ("SDA"), transcription-based amplification, and the like. PCR is carried out in accordance with known techniques in which, for example, a nucleic acid sample is treated in the presence of a heat stable DNA polymerase, under hybridizing conditions, with one pair of oligonucleotide primers, with one primer hybridizing to one strand (template) of the specific sequence to be detected. The primers are sufficiently complementary to each template strand of the specific sequence to hybridize therewith. An extension product of each primer is synthesized and is complementary to the nucleic acid template strand to which it hybridized. The extension product synthesized from each primer can also serve as a template for further synthesis of extension products using the same primers. Following a sufficient number of rounds of synthesis of extension products, the sample may be analyzed as described above to assess whether the sequence or sequences to be detected are present.

The present invention may be better understood by reference to the following non-limiting Examples, which are provided as exemplary of the invention.

EXAMPLES

General Methods

Standard recombinant DNA and molecular cloning techniques used herein are well known in the art and are described by Sambrook, J., Fritsch, E. F. and Maniatis, T. *Molecular Cloning: A Laboratory Manual*; Cold Spring Harbor Laboratory Press: Cold Spring Harbor, N.Y. (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of host cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences may be accomplished using the suite of programs available from the Genetics Computer Group Inc. (Wisconsin Package Version 9.0, Genetics Computer Group (GCG), Madison, Wis.). Where the GCG program "Pileup" is used the gap creation default value of 12, and the gap extension default value of 4 may be used. Where the CGC "Gap" or "Bestfit" program is used the default gap creation penalty of 50 and the default gap extension penalty of 3 may be used. In any case where GCG program parameters are not prompted for, in these or any other GCG program, default values may be used.

The meaning of abbreviations is as follows: "h" means hour(s), "min" means minute(s), "sec" means second(s), "d" means day(s), "µL" means microliter(s), "mL" means milliliter(s), "L" means liter(s), "µM" means micromolar, "mM" means millimolar, "M" means molar, "mmol" means millimoles, "µg" means microgram(s), "mg" means milligram(s), "A" means adenine or adenosine, "T" means thymine or thymidine, "G" means guanine or guanosine, "C"

means cytidine or cytosine, "x g" means times gravity, "nt" means nucleotide(s), "aa" means amino acid(s), "bp" means base pair(s), "kb" means kilobase(s), "k" means kilo, "μ" means micro, "° C." means degrees Celsius, "C" in the context of a chemical equation means Celsius, "THF" means tetrahydrofuran, "DME" means dimethoxyethane, "DMF" means dimethylformamide, "NMR" means nuclear magnetic resonance, "psi" refers to pounds per square inch, and "TLC" means thin layer chromatography.

Example 1

Preparation of Compounds

The compounds of the present invention may be made according to the following synthesis routes.

1.1 Preparation of Isopropylidene-hydrazine

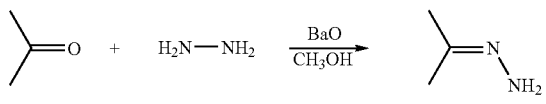

A 500 mL 3-neck flask was fitted with a mechanical stirrer, thermometer, and addition funnel. The vessel was charged with 140 mL of methanol, and then cooled to −5° C. in an ice/salt bath. BaO (7.5 g, 50 mmole) was then added portion-wise over 5 minutes. Gas evolution and an exotherm were observed. A maximum temperature of 5° C. was reached. The reaction was cooled down to 0° C., and hydrazine monohydrate (32 g, 0.64 moles) was added in one portion, causing the mixture to warm to 5° C. The vessel was cooled down to 0° C. and the mixture was stirred for 10 minutes. A solution of acetone (37 g, 0.64 moles) in 40 mL of methanol was added drop-wise over 1 hour at 5° C. Stirring was continued, allowing the reaction to warm slowly to room temperature. Stirring was continued overnight, but if the reaction was allowed to proceed for only one hour, quite satisfactory yields were obtained. $^1$H NMR indicated the absence of acetone and a complete reaction. Ether (300 mL) was added, which caused more solid to precipitate. Celite 545 and MgSO$_4$ were added, the mixture was filtered through a bed of Celite on S&S sharkskin paper in a sintered glass funnel, and most of the ether was removed at or below room temperature on a rotary evaporator. The solution was then gently distilled. The distillate was placed in a clean flask and the remaining methanol was removed by rotovap evaporation without application of heat. The process was monitored by $^1$H NMR until <2.5% methanol remained. Isopropylidene-hydrazine was obtained as a slightly cloudy colorless liquid (41 g, 89%), and used as such in subsequent reactions. $^1$H NMR (300 MHz, CDCl3)δ(ppm): 4.85 (br, 2H), 1.93 (s, 3H), 1.77 (s, 3H).

1.2 Preparation of Sec-butylidene-hydrazine

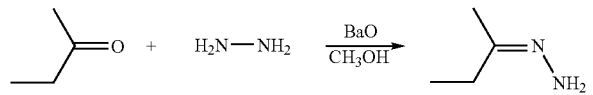

A 1 L flask equipped with a mechanical stirrer, thermometer, and addition funnel was charged with 250 mL of methanol and cooled to 0° C. Barium oxide (15.3 g, 100 mmol) was added portion-wise with exotherm. The reaction was cooled to 0° C., and hydrazine monohydrate (64.1 g, 1.28 mol) was slowly added. The reaction mixture was stirred for 10 minutes, after which methylethylketone (92.3 g, 1.28 mol) was added drop-wise over a 30 minute period. The reaction was then stirred for 1 hour, maintaining a temperature below 8° C. $^1$H NMR indicated the absence of ketone and a complete reaction. Ether (200 mL) was then added, and the BaO was filtered through a bed of silica gel. The resultant clear filtrate was liberated of methanol on a rotary evaporator at or below room temperature, the receptacle was changed, and the product hydrazone was distilled using a water bath set at 38° C. After discarding a small forerun and residue, 70 g of sec-butylidene-hydrazine were obtained as a clear colorless liquid. The material was stored under refrigeration. $^1$H NMR (300 MHz, CDCl3)δ(ppm): 4.9 (br, 2H), 2.25 (q, 2H), 1.78 (s, 3H), 1.07 (t, 3H). Angew. Chemie, 94, 2, 133 (1982).

1.3 Preparation of Cyclopentylidene-hydrazine

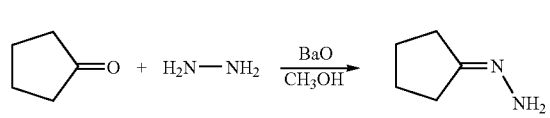

Cyclopentylidene-hydrazine was prepared in an analogous manner in 61% yield. The material was stored under refrigeration. $^1$H NMR (300 MHz, CDCl3)δ(ppm): 4.9 (br, 2H), 2.35 (t, 2H), 2.2 (t, 2H), 1.9 (m, 2H), 1.78 (mn, 3H), 1.07 (t, 3H).

1.4 Preparation of (tetrahydro-pyran-4-ylidene)-hydrazine

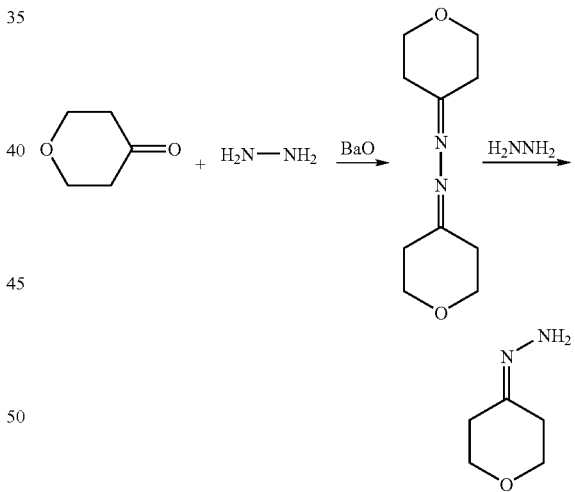

Tetrahydro-4H-pyran4-one (10 g, 0.1 mol) and methanol (150 mL) were charged to a 500 mL three-necked flask fitted with an addition funnel. The vessel was cooled in an ice bath and kept under a nitrogen atmosphere while a solution of hydrazine (2.5 g, 50 mol) in 50 mL of methanol was added drop-wise over a period of one hour. A white precipitate formed after about half of the hydrazine was added. Stirring was continued overnight, and subsequent TLC indicated one product. The methanol was removed in vacuo, and the residue was slurried in hexane and filtered to yield 9.1 g (46.4 mol) N,N'-bis-(tetrahydro-pyran-4-ylidene)-hydrazine as a white solid. $^1$H NMR (300 MHz, CDCl3)δ(ppm): 3.88 (t, 2H), 3.77 (t, 2H), 2.67 (t, 2H), 2.50 (t, 2H).

This material was charged along with hydrazine (1.6 g, 50 mol) to a 300 mL flask fitted with a magnetic stirrer and reflux condensor containing 100 mL of absolute ethanol, which had been freshly dried by azeotropic distillation with the aid of a Dean-Stark trap. The reaction mixture was heated at reflux for 6 hours at which time $^1$H NMR analysis indicated only a trace of azine. The reaction mixture was cooled and the solvent removed on a rotary evaporator at 35° C. (Higher temperatures accelerate reversion to the azine). The remaining ethanol was eliminated by repeated addition of carbon tetrachloride, followed by removal in vacuo. Tetrahydro-pyran-4-ylidene-hydrazine containing about 5-10% azine could be isolated in this manner. Upon standing at room temperature, the hydrazone disproportionates to the azine in a matter of days. $^1$H NMR (300 MHz, CDCl3)δ (ppm): 5.0 (br, 2H), 3.80 (m, 4H), 2.39 (m, 4H).

1.5 Preparation of Indan-2-ylidene-hydrazine

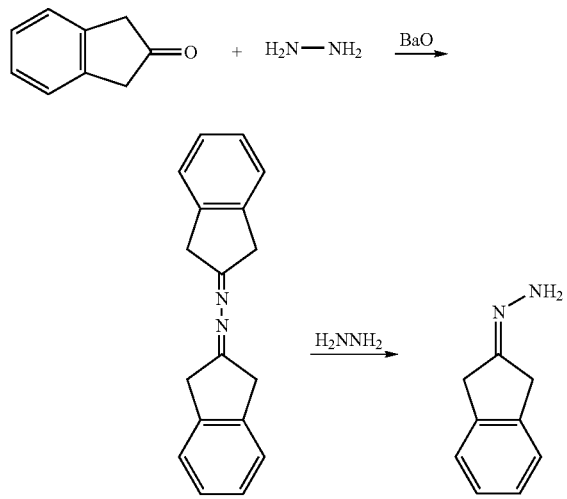

Indan-2-one (25 g) and methanol (25 mL) were charged to a 500 mL 3-neck flask with an addition funnel and magnetic stirrer under an atmosphere of nitrogen. A solution of hydrazine monohydrate (4.73 g) in 50 mL of methanol was added drop-wise over one hour at room temperature. Stirring was continued overnight. The resultant precipitate (ca. 15.5 g) was collected, and shaken with a water/chloroform mixture. The chloroform layer was dried, and the solvent was removed in vacuo to give a reddish-white solid. The original supernatant contained more of the intended N,N'-di-indan-2-ylidene-hydrazine. $^1$H NMR (300 MHz, CDCl3)δ(ppm): 7.4 (m, 1H), 7.3 (m, 3H), 3.93 (s, 2H), 3.82 (s, 2H).

The intermediate azine (15.35 g) was dissolved in 200 mL of absolute ethanol in a 500 mL round bottom flask. Approximately 50 mL of the solvent was distilled off, after which a solution of 1.9 g anhydrous hydrazine in ethanol was added. The reaction was heated at reflux for 90 minutes, at which time the starting azine compound could no longer be detected by 'H NMR. Indan-2-ylidene-hydrazine was isolated as a brown solid. $^1$H NMR (300 MHz, CDCl3) δ (ppm): 7.3 (m, 4H), 5.05 (br s, 2H), 3.76 (s, 2H), 3.58 (s, 2H). The purity of commercial indan-2-one may be particularly critical for the success of this reaction.

1.6 Preparation of (1-methyl-piperidin-4-ylidene)-hydrazine

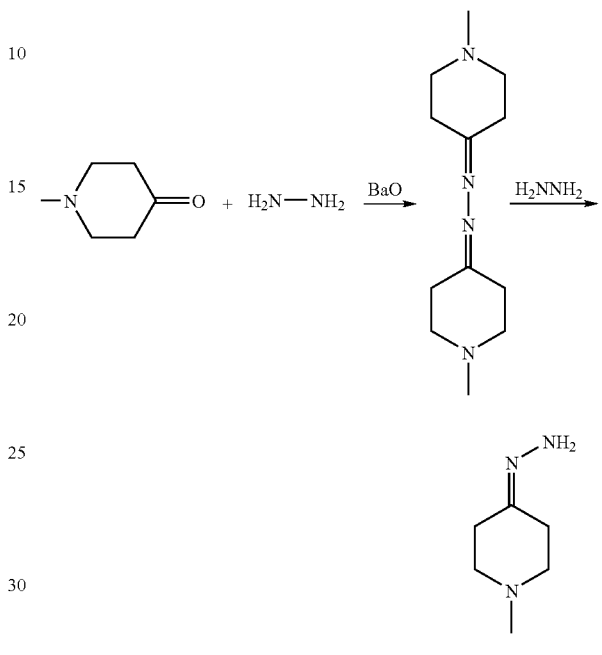

1-Methyl-piperidin-4-one (22.6 g, 0.2 mol) and methanol (200 mL) were charged to a 500 mL three-necked flask fitted with an addition funnel. The vessel was cooled in an ice bath and kept under a nitrogen atmosphere while a solution of hydrazine monohydrate (5 g, 0.1 mol) in 50 mL of methanol was added drop-wise over a period of one hour. A white precipitate formed after about half of the hydrazine was added. Stirring was continued overnight, and subsequent TLC indicated one product. The methanol was removed in vacuo, and the residue was slurried in hexane and filtered to provide N,N'-bis-(1-methyl-piperidin-4-ylidene)-hydrazine. $^1$H NMR (300 MHz, CDCl3)δ(ppm): 2.6 (m, 8H), 2.5 (m, 8H), 2.33 (s, 6H).

This material was charged along with anhydrous hydrazine (5.2 g, 0.162 mol) to a 500 mL flask fitted with a magnetic stirrer and reflux condensor containing 200 mL of absolute ethanol, which had been freshly dried by azeotropic distillation with the aid of a Dean-Stark trap. The clear yellow reaction mixture was heated at reflux for 4 hours at which time $^1$H NMR analysis indicated a small amount of azine. An additional 2 g of hydrazine was added and heating was continued for an additional 4 hours. The reaction mixture was cooled and the solvent was removed on a rotary evaporator. (Higher temperatures accelerate reversion to the azine). The remaining ethanol was eliminated by repeated addition of carbon tetrachloride followed by removal in vacuo. (1-Methyl-piperidin-4-ylidene)-hydrazine was obtained as a yellow oil in a 12.5 g quantity, containing about 5% azine. $^1$H NMR (300 MHz, CDCl3)δ(ppm): 5.0 (br, 2H), 2.5 (m, 4H), 2.4 (m, 4H), 2.33 (s, 6H).

1.7 Preparation of Benzylidene-hydrazine

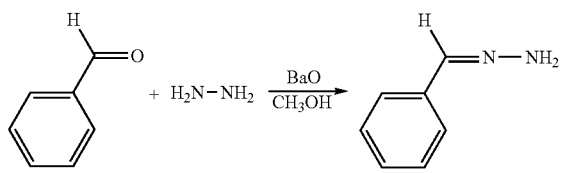

A 1 L flask equipped with a mechanical stirrer, thermometer, and addition funnel was charged with 250 mL of methanol and cooled to 0° C. Barium oxide (9.8 g, 64 mmol) was added portion-wise with exotherm. The reaction was cooled to 0° C., and hydrazine monohydrate (64.1 g, 1.28 mol) was slowly added. The reaction mixture was stirred for 10 minutes, after which time benzaldehyde (135.8 g, 1.28 mol) was added drop-wise over a 30 minute period. The reaction was then stirred for 1 hour, while maintaining a temperature below 8° C. $^1$H NMR indicated the absence of ketone and a complete reaction. Ether (200 mL) was added, and the BaO was filtered through a bed of silica gel. The resultant clear filtrate was liberated of methanol on a rotary evaporator at or below room temperature. A large mass of bright yellow solid azine ($^1$H-NMR (300 MHz, CDCl3)δ (ppm): 8.67 (s, 2H), 7.85 (m, 4H), 7.47 (m, 6H)), was removed by filtration, and the filtrate was distilled to provide ca. 12 g of distillate benzylidene-hydrazine. The material was stored under refrigeration. $^1$H-NMR (300 MHz, CDCl3) δ(ppm): 7.74 (s, 1H), 7.53 (m, 2H), 7.35 (m, 3H), 5.5 (br, 2H).

1.8 Preparation of (1-Phenyl-ethylidene)-hydrazine

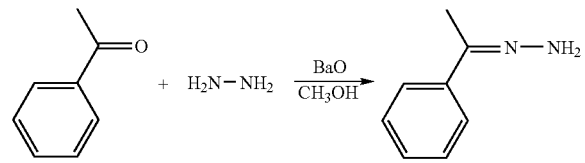

A 1 L flask equipped with a mechanical stirrer, thermometer, and addition funnel was charged with 300 mL of methanol and cooled to 0° C. Barium oxide (8.4 g, 55 mmol) was added portion-wise with exotherm. The reaction was cooled again to 0° C., and hydrazine monohydrate (54.6 g, 1.09 mol) was slowly added. The reaction mixture was stirred for 10 minutes, after which benzaldehyde (131.5 g, 1.09 mol) was added drop-wise over a 30 minute period. The reaction was then stirred for 1 hour, while maintaining a temperature below 8° C. $^1$H NMR indicated the absence of ketone and a complete reaction. Ether (200 mL) was added, and the BaO was filtered through a bed of silica gel. The resultant clear filtrate was liberated of methanol on a rotary evaporator at or below room temperature. The remaining concentrate was distilled at ca. 1 torr and the intended (1-phenyl-ethylidene)-hydrazine was collected at 91-94° C. in a 50 g quantity. $^1$H-NMR (300 MHz, CDCl3)δ(ppm): 7.65 (m, 2H), 7.35 (m, 3H), 5.37 (br, 2H), 2.13 (s, 3H). During the distillation, a bright yellow solid of N,N'-bis-(1-phenyl-ethylidene)-hydrazine appeared in the distillation vessel. $^1$H-NMR (300 MHz, CDCl3)δ(ppm): 7.95 (m, 4H), 7.45 (m, 6H), 2.32 (s, 6H).

1.9 Preparation of (2,2,2-Trifluoro-1-methyl-ethylidene)-hydrazine

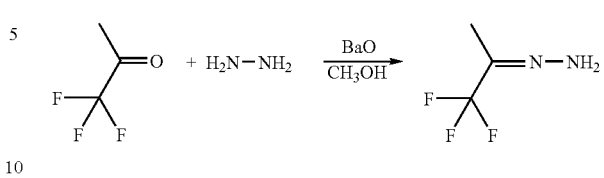

Hydrazine monohydrate (69 g, 1.37 mol) was charged to a 300 mL single-neck flask fitted with a magnetic stirrer and addition funnel. The vessel was cooled in an ice bath, as trifluoroacetone (77 g, 0.687 moles) was added drop-wise over a period of hours. The reaction mixture was stirred for an additional hour and extracted several times with ether. The solvent was removed from the combined ether extracts, providing about 50 g of a waxy solid. This material was distilled at atmospheric pressure, yielding ca. 13 g of (2,2,2-trifluoro-1-methyl-ethylidene)-hydrazine as a clear colorless distillate. $^1$H-NMR (300 MHz, CDCl3)δ(ppm): 5.7 (br, 2H), 1.87 (s, 3H); b.p. 135° C.

1.10 Preparation of 3,5-Dimethyl-benzaldehyde Oxime

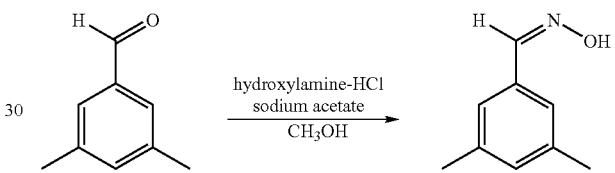

A 2 L round bottom flask was set up with a mechanical stirrer, thermometer, N$_2$ inlet and reflux condensor. A solution of 3,5-dimethyl-benzaldehyde (70 g. 522 mmol) in 300 mL of methanol was added, followed by the addition of sodium acetate (44 g, 536 mmol). Hydroxylamine-HCl (37 g, 532 mmol) was added portion-wise over 5 minutes, during which time the maximum temperature reached without cooling was 27° C. The mixture was stirred for an additional 2 hours at room temperature. TLC (10% ethyl acetate in hexane) indicated the absence of the starting aldehyde and the appearance of oxime. Most of the methanol was removed on a rotary evaporator, resulting in the formation of a precipitate. Ether and water were added to the concentrated suspension, and then the ether layer was collected, dried over MgSO$_4$, and removed on a rotary evaporator. The white crystalline material was air-dried, resulting in 77 g (100%) of 3,5-dimethyl-benzaldehyde oxime. $^1$H-NMR (300 MHz, CDCl$_3$)δ(ppm): 8.09 (s, 1H), 7.22 (s, 2H), 7.05 (s, 1H), 2.33 (s, 6H).

1.11 Preparation of Benzohydroximoyl Chloride

Method A:

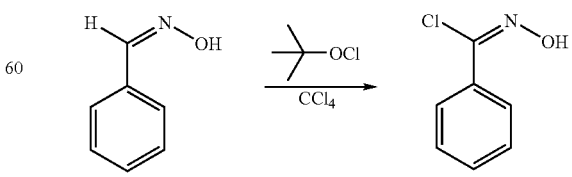

A 125 mL round bottom flask was fitted with a magnetic stirrer, thermometer, and pressure-equalized addition funnel.

Benzaldehyde oxime (25 g, 0.206 mole) dissolved in 40 mL of $CCl_4$ was charged to the vessel. The reaction was protected from bright light as a solution of t-butyl hypochlorite (12.1 g, prepared by the action of NaOCl on t-butyl alcohol according to Organic Syntheses, Volume 5, p. 183) in 20 mL of $CCl_4$ was added drop-wise over a period of 40 minutes. A transient exotherm and aqua color developed. Stirring was continued overnight at room temperature, after which time most of the $CCl_4$ from the yellow reaction mixture was removed in vacuo. Pentane was added and the solution was chilled, causing crystal formation of the intended hydroximoyl chloride at a yield of 9.0 g. $^1$H-NMR (200 MHz, $CDCl_3$)δ(ppm): 8.4(s, 1H, N—OH), 7.87 (m, 2H), 7.45 (m, 3H).

Method B:

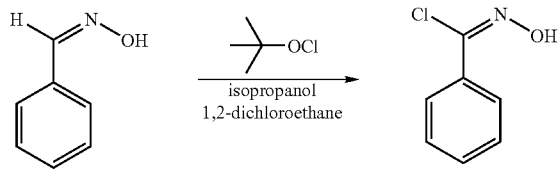

A 100 mL 3-neck round bottom flask, equipped with a magnetic stirrer and thermometer, was charged with 40 mL of dichloroethane, 1.06 g of benzaldehyde oxime, and 10 mL of isopropanol. The vessel was cooled to −12° C. in an ice salt bath. T-butyl hypochlorite was added (optionally as a solution in dichloroethane) drop-wise over several minutes with rapid stirring, while maintaining the temperature below 10° C. A flash of blue color was observed for several seconds. The mixture was stirred for 15 minutes with continued chilling. The solvent and by-product t-butyl alcohol were removed on a rotary evaporator and chased several times with chloroform. After the third chase, a powder formed, which was washed again with chloroform, resulting in crystal formation of 1.32 g of the product. TLC indicated a single spot which eluted slightly higher than the starting oxime, Rf=0.4; Rf(oxime)=0.32 (4:1 hexane:ethyl acetate). The product benzohydroximoyl chloride was stored in the freezer. $^1$H-NMR (300 MHz, $CDCl_3$)δ(ppm): 8.63(s, 1H, N—OH), 7.87 (m, 2H), 7.45 (m, 3H).

Caution: T-butylhypochlorite is odoriforous and a severe lachyrmator. The benzohydroximoyl chloride may not be thermally stable, therefore handle with a non-metal spatula, protect from strong light, and store in the freezer. McGillivray, G.; ten Krooden, E.; S. Africa J. Chem. 986, 39(1).

The following additional hydroximoyl chlorides were prepared by Method B:

3,5-dimethylbenzohydroximoyl chloride: a white solid after crystallization from cold pentane, pentane/$CHCl_3$ or heptane. $^1$H-NMR (300 MHz, $CDCl_3$)δ(ppm): 8.4 (br, 1H), 7.45 (s, 2H), 7.12 (s, 1H), 2.35 (s, 6H).

4-Phenylbenzohydroximoyl chloride: 87% yield. $^1$H-NMR (300 MHz, $CDCl_3$)δ(ppm): 7.95 (d, 2H), 7.65 (m, 4H), 7.37-7.5 (m, 3H), 1.65 (br s, 1H).

4-Chlorobenzohydroximoyl chloride: flocculent solid, 100% yield. $^1$H-NMR (300 MHz, $CDCl_3$)δ(ppm): 7.8 (d, 2H), 7.4 (d, 2H), 1.7 (br s, 1H). Rf (1:1 hexane:ethyl acetate)=0.63.

4-Trifluoromethoxybenzohydroximoyl chloride: 98% yield. $^1$H-NMR (300 MHz, $CDCl_3$)δ(ppm): 7.95 (s, 1H, N—OH), 7.3 (d, 2H).

3-Trifluoromethylbenzohydroximoyl chloride: 99% yield. $^1$H-NMR (300 MHz, $CDCl_3$)δ(ppm): 8.12 (s, 1H), 8.11 (s, 1H), 8.08 (d, 1H), 7.72 (d, 1H), 7.55 (t, 1H).

2-Methoxybenzohydroximoyl chloride: 99% yield. $^1$H-NMR (300 MHz, $CDCl_3$)δ(ppm): 9.6 (s, 1H), 7.6 (d, 1H), 7.34 (t, 1H), 7.0 (m, 2H), 3.9 (s, 3H). Rf (1:1 hexane:ethyl acetate)=0.5.

2,3-[1,3]Dioxole-benzohydroximoyl chloride. $^1$H-NMR (300 MHz, $CDCl_3$)δ(ppm): 7.95 (br s, 1H, N—OH), 7.4 (d, 1H), 7.3 (s, 1H), 6.85 (d, 1H), 6.05 (s, 2H).

2,4-Dimethoxybenzohydroximoyl chloride. $^1$H-NMR (300 MHz, $CDCl_3$)δ(ppm): 7.55 (d, 1H), 6.5 (d, 1H), 6.45 (s, 1H), 3.96 (s, 3H).

3-Nitrobenzohydroximoyl chloride: 100%yield. $^1$H-NMR (300 MHz, $CDCl_3$)δ(ppm): 8.71 (s, 1H, N—OH), 8.45 (s, 1H), 8.30 (d, 1H), 8.19 (d, 1H), 7.65 (t, 1H). Rf (1:1 hexane:ethyl acetate)=0.5.

1.12 Preparation of aryl-[1,2,4]oxadiazol-4-ylamines

Method A-1

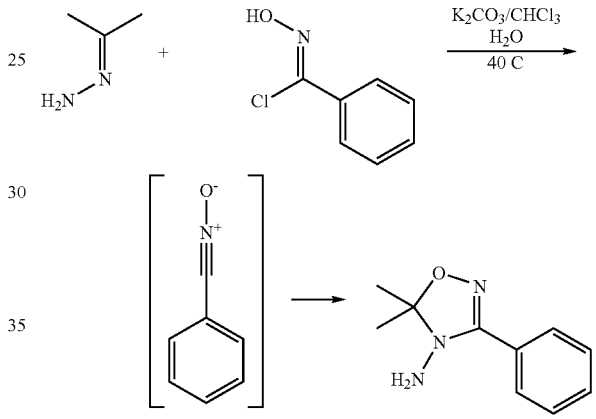

A solution of isopropylidene-hydrazine (0.59 g, 8 mmol) in 15 mL of chloroform and an aqueous solution of $K_2CO_3$ (0.5 g in 3 mL of water) were mixed and cooled in a 50 mL round-bottom flask chilled with ice water. A solution of benzohydroximoyl chloride (0.51 g, 3.2 mmol) in 10 mL of chloroform was added slowly with vigorous magnetic stirring. The ice batch was replaced with a 40° C. water bath and the mixture was stirred at 40° C. for 2 hours and then monitored by TLC (1:1 ethyl acetate:hexanes). When progression of the reaction began to significantly decelerate, the mixture was worked up by the addition of 10 mL of water and 60 mL of chloroform or methylene chloride. The organic layer was removed in a separatory funnel, dried over $MgSO_4$, and the solvent removed on a rotary evaporator to yield a semi-solid. The crude product was triturated with 2% ether in hexanes (30 mL), by magnetic stirring in a round bottom flask or manipulating the material with a spatula. Filtration and air-drying provided 5,5-dimethyl-3-phenyl-[1,2,4]oxadiazol-4-ylamine in ca. 40% yield. $^1$H-NMR (300 MHz, $CDCl_3$)δ(ppm): 7.77 (m, 2H), 7.48 (m, 3H), 3.4 (br), 1.55 (s, 6H).

The following additional oxadiazolines were prepared by method A-1:

3-(4-Chloro-phenyl)-5,5-dimethyl-[1,2,4]oxadiazol-4-ylamine: 52% yield, trituratio pentane. $^1$H-NMR (300 MHz, $CDCl_3$)δ(ppm): 7.72 (d, 2H), 7.42 (d, 2H), 3.5 (s, 1H), 1.6 (s, 1H), 1.54 (s, 6H). Rf=0.46 (1:1 ethyl acetate:hexane).

3-Benzo[1,3]dioxol-5-yl-5,5-dimethyl-[1,2,4]oxadiazol-4-ylamine: 35% yield, trituration from 10% ether in hexane or ethyl acetate/hexane gradient silica gel chromatography. $^1$H-NMR (300 MHz, CDCl$_3$)δ(ppm): 7.22 (s, 1H), 7.87 (s, 1H), 7.85 (s, 1H), 6.0 (s, 2H), 3.5 (br s, 2H), 1.52 (s, 6H).

3-(2-Methoxy-phenyl)-5,5-dimethyl-[1,2,4]oxadiazol-4-ylamine. $^1$H-NMR (300 MHz, CDCl$_3$)δ(ppm): 7.5 (d, 2H), 7.05 (m, 2H), 3.91 (s, 3H), 3.7 (br s, 2H), 1.54 (s, 6H). Ethyl acetate/hexane gradient silica gel chromatography, Rf=0.25 (1:1 ethyl acetate:hexane).

3-(3-Trifluoromethyl-phenyl)-5,5-dimethyl-[1,2,4]oxadiazol4-ylamine: trituration from heptane, 47% yield. $^1$H-NMR (300 MHz, CDCl$_3$)δ(ppm): 8.1 (s, 1H), 7.95 (d, 1H), 7.7 (d, 1H), 7.55 (t, 1H), 3.5 (br s, 2H), 1.57 (s, 6H).

3-(4-Trifluoromethoxy-phenyl)-5,5-dimethyl-[1,2,4]oxadiazol-4-ylamine: trituration heptane, 28% yield. $^1$H-NMR (300 MHz, CDCl$_3$)δ(ppm): 7.85 (d, 2H), 7.3 (d, 2H), 3.55 (br s, 2H), 1.55 (s, 6H). Ethyl acetate/hexane gradient silica gel chromatography.

3-Biphenyl-4-yl-5,5-dimethyl-[1,2,4]oxadiazol-4-ylamine: trituration from pentane, 49% yield. $^1$H-NMR (300 MHz, CDCl$_3$)δ(ppm): 7.85 (d, 2H), 7.65 (m, 4H), 7.5 (t, 2H), 3.6 (br s, 1.57 (s, 6H).

3-(2,4-Dimethoxy-phenyl)-5,5-dimethyl-[1,2,4]oxadiazol-4-ylamine: ethyl acetate/hexane gradient silica gel chromatography, trituration from 2:3 ether:hexane, Rf=0.14 (1:1 ethyl acetate:hexane). $^1$H-NMR (300 MHz, CDCl$_3$)δ(ppm): 7.48 (s, 1H), 7.3 (s, 1H), 6.58 (s, 1H), 3.96 (s, 3H), 3.92 (s, 3H), 3.65 (br s, 2H), 1.52 (s, 6H).

3-(2,4-Dichloro-phenyl)-5,5-dimethyl-[1,2,4]oxadiazol-4-ylamine. $^1$H-NMR (300 MHz, CDCl$_3$)δ(ppm): 7.5 (s, 1H), 7.45 (d, 1H), 7.35 (d, 1H), 3.53 (s, 2H), 1.57 (s, 6H).

Method A-2

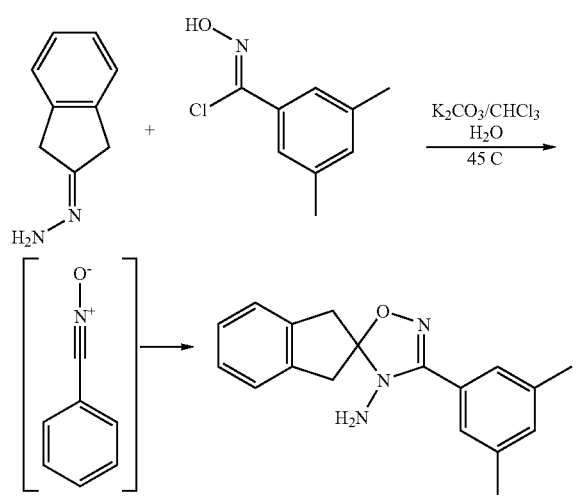

A mixture of indan-2-ylidene-hydrazine (250 mg) and 3,5-dimethyl-benzaldehyde chlorooxime (314 mg) were mixed with CHCl$_3$ (10 mL) and aqueous K$_2$CO$_3$ (6 mL, 0.167 g/mL) at 45° C. for a period of 4 hours. The phases of the reaction mixture were diluted and partitioned, and the organic layer was dried and the solvent was evaporated in vacuo. Column chromatography of the crude product on silica gel using 10% ethyl acetate in hexane yielded 0.52 g of 3-(3,5-dimethyl-phenyl)-7,8-benzo-1-oxa-2,4-diaza-spiro[4.4]non-2-en-4-ylamine. An analytical sample was crystallized from CHCl$_3$/pentane. $^1$H NMR (CDCl$_3$, 300 MHz)δ (ppm): 7.37 (s, 2H), 7.22 (m, 4H), 7.11 (s, 1H), 3.6 (d, 2H), 3.57 (br s, 2H), 3.32 (d, 2H), 2.36 (s, 6H).

Method B

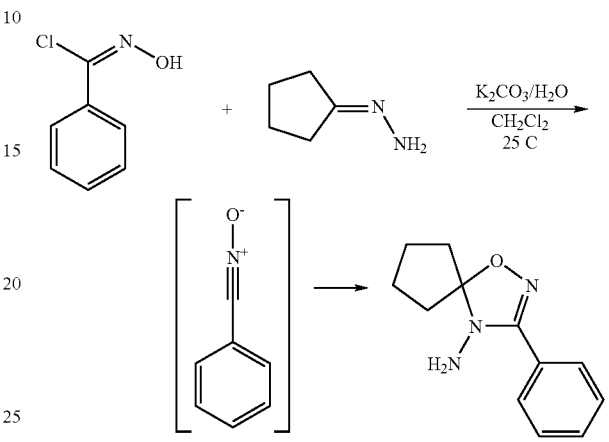

A round bottom flask was charged with a solution of 20 g of K$_2$CO$_3$ in 50 mL of water and cooled in an ice bath. Cyclopentylidene-hydrazine (7.9 g, 80 mmol) in 25 mL of CH$_2$Cl$_2$ was added, followed by a drop-wise addition of benzohydroximoyl chloride (5 g, 0.032 mmol) in 25 mL of CH$_2$Cl$_2$ over a period of 15 minutes. The mixture was stirred for several days, and allowed to warm to room temperature. Water (50 mL) and CH$_2$Cl$_2$ (50 mL) were added and the phases were separated. The organic layer was washed twice with 50 mL of water, dried over MgSO$_4$, and filtered. The solvent was removed in vacuo, leaving 9 g of a waxy solid. Crystallization from ethyl acetate/hexane provided 3.5 g (50%) of 3-phenyl-1-oxa-2,4-diaza-spiro[4.4]non-2-en4-ylamine after drying. $^1$H-NMR (300 MHz, CDCl$_3$)δ(ppm): 7.72 ((m, 2H), 7.46 (m, 3H), 3.54 (s, 2H), 2.1 (m, 2H), 1.85 (m, 2H), 1.8 (m., 2H).

The following additional oxadiazolines were prepared by method B:

3-(3,5-Dimethyl-phenyl)-5-ethyl-5-methyl-[1,2,4]oxadiazol4-ylamine: crystals from hexanes, 9% yield. $^1$H-NMR (300 MHz, CDCl$_3$)δ(ppm): 7.31 ((s, 2H), 7.1 (s, 1H), 3.5 (s, 2H), 2.35 (s, 6H), 1.85 (m, 2H), 1.48 (s, 3H), 1.03 (t, 3H).

3-(3,5-Dimethyl-phenyl)-1-oxa-2,4-diaza-spiro[4.4]non-2-en-4-ylamine: crystals from ethyl acetate, 20% yield. $^1$H-NMR (300 MHz, CDCl$_3$)δ(ppm): 7.32 ((s, 2H), 7.1 (s, 1H), 3.55 (s, 2H), 2.35 (s, 6H), 2.1 (m, 2H), 2.0 (m, 2H), 1.85 (m, 2H), 1.8 (m., 2H).

3-(3,5-Dimethyl-phenyl)-1,8-dioxa-2,4-diaza-spiro[4.5]dec-2-en4-ylamine: crystals. $^1$H-NMR (300 MHz, CDCl$_3$)δ (ppm): 7.34 (s, 2H), 7.15 (s, 1H), 4.0 (m, 2H), 3.87 (dt, 2H), 3.55 (br s, 2H), 2.36 (s, 6H), 2.1 (m, 2H), 1.9 (br d, 2H).

3-Phenyl-1,8-dioxa-2,4-diaza-spiro[4.5]dec-2-en4-ylamine: crystals from CHCl$_3$/hexane after silica gel chromatography (0-15% ethyl acetate in hexanes), m.p. 168-9 C$_1$Rf=0.5 (1:1 ethyl acetate:hexanes). $^1$H-NMR (300 MHz, CDCl$_3$)δ(ppm): 7.86 (m, 2H), 7.157 (m, 3H), 3.92 (m, 2H), 3.87 (dt, 2H), 3.61 (br s, 2H), 2.1 (m, 2H), 1.85 (br d, 2H).

Method C

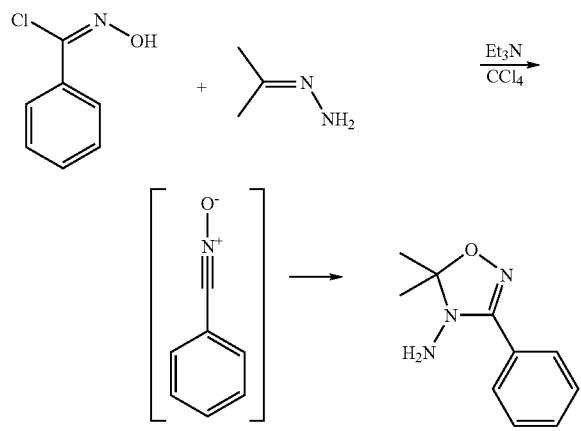

A solution of benzohydroximoyl chloride in CCl$_4$, was added drop-wise over 15 minutes to a solution of isopropy- lidene-hydrazine (3.6 g, 50 mmoles) and triethylamine (3.0 g, 50 mmoles) in 10 mL of CHCl$_3$. Stirring was continued for 2 hours while the mixture was allowed to warm to room temperature. TLC indicated that the reaction was complete. The reaction mixture was washed three times with water, dried over MgSO$_4$, and filtered. The solvent was removed in vacuo, and the product, 5,5-Dimethyl-3-phenyl-[1,2,4]oxa-diazol-4-ylamine, was recrystallized from CHCl$_3$/hexane, resulting in 1.2 g at a yield of 20.9%. $^1$H-NMR (300 MHz, CDCl$_3$)δ(ppm): 7.79 (m, 2H), 7.5 (m, 3H), 3.55 (s, 2H), 1.55 (s, 6H). Use of high quality hydroximoyl chloride and addition at 0° C. resulted in improved yields (40%).

The following additional oxadiazoline was prepared by method C:

3-(3,5-Dimethyl-phenyl)-5,5-dimethyl-[1,2,4]oxadiazol-4-ylamine: purification by ethyl acetate/hexane gradient silica gel chromatography (Rf=0.5 2:1 hexane:ethyl acetate), or crystallization from ether/heptane. $^1$H-NMR (300 MHz, CDCl$_3$)δ(ppm): 7.32 (s, 2H), 7.12 (s, 1H), 3.52 (s, 2H), 2.35 (s, 6H), 1.53 (s, 6H).

TABLE 1

Optimization of [3 + 2] cycloaddition of benzonitrile N-oxide and isopropylidene-hydrazine.

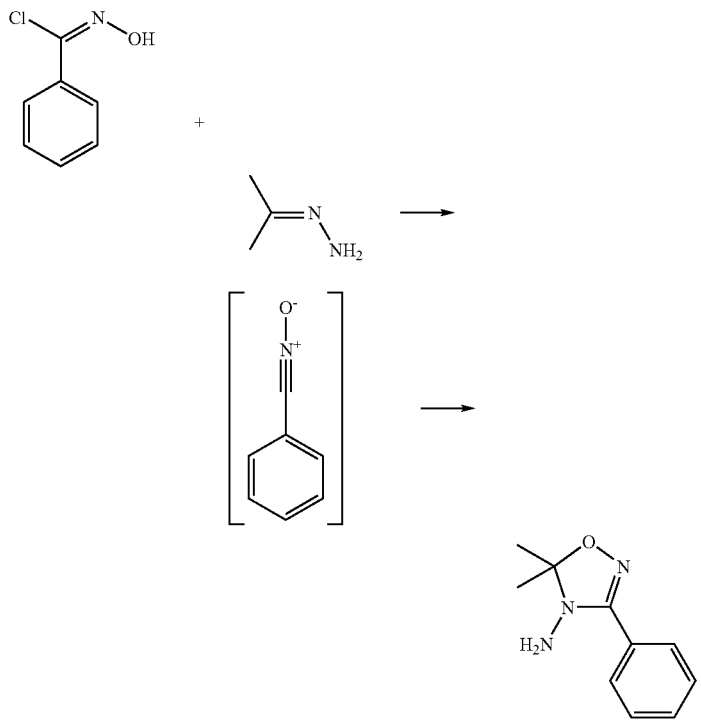

| Method | Solvent | Base | Temp | Time | Yield | Comments |
|---|---|---|---|---|---|---|
| A | CHCl$_3$/H$_2$O | K$_2$CO$_3$ | 40-50° C. | 2 hr | 40% | faster, convenient |
| B | CHCl$_3$/H$_2$O | K$_2$CO$_3$ | 0-40° C. | 6 hr | 45% | product easier to purify |
| C | CH$_2$Cl$_2$ | Et$_3$N | 0-25° C. | 3 hr | 20-24% | |
| D | CHCl$_3$ | Et$_3$N | 0-25° C. | overnight | 40% | impurities appear after 3 hours |
| E | isopropanol | Et$_3$N | 25° C. | 2 hr | 18% | |

TABLE 1-continued

Optimization of [3 + 2] cycloaddition of benzonitrile N-oxide and isopropylidene-hydrazine.

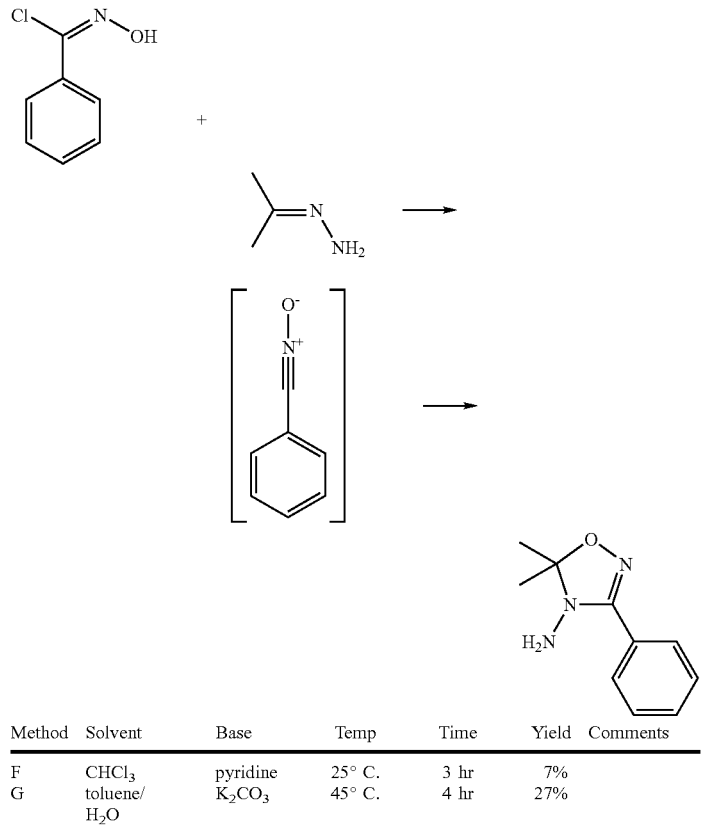

| Method | Solvent | Base | Temp | Time | Yield | Comments |
|--------|---------|------|------|------|-------|----------|
| F | CHCl$_3$ | pyridine | 25° C. | 3 hr | 7% | |
| G | toluene/H$_2$O | K$_2$CO$_3$ | 45° C. | 4 hr | 27% | |

Notes:
1. Chlorooxime/CHCl$_3$ solution added to mixture of hydrazone and base, unless otherwise indicated.
2. Reactions run with acetone hydrazone of ca. 80% purify (azine comprises the remainder).
3. Product purified by trituration with 2% ether/hexanes, but can also be chromatographed on silica gel using 20% EtOAc in hexanes, Rf = 0.4 in 1:1 ethylacetate:hexanes.

1.13 Preparation of N-aroyl-4-amino-Δ$^2$-1,2,4-oxadiazolines

Method A:

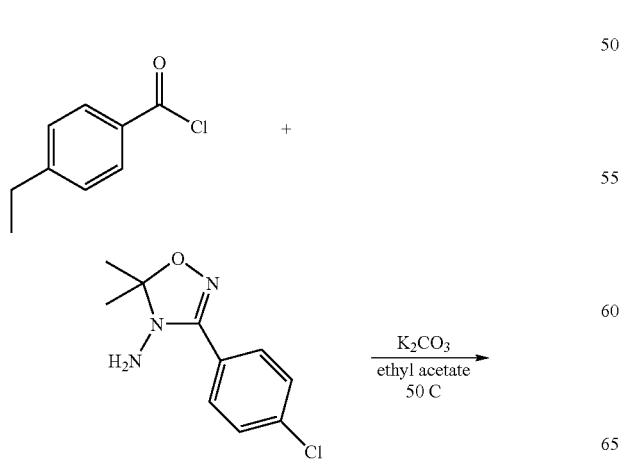

-continued

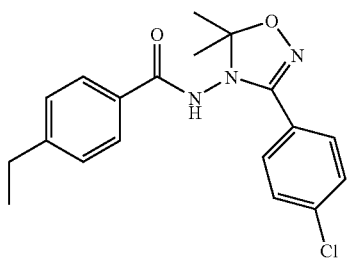

RG-120035

4-Ethylbenzoyl chloride (78.4 mg, 0.466 mmol) and 3-(4-chloro-phenyl)-5,5-dimethyl-[1,2,4]oxadiazol-4-ylamine (100 mg, 0.444 mmol) were dissolved in 4 mL of ethyl acetate in a 20 mL vial. With magnetic stirring, an aqueous solution of K$_2$CO$_3$ (2 mL, 0.166 g/mL) was added, and the mixture was stirred at room temperature for 18-64 hours. The reaction mixture was transferred to a separatory funnel. The organic phase was removed and evaporated to dryness under vacuum at room temperature and then at 50° C. for 30 minutes. The residue was triturated with a solution of 10% ether in hexane (7 mL) for 3-8 hours with magnetic stirring, and the resultant flocculent precipitate was removed and triturated again with 5% ether in hexane. Vacuum oven drying at 50° C. for 30 minutes yielded N-[3-(4-chlorophenyl)-5,5-dimethyl-[1,2,4]oxadiazol-4-yl]-3-ethyl-benzamide in 90% purity. $^1$H-NMR (300 MHz, CDCl$_3$)δ(ppm): 7.72 (d, 2H), 7.6 (d, 2H), 7.35 (d, 2H), 7.25 (d, 2H), 2.7 (q, 2H), 1.63 (s, 6H), 1.22 (t, 3H). Some analogs were purified by trituration with pentane, hexane, or heptane, or alternatively, by column chromatography using an ethyl acetate/hexane gradient.

Most N-aroyl-4-amino-Δ$^2$-1,2,4-oxadiazolines were made by this method.

Method B:

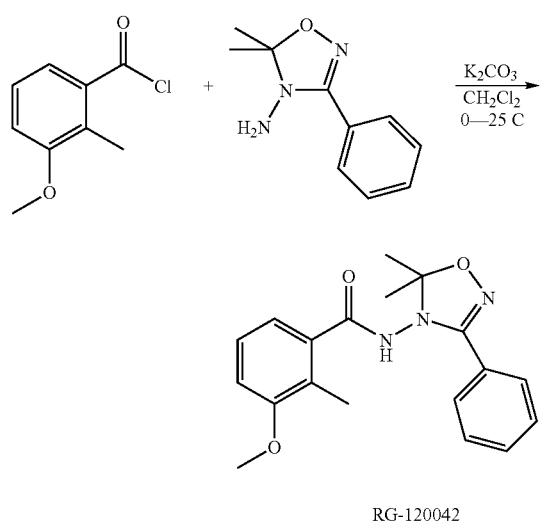

RG-120042

To a solution of 5,5-dimethyl-3-phenyl-[1,2,4]oxadiazol4-ylamine (0.5 g, 2.6 mmol) in 5 mL of CH$_2$Cl$_2$, was added aqueous K$_2$CO$_3$ (0.54 g, 3.9 mmol in 5 mL of water). The mixture was cooled in an ice bath, and a solution of 2-methyl-3-methoxybenzoyl chloride in 5 mL of CH$_2$Cl$_2$ was added to the reaction mixture. Stirring was continued at room temperature for several days. Water and CH$_2$Cl$_2$ were added, the phases were separated, and the organic layer was washed twice with water, once with brine, and dried over MgSO$_4$. The solution was filtered and the solvent was removed in vacuo. Column chromatography on silica gel provided high purity N-(5,5-dimethyl-3-phenyl-[1,2,4]oxadiazol-4-yl)-3-methoxy-2-methyl-benzamide, but in low yield. $^1$H-NMR (300 MHz, CDCl$_3$)δ(ppm): 7.75 (s, 1H[NH]), 7.70 (d, 2H), 7.4 (m, 3H), 7.1 (t, 1H), 6.6 (d, 1H), 3.78 (s, 3H), 1.99 (s, 3H), 1.61 (s, 6H), m.p. 141-142° C. A major by-product was 2-methyl-3-methoxybenzoyl anhydride.

Method C-1:

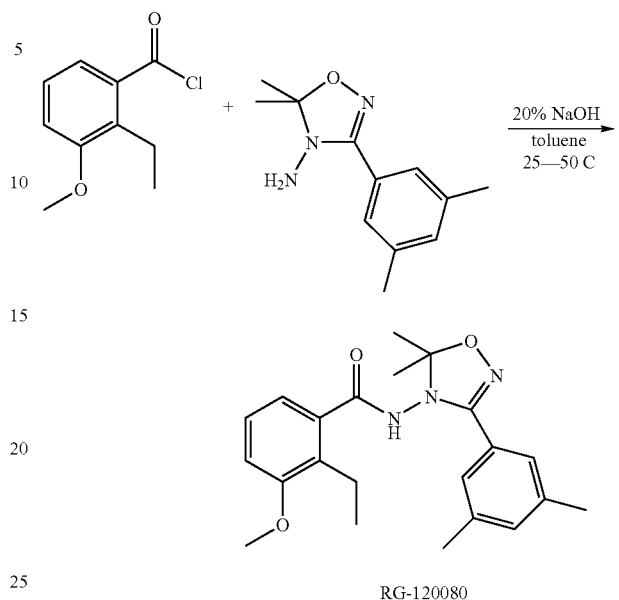

RG-120080

A 20% aqueous solution of NaOH (275 mg, 1.37 mmol) was added to a solution of 3-(3,5-dimethyl-phenyl)-5,5-dimethyl-[1,2,4]oxadiazol-4-ylamine (200 mg, 0.91 mmol) in 2 mL of toluene. 2-Ethyl-3-methoxybenzoyl chloride (199 mg, 1 mmol) was then added to the mixture. The reaction was stirred at room temperature for 2 hours, and then heated at 50° C. for 1 hour. TLC indicated 3 spots. Water, dilute NaOH, and CHCl$_3$ were then added to the reaction mixture. The organic phase was separated, dried over MgSO$_4$, and the solvent removed in vacuo. The residue was triturated with 10% ether in hexane. Filtration and air-drying of the resultant solid provided 100 mg (29% yield) of N-[3-(3,5-dimethyl-phenyl)-5,5-dimethyl-[1,2,4]oxadiazol-4-yl]-2-ethyl-3-methoxy-benzamide. $^1$H-NMR (300 MHz, CDCl$_3$)δ (ppm): 7.42 (s, 2H), 7.11 (s, 1H), 7.11 (t, 1H), 6.9 (d,1H), 6.67 (d, 1H), 3.81 (s, 3H), 2.55 (q, 2H), 2.34 (s, 6H), 1.7 (br s, 6H), 1.05 (t, 3H), Rf=0.5 (1:1 ethyl acetate:hexane).

Method C-2:

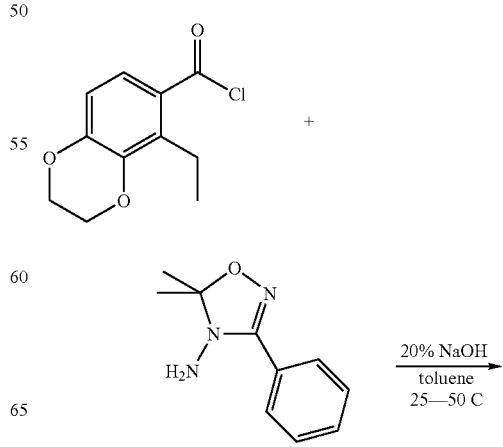

-continued

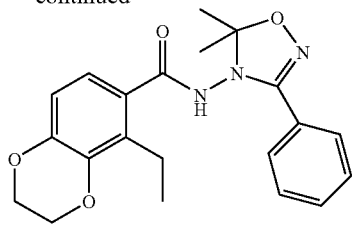

RG-121517

Approximately 18.5 mg (0.42 mmol) of 5-ethyl-2,3-dihydro-benzo[1,4]dioxine-6-carbonyl chloride were added to 103 mg (0.5 mmol) of 5,5-dimethyl-3-phenyl-[1,2,4]oxadiazol-4-ylamine in 2 mL of toluene in a 20 mL vial. Then 400 mg of a 20% aqueous NaOH solution were added. The mixture was stirred at room temperature for 20 hours, and then gently heated at 50° C. for 1 hour. The reaction mixture was transferred to a separatory funnel with CHCl$_3$ and extracted with dilute NaHCO$_3$. The CHCl$_3$ extract was dried and evaporated to dryness. The residue was triturated with pentane to remove the toluene, and then triturated with 5% ether-hexane. $^1$H-NMR indicated the intended product, 5-ethyl-2,3-dihydro-benzo[1,4]dioxine-6-carboxylic acid (5,5-dimethyl-3-phenyl-[1,2,4]oxadiazol-4-yl)-amide, at a purity level of ca. 60%. $^1$H-NMR (300 MHz, CDCl$_3$)δ (ppm): 7.42 (s, 2H), 7.11 (s, 1H), 7.11 (t, 1H), 6.9 (d, 1H), 6.67 (d, 1H), 3.81 (s, 3H), 2.55 (q, 2H), 2.34 (s, 6H), 1.7 (br s, 6H), 1.05 (t, 3H), Rf=0.5 (1:1 ethyl acetate:hexane).

Method D:

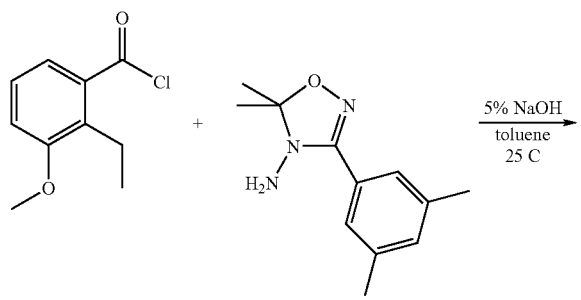

RG-120080

A 5% aqueous solution of NaOH (4 mL) was added to a solution of 3-(3,5-dimethyl-phenyl)-5,5-dimethyl-[1,2,4]oxadiazol-4-ylamine (90 mg) in 6 mL of toluene. 2-Ethyl-3-methoxybenzoyl chloride (140 mg) was then added to the mixture. The reaction was stirred at room temperature for 30 hours. Water and CHCl$_3$ were added. The organic phase was separated, dried over MgSO$_4$, and the solvent was removed in vacuo. The residue was triturated with 100 mL of 10% ether in hexane by magnetic stirring of the mixture in a vessel for 1 hour. Filtration and air-drying of the resultant solid provided 62 mg (40% yield) of N-[3-(3,5-dimethyl-phenyl)-5,5-dimethyl-[1,2,4]oxadiazol-4-yl]-2-ethyl-3-methoxy-benzamide. $^1$H-NMR (300 MHz, CDCl$_3$)δ (ppm): 7.42 (s, 2H), 7.11 (s, 1H), 7.11 (t, 1H), 6.9 (d, 1H), 6.67 (d, 1H), 3.81 (s, 3H), 2.55 (q, 2H), 2.34 (s, 6H), 1.7 (br s, 6H), 1.05 (t, 3H), Rf=0.5 (1:1 ethyl acetate:hexane). The filtrate contained an additional quantity of the intended product.

Method E:

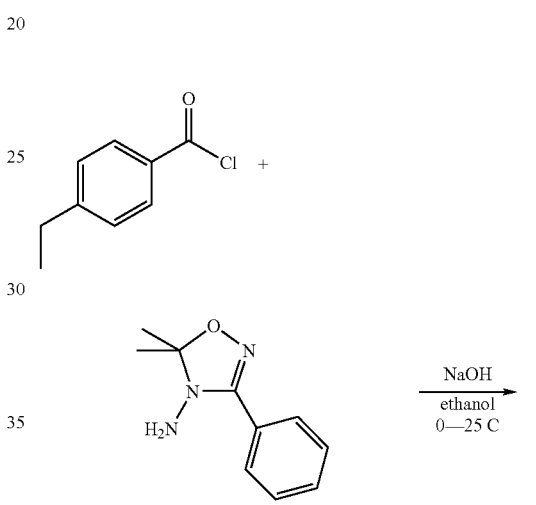

RG-120115

To an ice-cold stirred solution of the 5,5-dimethyl-3-phenyl-[1,2,4]oxadiazol-4-ylamine (0.5 g, 2.6 mmol) in 6 mL of ethanol, was added an excess of 4-ethylbenzoyl chloride (4 mL), followed by aqueous NaOH (8%, 7 mL). The solution was stirred overnight and allowed to warm to room temperature. The mixture was diluted with water and extracted with CH$_2$Cl$_2$. The combined CH$_2$Cl$_2$ extracts were dried over MgSO$_4$, and the solvent was removed in vacuo. The product, N-(5,5-dimethyl-3-phenyl-[1,2,4]oxadiazol-4-yl)-3-ethyl-benzamide, was isolated by silica gel chromatography. $^1$H-NMR (300 MHz, CDCl$_3$)δ (ppm): 7.8 (m, 3H), 7.6 (d, 2H), 7.4 (m, 2H), 7.2 (d, 2H), 2.7 (q, 2H), 1.65 (s, 6H), 1.2 (t, 3H).

TABLE 2

Optimization of amide formation between 2-ethyl-3-methoxybenzoyl chloride and 3-(3,5-dimethyl-phenyl)-5,5-dimethyl-[1,2,4]-oxadiazol-4-ylamine.

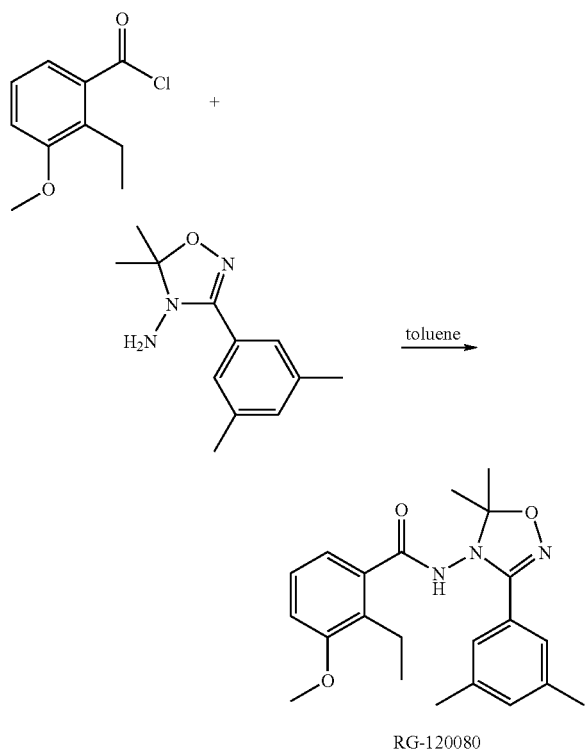

RG-120080

| Time | Temp | Base | Yield |
| --- | --- | --- | --- |
| 4-5 hr | 25° C. | 20% NaOH | 24% |
| 2 days | 25° C. | 25% K₂CO₃ | 20% |
| 2 days | 25° C. | 50% K₂CO₃ | 8% |
| 20-30 hr | 25° C. | 5% NaOH | 40% |
| 20+ hr | 25° C. | 3% NaOH | >60% |

1. Purification by trituration with 5-10% ether-hexanes gave 90-98% pure product. Higher ether content reduces yield but enhances purity.
2. In separate experiments with 3-NO₂ oxadiazoline, K₂CO₃/CH₂Cl₂ gave at least 50% yields.
3. K₂CO₃/EtOH also found to be acceptable. (1 eq. oxadiazoline, 2 eq. ROCl, 2.5 eq. K₂CO₃).
4. NaH/THF at 25° C. or NaH/THF/DMF at 25-75° C. for the unsubstituted oxadiazoline and 4-ethylbenzoyl chloride results in only a trace of product at best. Heating the two reactants neat at 150° C. for 2 hours results in a tar.
5. Powdered KOH in THF for the unsubstituted oxadiazoline and 2-methyl-3-methoxybenzoyl chloride results in only a trace of product.

1.14 Preparation of aryl-[1,2,4]oxadiazol-4-yl-ureas from the Reaction of aryl-[1,2,4]oxadiazol-4-ylamines with Isocyantes

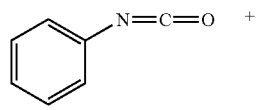

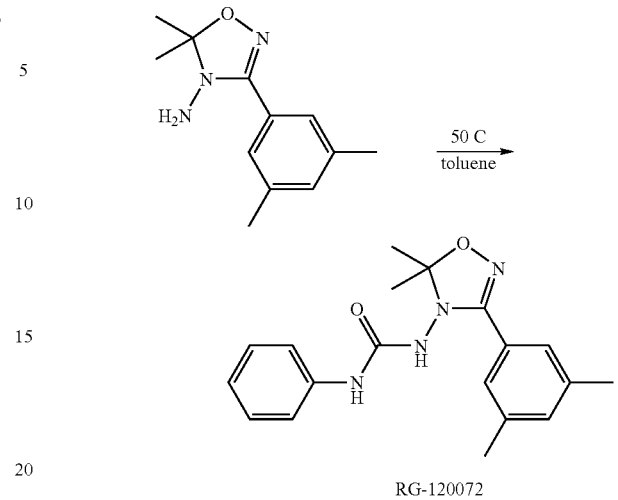

RG-120072

3-(3,5-Dimethyl-phenyl)-5,5-dimethyl-[1,2,4]oxadiazol-4-ylamine (219 mg, 1 mmol) and phenylisocyanate (131 mg, 1.1 mmol) were dissolved in 1 mL of toluene and stirred at room temperature for 2 hours. TLC indicated a partial reaction; therefore the mixture was heated at 50° C. for 2 hours. The solvent was removed in vacuo and the residue was stirred in 25 mL of 10% ether in hexane. 1-[3-(3,5-Dimethyl-phenyl)-5,5-dimethyl-[1,2,4]oxadiazol-4-yl]-3-phenyl-urea was recovered as a white precipitate (106 mg, 31% yield). ¹H-NMR (300 MHz, CDCl₃) 6 (ppm): 7.78 (s, 1H [NH]), 7.5 (d, 2H), 7.4 (t, 2H), 7.3 (s, 2H), 7.2 (t, 1H), 7.15 (s, 1H), 6.4 (s, 1H [NH]), 2.28 (s, 6) 1.73 (s, 3H), 1.54 (s, 3H).

1.15 Preparation of N-[3-(3,5-Dimethyl-phenyl)-5,5-dimethyl-[1,2,4]oxadiazol-4-yl]-3-methoxy-2-methyl-benzamide (RG-120045)

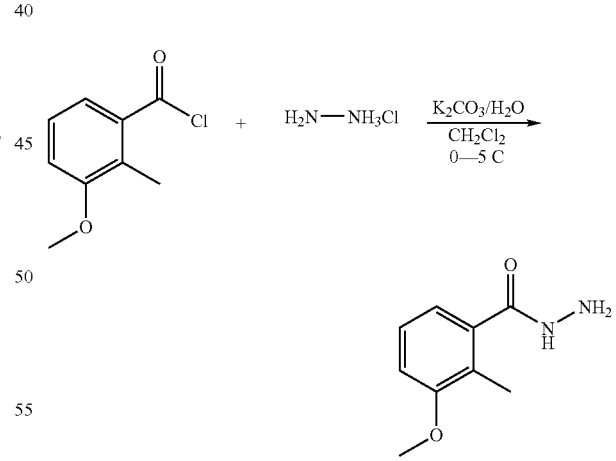

To a 500 mL, 3-neck flask equipped with a magnetic stirrer, and chilled in an ice water bath, were added 25 mL of CH₂Cl₂ (significantly greater quantities can be used) and 22.5 g (450 mmol) of hydrazine hydrate, followed by a solution of 31.5 g of K₂CO₃ dissolved in 60 mL of water. Over a period of 30 minutes, a solution of 31 g (168 mmol) of 2-methyl, 3-methoxybenzoyl chloride dissolved in 50 mL of CH₂Cl₂ was added, while keeping the temperature below 5° C. The reaction mixture was allowed to warm to room temperature and then stirred for an additional 2 hours. Water (100 mL) and chloroform (150 mL) were added, the mixture was shaken in a separatory funnel, and an inorganic precipitate was filtered off. The organic layer was dried over MgSO$_4$ and the solvent removed in vacuo to leave 30 g of crude product hydrazide. This material was slurried with heptane for 4 hours (pentane slurry gives comparable results). Filtration and residual solvent evaporation yielded 13 g of 3-methoxy-2-methyl-benzoic acid hydrazide, containing ca. 10% of diacylated material. The product could be further purified by precipitation with hot CHCl$_3$/hexane. $^1$H NMR (300 MHz, CDCl$_3$)δ(ppm): 7.2 (t, 1H), 6.95 (br s, 1H), 6.9 (m, 2H), 4.15 (br s, 2H), 3.84 (s, 3H), 2.27 (s, 3H).

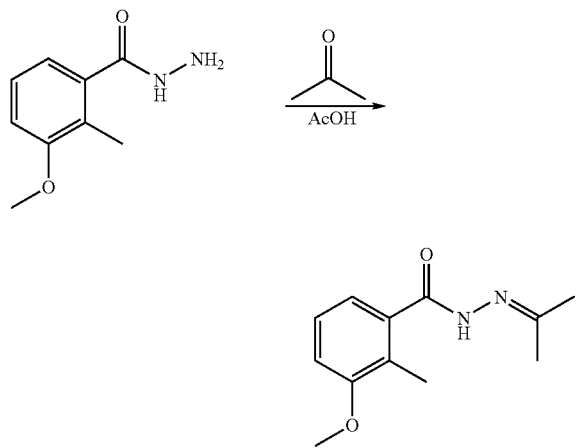

3-methoxy-2-methyl-benzoic acid hydrazide (1.1 g) was dissolved in 10 mL of acetone in a 25 mL round bottom flask. 2 drops of acetic acid were added and the reaction was stirred at room temperature for 10 minutes. The vessel was placed in a refrigerator for 1 hour and the product, 3-methoxy-2-methyl-benzoic acid isopropylidene-hydrazide, was filtered off and dried. $^1$H NMR (300 MHz, CDCl$_3$)δ(ppm): 7.2 (t, 1H), 7.02 (d, 1H), 6.94 (d, 1H), 3.85 (s, 3H), 2.33 (s, 3H), 2.18 (s, 3H, benzylic), 1.88 (s, 3H).

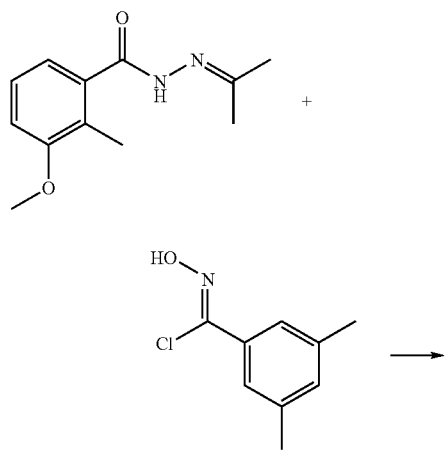

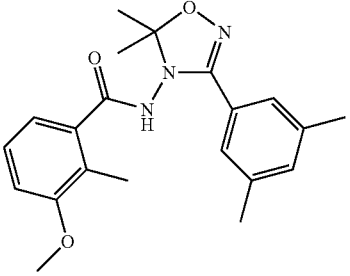

3-Methoxy-2-methyl-benzoic acid isopropylidene-hydrazide (1.71 g, 7.77 mmol) and 3,5-dimethyl-benzaldehyde chlorooxime (2.29 g, 12.4 mmol), both as CHCl$_3$ solutions (total volume 40 mL), were added to a 250 mL round bottom flask equipped with a magnetic stirrer. An aqueous K$_2$CO$_3$ solution (5 g in 30 mL) was added, the vessel was placed in a 50° C. water bath, and the reaction was stirred vigorously for 24 hours. The reaction was monitored by $^1$H NMR. Chloroform (100 mL) and water (50 mL) were added, and the mixture was shaken in a separatory funnel. The organic phase was separated, dried, and the solvent was removed in vacuo. Column chromatography on silica gel using a gradient of 10-30% ethyl acetate in hexane yielded 1.07 g of N-[3-(3,5-dimethyl-phenyl)-5,5-dimethyl-[1,2,4]oxadiazol-4-yl]-3-methoxy-2-methyl-benzamide (32%). An analytical sample was obtained by crystallization from CH$_2$Cl$_2$/hexane under refrigeration. $^1$H NMR (300 MHz, CDCl$_3$)δ(ppm): 7.4 (s, 2H), 7.1 (t, 1H), 7.07 (s, 1H), 6.85 (d, 1H), 6.65 (d, 1H), 3.78 (s, 3H), 2.30 (s, 6H), 2.07 (s, 3H), 1.65 (s, 6H).

TABLE 3

Summary of the reaction conditions explored.

| Base/Solvent | Time/Temp | Hydrazone: Oxime Chloride | Yield (by $^1$H NMR) |
|---|---|---|---|
| 1.25 eq. Et$_3$N, CHCl$_3$ | Overnight, 25° C. | 1:1 | 5-10% |
| 1.25 eq. Et$_3$N, CHCl$_3$ | 4 hr, 45° C. | 1:2 | 20-30% |
| 17% aq. K$_2$CO$_3$/CHCl$_3$ | 3 hr, 45° C. | 1:1 | 20-25% |
| 17% aq. K$_2$CO$_3$/CHCl$_3$ | 5 hr, 45° C. | 1:1 | 25-30% |
| 1.8 eq. Et$_3$N, ClCH$_2$CH$_2$Cl | 2 hr, reflux | 1:1.3 | 15-20% |
| K$_2$CO$_3$ (powder)/ ClCH$_2$CH$_2$Cl | 2 hr, 60° C. | 1:1.7 | 25-30% |
| K$_2$CO$_3$ (powder) + MgSO$_4$ (powder) | 4 hr, reflux | 1:1.5 | 10% |
| 17% aq. K$_2$CO$_3$/ CHCl$_3$ | 24 hr, 60° C. | 1:3 | 32% (isolated) |

In general, K$_2$CO$_3$ as base gave cleaner products compared with the Et$_3$N.

1.16 Preparation of N-[3-(3,5-dimethyl-phenyl)-1,8-dioxa-2,4-diaza-spiro[4.5]dec-2-en-4-yl]-3-methoxy-2-methyl-benzamide (RG-120086).

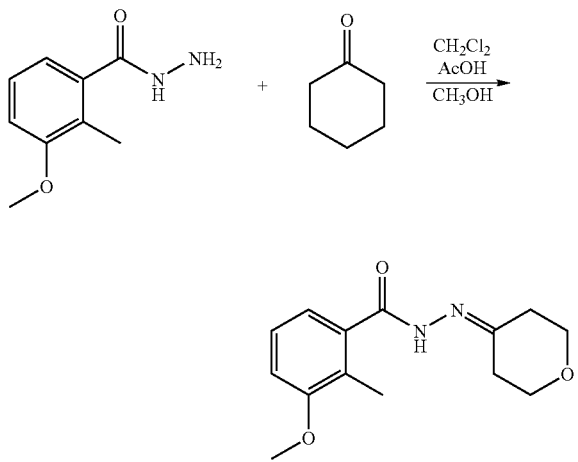

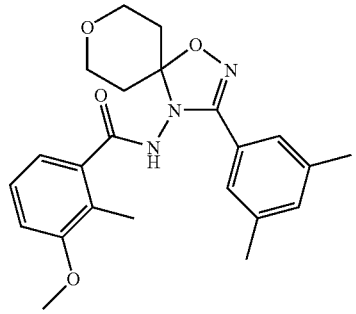

3-methoxy-2-methyl-benzoic acid hydrazide (4.14 g, 23 mmol) was suspended in a mixture of 80 mL of ether, 40 mL of CH$_2$Cl$_2$ and 2 drops of acetic acid. A solution of tetrahydro-pyran-4-one (2.3 g, 23 mmol) in 20 mL of CH$_2$Cl$_2$ and 2-3 mL of methanol were added, and the mixture was refluxed for 10 minutes. The reaction mixture was allowed to cool and was concentrated to about 80 mL. Pentane (100 mL) was added, resulting in the formation of a precipitate. The suspension was chilled in a freezer and filtered to yield 5.04 g of 3-methoxy-2-methyl-benzoic acid (tetrahydro-pyran-4-ylidene)-hydrazide as a tan, flocculent, semi-crystalline material. $^1$H NMR (300 MHz, CDCl$_3$) δ(ppm): 7.2 (t, 1H), 6.98 (d, 1H), 6.95 (d, 1H), 3.9 (t, 2H), 3.86 (s, 3H), 3.8 (t, 2H), 2.65 (t, 2H), 2.42 (t, 2H), 2.35 (s, 3); Rf=0.15 (3:1 ethyl acetate:hexane).

3,5-dimethyl-benzaldehyde chlorooxime (1.84 g, 4 mmol) was dissolved in 30 mL of CHCl$_3$ in a round bottom flask. An aqueous solution of K$_2$CO$_3$ (25 mL, 0.1 66 g/mL) was added, followed by 1.05 g of 3-methoxy-2-methyl-benzoic acid (tetrahydro-pyran4-ylidene)-hydrazide. The reaction was stirred overnight at 55-60° C. Water and CH$_2$Cl$_2$ (50 mL) were added, and the mixture was shaken in a separatory funnel. The aqueous phase was removed and extracted once with CHCl$_3$ (25 mL). The organic phases were combined, washed once with dilute K$_2$CO$_3$, and dried over MgSO$_4$. The solvent was removed in vacuo to yield 2.5 g of crude product. This material was triturated twice with 10% ether in hexane and then once with 25% ether in hexane. The solids were collected and filtered, yielding 720 mg of N-[3-(3,5-dimethyl-phenyl)-1,8-dioxa-2,4-diaza-spiro[4.5]dec-2-en-4-yl]-3-methoxy-2-methyl-benzamide at 80% purity and a 49% yield. $^1$H NMR (300 MHz, CDCl$_3$) δ(ppm): 8.5 (s, 1H [NH]), 7.4 (s, 2H), 7.1 (m, 1H), 7.1 (s, 1H), 6.9 (d, 1H), 6.65 (d, 1H), 3.9 (m, 4H), 3.8 (s, 3H), 2.4 (m, 4H), 2.35 (s, 6H), 2.05 (s, 3H).

1.17 Preparation of N-[3-(3,5-Dimethyl-phenyl)-1-oxa-2,4-diaza-spiro[4,5]-7,8-benzo-dec-2-en4-yl]-3-methoxy-2-methyl-benzamide (RG-120037)

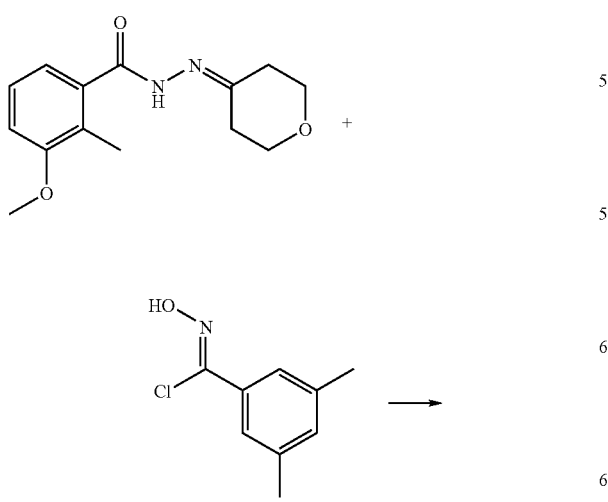

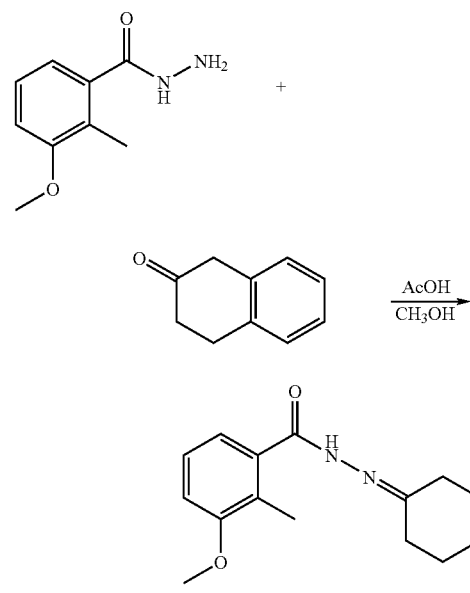

3-Methoxy-2-methyl-benzoic acid hydrazide (1.0 g) and P-tetralone (0.9 g) were mixed in 4 mL of methanol with 1 drop of acetic acid at room temperature for 10 minutes. Approximately 10 mL of ether were added and the mixture was refrigerated. Crystals of 3-methoxy-2-methyl-benzoic acid (3,4-dihydro-1H-naphthalen-2-ylidene)-hydrazide formed, which were collected by filtration (0.85 g). $^1$H NMR (300 MHz, CDCl$_3$)δ(ppm): 6.8-7.3 (m, 4H), 3.75+3.8 (2 s, 3H), 3.45+3.7 (2 s, 2H), 2.85 (t, 2H), 2.4 (t, 2H), 2.27+2.25 (2 s, 3H); multiple conformers; Rf=0.56 (3:1 ethyl acetate:hexane); m.p.=138° C.; m.p. of 3-methoxy-2-methyl-benzoic acid hydrazide=113-116° C.

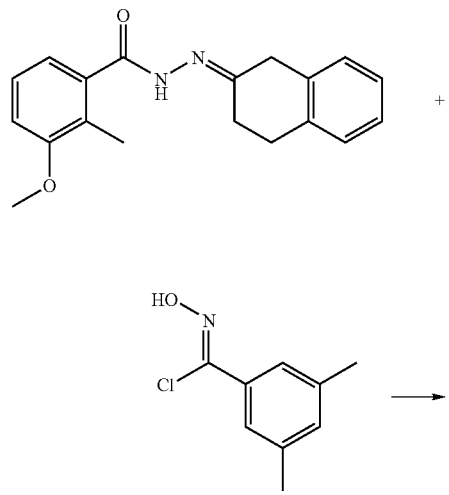

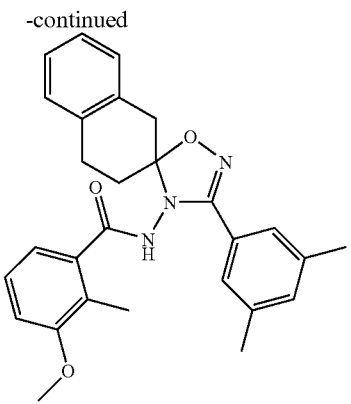

RG-120037

3-Methoxy-2-methyl-benzoic acid (3,4-dihydro-1H-naphthalen-2-ylidene)-hydrazide (1.25 g) was mixed with 3,5-dimethyl-benzaldehyde chlorooxime (1.68 g) and 3.1 g of triethylamine in 5 mL of DMF in a round bottom flask, causing the reaction mixture to turn red immediately. Water was added to the reaction mixture and extracted with ether to yield 2.05 g of crude product, which was then chromatographed twice on alumina using a hexane/ethyl acetate/methanol gradient. The intended product, N-[3-(3,5-dimethyl-phenyl)-1-oxa-2,4-diaza-spiro[4.5]-7,8-benzo-dec-2-en-4-yl]3-methoxy-2-methyl-benzamide, eluted with solvent compositions ranging from 60:40 ethyl acetate:hexane to 97:3 ethyl acetate:methanol. $^1$H NMR (300 MHz, CDCl$_3$)δ(ppm): 7.1 (s, 2H), 7.05 (s, 1H), 7.03 (m, 2H), 7.0 (m, 2H), 6.95 (m, 2H), 6.75 (m, 1H), 4.8 (br, 1H [NH]), 3.71 (s, 3H), 2.8 (m, 1H), 2.65 (m, 1H), 2.22 (m, 4H), 2.2 (s, 6H), 2.1+2.05 (2 s, 3H). An analogous reaction in CHCl$_3$/aqueous K$_2$CO$_3$ at 60° C. overnight or in acetonitrile with Koenig's base at reflux gave little or none of the desired product.

TABLE 4

Physical Characterization of Compounds

| Compound | NMR frequency | Solvent | R$^1$ | R$^4$ | R$^1$ + R$^4$ | R$^2$ + R$^3$ | NH |
|---|---|---|---|---|---|---|---|
| RG-120111 | 300 MHz | CDCl3 | 7.95 (d, 2H), 7.65 (m, 1H), 7.55 (m, 2H) | 7.35 (s, 2H), 7.03 (s, 1H), 2.26 (s, 6H) | | 1.62 (s, 6H) | 9.15 (s, 1H) |
| RG-120056 | 300 MHz | CDCl3 | 6.95 (m, 1H), 7.3 (br, 3H), 2.38 (s, 3H) | 7.35 (s, 2H), 7.1 (s, 1H), 2.29 (s, 6H) | | 1.56 (s, 6H) | 7.7 (s, 1H), 6.0 (s, 1H) |
| RG-120072 | 300 MHz | CDCl3 | 7.5 (d, 2H), 7.4 (t, 2H), 7.2 (t, 1H) | 7.3 (s, 2H), 7.15 (s, 1H), 2.28 (s, 6H) | | 1.73 (s, 3H), 1.54 (s, 3H) | 7.78 (s, 1H), 6.4 (s, 1H) |
| RG-120075 | 300 MHz | CDCl3 | 8.1 (d, 1H), 7.5 (m, 1H), 7.1 (m, 1H), 6.95 (d, 1H), 3.83 (s, 3H) | 7.4 (s, 2H), 7.05 (s, 1H), 2.27 (s, 6H) | | 1.56 (s, 6H) | 9.0 (s, 1H) |
| RG-120091 | 300 MHz | CDCl3 | 8.4 (d, 1H), 8.0 (d, 1H), 7.75 (s, 1H), 7.65 (t, 1H) | 7.4 (s, 2H), 7.1 (s, 1H), 2.29 (s, 6H) | | 1.57 (s, 6H) | 8.45 (s, 1H) |
| RG-120098 | 300 MHz | CDCl3 | 8.1 (m, 1H), 7.6 (m, 2H), 7.1 (m, 1H) | 7.45 (s, 2H), 7.15 (s, 1H), 2.37 (s, 6H) | | 1.56 (s, 6H) | |
| RG-120077 | 300 MHz | CDCl3 | 7.50 (s, 1H), 7.45 (s, 1H), 7.35 (m, 1H), 7.05 (s, 1H), 2.36 (s, 3H) | 7.41 (s, 2H), 7.05 (s, 1H), 2.28 (s, 6H) | | 1.57 (s, 6H) | |

TABLE 4-continued

Physical Characterization of Compounds

| Compound | NMR frequency | Solvent | R¹ | R⁴ | R¹ + R⁴ | R² + R³ | NH |
|---|---|---|---|---|---|---|---|
| RG-120060 | 300 MHz | CDCl3 | 7.55 (d, 2H), 7.25 (d, 2H), 2.7 (q, 2H), 1.25 (t, 3H) | 7.4 (s, 2H), 7.05 (s, 1H), 2.3 (s, 6H) | | 1.56 (s, 6H) | |
| RG-120024 | 300 MHz | CDCl3 | 7.55 (d, 2H), 7.4 (d, 2H) | 7.4 (s, 2H), 7.05 (s, 1H), 2.28 (s, 6H) | | 1.56 (s, 6H) | |
| RG-120080 | 300 MHz | CDCl3 | 7.11 (t, 1H), 6.9 (d, 1H), 6.67 (d, 1H), 3.81 (s, 3H), 2.55 (q, 2H), 1.05 (t, 3H) | 7.42 (s, 2H), 7.11 (s, 1H), 2.34 (s, 6H) | | 1.7 (br s, 6H) | |
| RG-120002 | 300 MHz | CDCl3 | 7.55 (s, 1H), 7.2–7.4 (m, 3H) | 7.4 (s, 2H), 7.05 (s, 1H), 2.29 (s, 6H) | | 1.57 (s, 6H) | |
| RG-120015 | 300 MHz | CDCl3 | 7.6 (m, 2H), 7.5 (m, 1H), 7.4 (t, 2H) | 8.07 (s, 1H), 7.97 (d, 1H), 7.7 (d, 1H), 7.55 (m, 1H) | | 1.66 (s, 6H) | |
| RG-120148 | 300 MHz | CDCl3 | 7.55 (d, 2H), 7.2 (d, 2H), 2.68 (q, 2H), 1.21 (t, 3H) | 8.1 (s, 1H), 7.97 (d, 1H), 7.7 (d, 1H), 7.5 (d, 1H) | | 1.64 (s, 6H) | 7.75 (br, 1H) |
| RG-120022 | 300 MHz | CDCl3 | 7.15 (t, 1H), 6.9 (d, 1H), 6.62 (d, 1H), 3.80 (s, 3H), 2.50 (br s, 2H), 0.97 (t, 3H) | 7.87 (d, 2H), 7.3 (d, 2H) | | 1.65 (br s, 6H) | 7.20 (s, 1H) |
| RG-120094 | 300 MHz | CDCl3 | 7.42 (s, 1H), 7.27 (s, 1H), 6.55 (m, 1H) | 7.85 (d, 2H), 7.22 (d, 2H) | | 1.62 (s, 6H) | |
| RG-120160 | 300 MHz | CDCl3 | 7.85 (m, 1H), 7.25 (m, 2H), 7.05 (m, 2H), 3.48 (s, 2H) | 7.67 (d, 2H), 7.18 (d, 2H) | | 1.48 (s, 6H) | 6.85 (s, 1H) |
| RG-120066 | 300 MHz | CDCl3 | 7.32 (m, 3H), 7.18 (m, 2H), 4.44 (s, 2H), 3.98 (s, 2H) | 7.77 (d, 2H), 7.25 (d, 2H) | | 1.66 (s, 6H) | 7.95 (s, 1H) |
| RG-120088 | 300 MHz | CDCl3 | 7.3–7.4 (m, 4H), 6.15 (m, 1H), 4.6 (dd, 1H), 4.45 (dd, 1H) | 7.2 (s, 2H), 7.1 (s, 1H), 2.27 (s, 6H) | | 1.56 (s, 6H) | 5.95 (s, 1H) |
| RG-120029 | 300 MHz | CDCl3 | 7.25 (m, 4H), 7.05 (t, 1H), 4.52 (s, 2H) | 7.75 (d, 2H), 6.78 (d, 2H) | | 1.55 (s, 6H) | 7.9 (s, 1H) |
| RG-120109 | 300 MHz | CDCl3 | 7.95 (m, 1H), 7.8 (m, 1H), 7.55 (m, 1H), 7.47 (m, 2H) | 7.85 (d, 2H), 7.21 (d, 2H) | | 1.66 (s, 6H) | |
| RG-120033 | 300 MHz | CDCl3 | 7.62 (d, 2H), 7.55 (t, 1H), 7.4 (t, 2H) | 7.82 (d, 2H), 7.21 (d, 2H) | | 1.65 (s, 6H) | |
| RG-120055 | 300 MHz | CDCl3 | 7.55 (d, 2H), 7.25 (d, 2H), 2.7 (q, 2H), 1.22 (t, 3H) | 7.8 (d, 2H), 7.21 (d, 2H) | | 1.61 (s, 6H) | 7.65 (s, 1H) |
| RG-120147 | 300 MHz | CDCl3 | 7.57 (m, 3H), 7.42 (m, 2H) | 7.52 (m, 1H), 7.5 (m, 1H), 7.05 (t, 1H), 6.97 (d, 1H), 3.89 (s, 3H) | | 1.66 (s, 6H) | 8.05 (s, 1H) |
| RG-120062 | 300 MHz | CDCl3 | | 7.5 (d, 1H), 7.5 (t, 1H), 7.07 (t, 1H), 7.02 (d, 1H), 3.95 (s, 3H) | | 1.62 (s, 6H) | 8.55 (br s, 1H) |
| RG-120026 | 300 MHz | CDCl3 | 7.5 (d, 2H), 7.2 (d, 2H), 2.65 (q, 2H), 1.22 (t, 3H) | 7.6 (d, 1H), 7.45 (t, 1H), 7.05 (t, 1H), 7.0 (d, 1H), 3.91 (s, 3H) | | 1.65 (s, 6H) | 8.05 (s, 1H) |
| RG-120070 | 300 MHz | CDCl3 | 7.45 (s, 1H), 7.2 (d, 1H), 6.5 (m, 1H) | 8.07 (s, 1H), 7.95 (d, 1H), 7.68 (d, 1H), 7.55 (t, 1H) | | 1.65 (s, 6H) | 7.85 (s, 1H) |

TABLE 4-continued

Physical Characterization of Compounds

| Compound | NMR frequency | Solvent | R¹ | R⁴ | R¹ + R⁴ | R² + R³ | NH |
|---|---|---|---|---|---|---|---|
| RG-120093 | 300 MHz | CDCl3 | 7.2 (t, 1H), 6.9 (d, 1H), 6.65 (d, 1H), 3.80 (s, 3H), 2.47 (br s, 2H), 0.97 (t, 3H) | 8.1 (s, 1H), 8.05 (d, 1H), 7.75 (d, 1H), 7.6 (t, 1H) | | 1.7 (br s, 6H) | |
| RG-120006 | 300 MHz | CDCl3 | 7.35 (m, 3H), 7.18 (m, 2H), 4.45 (s, 2H), 3.95 (s, 2H) | 8.0 (s, 1H), 7.92 (d, 1H), 7.75 (d, 1H), 7.57 (t, 1H) | | 1.57 (s, 6H) | |
| RG-120108 | 300 MHz | CDCl3 | 7.85 (m, 2H), 7.8 (s, 1H), 7.45 (m, 2H) | 8.1 (s, 1H), 7.97 (d, 1H), 7.7 (d, 1H), 7.55 (m, 1H) | | 1.57 (s, 6H) | |
| RG-120021 | 300 MHz | CDCl3 | 7.35 (m, 3H), 7.05 (m, 2H), 3.46 (s, 2H) | 7.9 (s, 1H), 7.85 (d, 1H), 7.7 (d, 1H), 7.5 (t, 1H) | | 1.48 (br s, 6H) | 8.1 (s, 1H) |
| RG-120163 | 300 MHz | CDCl3 | 7.25 (d, 1H), 7.01 (t, 1H), 7.79 (d, 1H), 4.5 (s, 2H) | 8.05 (s, 1H), 7.95 (d, 1H), 7.7 (d, 1H), 7.55 (t, 1H) | | 1.57 (s, 6H) | 7.9 (s, 1H) |
| RG-120059 | 300 MHz | CDCl3 | | 8.1 (s, 1H), 7.95 (d, 1H), 7.75 (d, 1H), 7.57 (t, 1H) | | 1.57 (s, 6H) | 3.55 (br s, 1H) |
| RG-120001 | 300 MHz | CDCl3 | 7.75 (m, 1H), 7.37 (m, 2H), 7.17 (m, 2H) | 8.0 (s, 1H), 7.8 (m, 1H), 7.55 (d, 1H), 7.47 (m, 1H) | | 1.71 (s, 3H), 1.53 (s, 3H) | |
| RG-120153 | 300 MHz | CDCl3 | 4.05 (q, 2H), 2.55 (br, 2H), 2.30 (m, 2H), 1.57 (s, 6H), 1.2 (t, 3H) | 8.1 (s, 1H), 7.95 (d, 1H), 7.75 (d, 1H), 7.57 (t, 1H) | | | 3.55 (br s, 1H) |
| RG-120018 | 300 MHz | CDCl3 | 7.35 (m, 3H), 7.2 (m, 2H), 4.4 (s, 2H), 3.95 (s, 2H) | 7.5 (m, 1H), 7.4 (m, 1H), 7.02 (t, 1H), 6.85 (d, 1H), 3.63 (s, 3H) | | 1.59 (s, 6H) | 8.4 (s, 1H) |
| RG-120057 | 300 MHz | CDCl3 | 7.25 (m, 2H), 6.75 (m, 3H), 4.45 (s, 2H) | 7.55 (d, 1H), 7.4 (t, 1H), 7.05 (m, 2H), 3.77 (s, 3H) | | 1.57 (s, 6H) | 8.4 (s, 1H) |
| RG-120025 | 300 MHz | CDCl3 | 7.45 (m, 2H), 7.35 (m, 2H), 6.97 (m, 1H) | 7.5 (m, 2H), 7.05 (m, 2H), 3.83 (s, 3H) | | 1.8 (s, 3H), 1.5 (s, 3H) | 7.75 (s, 1H), 6.35 (s, 1H) |
| RG-120122 | 300 MHz | CDCl3 | 7.5 (d, 2H), 7.4 (m, 2H), 7.2 (t, 1H) | 7.75 (d, 2H), 7.3 (d, 2H) | | 1.59 (s, 6H) | 6.55 (s, 1H) |
| RG-120047 | 300 MHz | CDCl3 | 7.9 (m, 2H), 7.6 (m, 1H), 7.5 (m, 2H) | 7.5 (m, 1H), 7.4 (m, 1H), 7.05 (m, 1H), 7.0 (m, 1H), 3.95 (s, 3H) | | 1.68 (s, 6H) | |
| RG-120144 | 300 MHz | CDCl3 | 4.1 (q, 1H), 2.2–2.7 (m, 4H), 1.2 (t, 3H) | 7.5 (m, 1H), 7.4 (m, 1H), 7.05 (m, 1H), 7.0 (m, 1H), 3.9 (s, 3H) | | 1.57 (s, 6H) | |
| RG-120127 | 300 MHz | CDCl3 | 7.25 (m, 2H), 7.05 (t, 1H), 6.8 (d, 2H), 4.52 (s, 2H) | 7.3 (d, 1H), 7.2 (s, 1H), 6.8 (d, 1H), 6.0 (s, 2H) | | 1.53 (s, 6H) | 7.9 (s, 1H) |
| RG-120017 | 300 MHz | CDCl3 | 7.5 (m, 2H), 7.4 (m, 2H), 7.15 (m, 1H) | 7.22 (s, 1H), 7.2 (d, 1H), 6.8 (d, 1H), 5.99 (s, 2H) | | 1.73 (s, 6H) | |
| RG-120140 | 300 MHz | CDCl3 | 7.85 (m, 3H), 7.45 (m, 2H) | 7.3 (d, 1H), 7.25 (s, 1H), 6.8 (d, 1H), 5.96 (s, 2H) | | 1.64 (s, 6H) | |
| RG-120083 | 300 MHz | CDCl3 | 4.1 (q, 2H), 2.6 (br, 2H), 2.3 (t, 2H), 1.25 (t, 3H) | 7.2 (m, 2H), 6.8 (d, 1H), 6.02 (s, 2H) | | 1.56 (s, 6H) | |
| RG-120156 | 300 MHz | CDCl3 | 7.7 (m, 2H), 7.55 (t, 1H), 7.45 (t, 2H) | 7.3 (m, 2H), 6.8 (d, 1H), 5.98 (s, 2H) | | 1.62 (s, 6H) | |
| RG-120012 | 300 MHz | CDCl3 | 7.4 (s, 1H), 7.5 (s, 1H), 6.5 (m, 1H) | 7.6 (d, 1H), 7.45 (m, 1H), 7.05 (t, 1H), 6.95 (d, 1H), 3.95 (s, 3H) | | 1.65 (s, 6H) | 8.35 (s, 1H) |

TABLE 4-continued

Physical Characterization of Compounds

| Compound | NMR frequency | Solvent | R¹ | R⁴ | R¹ + R⁴ | R² + R³ | NH |
|---|---|---|---|---|---|---|---|
| RG-120061 | 300 MHz | CDCl3 | 7.6 (d, 2H), 7.25 (d, 2H), 2.7 (q, 2H), 1.22 (t, 3H) | 7.3 (m, 2H), 6.8 (d, 1H), 5.98 (s, 2H) | | 1.62 (s, 6H) | |
| RG-120016 | 300 MHz | CDCl3 | 7.05 (t, 1H), 6.9 (d, 1H), 6.45 (d, 1H), 3.83 (s, 3H), 2.4 (q, 2H), 0.95 (t, 3H) | 7.65 (d, 1H), 7.45 (t, 1H), 7.1 (t, 1H), 6.97 (d, 1H), 3.80 (s, 3H) | | 1.7 (s, 6H) | 7.4 (s, 1H) |
| RG-120157 | 300 MHz | CDCl3 | 7.2 (m, 3H), 6.9 (m, 2H), 3.45 (s, 2H) | 7.5 (m, 1H), 7.4 (m, 1H), 7.0 (m, 1H), 6.8 (d, 1H), 3.57 (s, 3H) | | 1.5 (s, 6H) | |
| RG-120149 | 300 MHz | CDCl3 | 7.45 (s, 1H), 7.22 (m, 1H), 6.5 (m, 1H) | 7.3 (d, 1H), 7.25 (s, 1H), 6.8 (d, 1H), 5.98 (s, 2H) | | 1.60 (s, 6H) | 7.8 (s, 1H) |
| RG-120081 | 300 MHz | CDCl3 | 7.3 (m, 3H), 7.15 (m, 2H), 3.5 (s, 2H) | 7.1 (m, 1H), 6.85 (s, 1H), 6.8 (d, 1H), 6.02 (s, 2H) | | 1.45 (s, 6H) | |
| RG-120145 | 300 MHz | CDCl3 | 7.35 (m, 3H), 7.18 (m, 2H), 4.45 (s, 2H), 4.0 (s, 2H) | 7.25 (m, 2H), 6.81 (d, 1H), 6.01 (s, 2H) | | 1.55 (s, 6H) | |
| RG-120076 | 300 MHz | CDCl3 | 7.1 (t, 1H), 6.9 (d, 1H), 6.6 (d, 1H), 3.80 (s, 3H) | 7.8 (m, 2H), 7.45 (m, 3H) | | 2.5 (br s, 2H), 1.9 (br s, 2H), 1.65 (br s, 3H), 1.15 (br s, 3H) | |
| RG-120100 | 300 MHz | CDCl3 | 7.45 (m, 1H), 7.2 (m, 1H), 6.5 (m, 1H) | 7.8 (m, 2H), 7.4 (m, 3H) | | 1.9 (m, 2H), 1.57 (s, 3H), 1.13 (t, 3H) | |
| RG-120146 | 300 MHz | CDCl3 | 3.46 (s, 2H) | | 7.8–7.0 (m, 10H) | 1.8 (m, 2H), 1.38 (br s, 3H), 1.0 (m, 3H) | 6.85 (s, 1H) |
| RG-120154 | 300 MHz | CDCl3 | 7.3 (m, 3H), 7.15 (m, 2H), 4.39 (s, 2H), 3.96 (s, 2H) | 7.75 (d, 2H), 7.45 (m, 3H) | | 1.85 (m, 2H), 1.51 (s, 3H), 1.09 (t, 3H) | |
| RG-120103 | 300 MHz | CDCl3 | 7.3 (m, 2H), 7.0 (t, 1H), 6.85 (d, 2H), 4.49 (s, 2H) | 7.7 (d, 2H), 7.4 (m, 3H) | | 1.85 (q, 2H), 1.47 (s, 3H), 1.08 (t, 3H) | 7.9 (s, 1H) |
| RG-120095 | 300 MHz | CDCl3 | | | 7.1–7.9 (m, 10H) | 1.97 (m, 2H), 1.52 (s, 3H), 1.15 (t, 3H) | 6.3 (br s, 1H) |
| RG-120133 | 300 MHz | CDCl3 | | | 7.8 (m, 5H), 7.4 (m, 5H) | 1.95 (m, 2H), 1.61 (s, 3H), 1.15 (t, 3H) | |
| RG-120118 | 300 MHz | CDCl3 | 7.6 (d, 2H), 7.5 (m, 1H), 7.4 (m, 2H) | 7.8 (d, 2H), 7.4 (m, 3H) | | 1.95 (m, 2H), 1.59 (s, 3H), 1.15 (t, 3H) | |
| RG-120137 | 300 MHz | CDCl3 | 7.6 (d, 2H), 7.2 (d, 2H), 2.7 (q, 2H), 1.22 (t, 3H) | 7.8 (m, 2H), 7.45 (m, 3H) | | 1.95 (m, 2H), 1.15 (t, 3H), 1.58 (s, 3H) | |
| RG-120058 | 300 MHz | CDCl3 | 7.1 (t, 1H), 6.9 (d, 1H), 6.6 (d, 1H), 3.95 (s, 3H), 2.45 (q, 2H), 1.0 (t, 3H) | 7.67 (s, 1H), 7.27 (s, 1H), 6.52 (s, 1H), 3.86 (s, 3H), 3.81 (s, 3H) | | 1.65 (s, 6H) | |
| RG-120102 | 300 MHz | CDCl3 | 7.45 (s, 1H), 7.15 (m, 1H), 6.55 (m, 1H) | 7.6 (s, 1H), 7.3 (s, 1H), 6.5 (m, 1H), 3.94 (s, 3H), 3.91 (s, 3H) | | 1.62 (s, 6H) | 8.1 (s, 1H) |
| RG-120078 | 300 MHz | CDCl3 | 7.35 (m, 2H), 7.1 (m, 3H), 3.44 (s, 2H) | 7.5 (s, 1H), 7.3 (s, 1H), 6.3 (s, 1H), 3.96 (s, 3H), 3.62 (s, 3H) | | 1.49 (s, 6H) | |
| RG-120110 | 300 MHz | CDCl3 | 7.37 (m, 3H), 7.22 (m, 2H), 4.45 (s, 2H), 3.97 (s, 2H) | 7.55 (s, 1H), 7.35 (s, 1H), 6.45 (s, 1H), 3.93 (s, 3H), 3.67 (s, 3H) | | 1.57 (s, 6H) | 8.2 (s, 1H) |
| RG-120079 | 300 MHz | CDCl3 | 7.22 (m, 2H), 7.05 (t, 1H), 6.75 (d, 2H), 4.47 (s, 2H) | 7.55 (s, 1H), 7.3 (s, 1H), 6.25 (s, 1H), 3.89 (s, 3H), 3.77 (s, 3H) | | 1.56 (s, 6H) | |

TABLE 4-continued

Physical Characterization of Compounds

| Compound | NMR frequency | Solvent | R¹ | R⁴ | R¹ + R⁴ | R² + R³ | NH |
|---|---|---|---|---|---|---|---|
| RG-120114 | 300 MHz | CDCl3 | 7.5 (m, 2H), 7.35 (m, 2H), 7.1 (t, 1H) | 7.7 (s, 1H), 7.45 (s, 1H), 6.5 (s, 1H), 3.93 (s, 3H), 3.82 (s, 3H) | | 1.76 (s, 3H), 1.52 (s, 3H) | 6.2 (s, 1H) |
| RG-120129 | 300 MHz | CDCl3 | 7.9 (m, 3H), 7.45 (m, 2H) | 7.8 (s, 1H), 7.65 (s, 1H), 6.5 (s, 1H), 3.95 (s, 3H), 3.90 (s, 3H) | | 1.6 (s, 6H) | |
| RG-120038 | 300 MHz | CDCl3 | 4.1 (m, 2H), 2.2–2.7 (m, 4H), 1.2 (t, 3H) | 7.5 (s, 1H),7.4 (s, 1H), 6.5 (s, 1H), 3.95 (s, 3H), 3.90 (s, 3H) | | 1.54 (s, 6H) | |
| RG-120096 | 300 MHz | CDCl3 | 7.6 (m, 2H), 7.5 (m, 1H), 7.4 (m, 1H) | 7.8 (s, 1H), 7.6 (s, 1H), 6.5 (s, 1H), 3.91 (s, 3H), 3.89 (s, 3H) | | 1.64 (s, 6H) | |
| RG-120135 | 300 MHz | CDCl3 | 7.55 (d, 2H), 7.25 (d, 2H), 2.7 (q, 2H), 1.23 (t, 3H) | 7.8 (s, 1H), 7.65 (s, 1H), 6.5 (s, 1H), 3.91 (s, 3H), 3.89 (s, 3H) | | 1.63 (s, 6H) | |
| RG-120023 | 300 MHz | CDCl3 | 7.15 (t, 1H), 7.9 (d, 1H), 6.65 (d, 1H), 3.81 (s, 3H), 2.6 (q, 2H), 1.05 (t, 1H) | 7.37 (d, 1H), 7.2 (s, 1H), 7.87 (d, 1H), 6.01 (s, 2H) | | 1.65 (br s, 6H) | |
| RG-120037 | 300 MHz | CDCl3 | 7.03 (m, 2H), 6.75 (m, 1H), 3.71 (s, 3H), 2.1, 2.05 (2s, 3H) | 7.1 (s, 2H), 7.05 (s, 1H), 2.2 (s, 6H) | | 7.0 (m, 2H), 6.95 (m, 2H), 2.8 (m, 1H), 2.65 (m, 1H), 2.22 (m, 4H) | 9.35 (s, 1H), 4.8 (br, 1H) |
| RG-120086 | 300 MHz | CDCl3 | 7.1 (m, 1H),6.9 (d, 1H), 6.65 (d, 1H), 3.8 (s, 3H), 2.05 (s, 3H) | 7.4 (s, 2H), 7.1 (s, 1H), 2.35 (s, 6H) | | 3.9 (m, 4H), 2.4 (m, 4H) | 8.5 (s, 1H) |
| RG-120051 | 300 MHz | CDCl3 | 7.5 (d, 2H), 7.35 (m, 1H), 7.2 (m, 2H) | 7.4 (d, 2H), 7.1 (s, 1H), 2.27 (s, 6H) | | 2.0 (m, 2H), 1.75, 1.6, 1.5 (3s, 3H), 1.2, 1.1 (2d, 3H) | 8.8 (br d, 1H), 6.25 (br t, 1H) |
| RG-120161 | 300 MHz | CDCl3 | 7.85 (m, 2H), 7.8 (s, 1H), 7.45 (m, 2H) | 7.4 (s, 2H), 7.05 (s, 1H), 2.27 (s, 6H) | | 1.95 (m, 2H), 1.60 (s, 3H), 1.15 (t, 3H) | 7.6 (s, 1H) |
| RG-120126 | 300 MHz | CDCl3 | 4.05 (q, 2H), 2.55 (br, 2H), 2.37 (m, 2H), 1.22 (t, 3H) | 7.3 (s, 2H), 7.1 (s, 1H), 2.31 (s, 6H) | | 1.85 (m, 2H), 1.52 (s, 3H), 1.1 (t, 3H) | |
| RG-120004 | 300 MHz | CDCl3 | | 7.3 (s, 2H), 7.1 (s, 1H), 2.3 (s, 6H) | | 1.9 (q, 2H), 1.53 (s, 3H), 1.1 (t, 3H) | |
| RG-120039 | 300 MHz | CDCl3 | 7.6 (d, 1H), 7.5 (t, 1H), 7.45 (d, 1H) | 7.4 (s, 2H), 7.05 (s, 1H), 2.28 (s, 6H) | | 1.95 (m, 2H), 1.58 (s, 3H), 1.14 (t, 3H) | |
| RG-120128 | 300 MHz | CDCl3 | 7.55 (d, 2H), 7.22 (d, 2H), 2.7 (q, 2H), 1.2 (t, 3H) | 7.4 (s, 2H), 7.05 (s, 1H), 2.23 (s, 6H) | | 1.9 (m, 2H), 1.57 (s, 3H), 1.15 (t, 3H) | |
| RG-120162 | 300 MHz | CDCl3 | 7.27 (m, 2H), 7.05 (t, 1H), 6.8 (d, 2H), 4.5 (s, 2H) | 7.65 (d, 2H), 7.35 (d, 2H) | | 1.55 (s, 6H) | 7.9 (s, 1H) |
| RG-120067 | 300 MHz | CDCl3 | 7.8 (s, 1H), 7.5 (d, 1H), 7.3 (m, 1H), 7.2 (t, 1H) | 7.75 (d, 2H), 7.4 (d, 2H) | | 1.73, 1.58 (2s, 6H) | 6.5 (s, 1H) |
| RG-120087 | 300 MHz | CDCl3 | 7.85 (t, 2H), 7.8 (s, 1H), 7.45 (t, 2H) | 7.75 (d, 2H), 7.4 (d, 2H) | | 1.65 (s, 6H) | |
| RG-120164 | 300 MHz | CDCl3 | 4.05 (q, 2H), 2.6 (br, 2H), 2.35 (t, 2H), 1.25 (t, 3H) | 7.72 (d, 2H), 7.35 (d, 2H) | | 1.55 (s, 6H) | |
| RG-120151 | 300 MHz | CDCl3 | 7.65 (d, 2H), 7.55 (t, 1H), 7.42 (m, 2H) | 7.7 (d, 2H), 7.4 (d, 2H) | | 1.65 (s, 6H) | 3.5 (br, 1H) |
| RG-120035 | 300 MHz | CDCl3 | 7.6 (d, 2H), 7.25 (d, 2H), 2.7 (q, 2H), 1.22 (t, 3H) | 7.72 (d, 2H), 7.35 (d, 2H) | | 1.63 (s, 6H) | |

TABLE 4-continued

Physical Characterization of Compounds

| Compound | NMR frequency | Solvent | R¹ | R⁴ | R¹ + R⁴ | R² + R³ | NH |
|---|---|---|---|---|---|---|---|
| RG-120045 | 300 MHz | CDCl3 | 7.1 (t, 1H), 6.85 (d, 1H), 6.65 (d, 1H), 3.78 (s, 3H), 2.07 (s, 3H) | 7.4 (s, 2H), 7.07 (s, 1H), 2.30 (s, 6H) | | 1.65 (s, 6H) | |
| RG-120042 | 300 MHz | CDCl3 | 7.1 (t, 1H), 6.85 (d, 1H), 6.6 (d, 1H), 3.78 (s, 3H), 1.99 (s, 3H) | 7.70 (d, 2H), 7.4 (m, 3H) | | 1.61 (s, 6H) | 7.75 (s, 1H) |
| RG-120115 | 200 MHz | CDCl3 | 7.6 (d, 2H), 7.2 (d, 2H), 2.7 (q, 2H), 1.2 (t, 3H) | 7.8 (m, 3H), 7.4 (m, 2H) | | 1.65 (s, 6H) | |
| RG-120003 | 300 MHz | CDCl3 | 7.4 (s, 1H), 7.22 (m, 1H), 6.5 (m, 1H) | 7.4 (s, 2H), 7.05 (s, 1H), 2.29 (s, 6H) | | 2.1 (m, 4H), 1.85 (m, 4H) | 7.8 (s, 1H) |
| RG-120073 | 300 MHz | CDCl3 | | 7.7 (d, 2H), 7.4 (d, 2H) | | 1.592 (s, 6H) | 3.5 (br, 1H) |
| RG-120005 | 300 MHz | CDCl3 | 7.55 (d, 2H), 7.2 (d, 2H), 2.7 (q, 2H), 1.2 (t, 3H) | 7.35 (s, 2H), 7.05 (s, 1H), 2.26 (s, 6H) | | 3.95 (br, 2H), 3.85 (m, 2H), 2.1 (br, 4H) | 7.8 (s, 1H) |
| RG-120008 | 300 MHz | CDCl3 | 7.15 (t, 1H), 2.4 (br, 2H), 0.98 (t, 3H) | 7.4 (s, 2H), 7.12 (s, 1H), 6.9 (d, 1H), 6.6 (d, 1H), 2.33 (s, 6H) | | 4.02 (br s, 2H), 3.9 (m, 2H), 2.1 (br, 4H) | |
| RG-120009 | 300 MHz | CDCl3 | 7.30 (br s, 3H), 7.12 (br s, 2H), 4.39 (s, 2H), 3.97 (s, 2H) | 7.35 (s, 2H), 7.15 (s, 1H), 2.32 (s, 6H) | | 3.95 (br s, 2H), 3.85 (m, 2H), 2.0 (br s, 4H) | 7.95 (s, 1H) |
| RG-120011 | 300 MHz | CDCl3 | 7.62 (m, 2H), 7.5 (m, 3H) | 7.45 (s, 2H), 7.05 (s, 1H), 2.28 (s, 6H) | | 2.12 (br s, 4H), 1.85 (br s, 4H) | |
| RG-120013 | 300 MHz | CDCl3 | 7.27 (m, 2H), 7.0 (t, 1H), 6.75 (d, 2H), 4.5 (s, 2H) | 7.75 (d, 2H), 7.45 (m, 3H) | | 3.95 (m, 2H), 3.85 (m, 2H), 2.0 (br s, 4H) | 7.9 (s, 1H) |
| RG-120014 | 300 MHz | CDCl3 | 4.05 (q, 2H), 2.55 (br, 2H), 2.35 (t, 2H), 1.23 (t, 3H) | 7.72 (m, 2H), 7.45 (m, 3H) | | 2.05 (br, 4H), 1.8 (br, 4H) | 3.55 (s, 1H) |
| RG-120019 | 300 MHz | CDCl3 | 7.6 (d, 2H), 7.5 (m, 1H), 7.4 (m, 2H) | 7.39 (s, 2H), 7.05 (s, 1H), 2.27 (s, 6H) | | 2.1 (br, 4H) | 7.75 (s, 1H) |
| RG-120020 | 300 MHz | CDCl3 | 7.1 (t, 1H), 6.9 (d, 1H), 6.65 (d, 1H), 3.79 (s, 3H), 2.55 (q, 2H), 1.0 (t, 3H) | 7.9 (d, 2H), 7.82 (d, 1H), 7.7 (d, 2H), 7.65 (d, 2H), 7.5 (m, 2H) | | 1.69 (br s, 6H) | |
| RG-120027 | 300 MHz | CDCl3 | 7.4 (m, 4H), 7.2 (m, 1H) | 7.7 (d, 2H), 7.5 (m, 3H) | | 4.05 (m, 2H), 3.85 (m, 2H), 2.05 (m, 4H) | 6.3 (s, 1H) |
| RG-120030 | 300 MHz | CDCl3 | 7.67 (d, 2H), 7.27 (m, 1H), 7.05 (m, 2H), 3.47 (s, 2H) | 7.5 (m, 2H), 7.35 (m, 3H) | | 1.95 (br s, 4H), 1.8 (m, 4H) | 6.87 (s, 1H) |
| RG-120031 | 300 MHz | CDCl3 | 4.0 (q, 2H), 1.22 (t, 3H), 2.6 (br, 2H), 2.35 (t, 2H) | 7.3 (s, 2H), 7.05 (s, 1H), 2.31 (s, 6H) | | 2.02 (br, 4H), 1.8 (m, 4H) | 7.5 (s, 1H) |
| RG-120034 | 300 MHz | CDCl3 | 7.35 (m, 3H), 7.15 (m, 2H), 4.40 (s, 2H), 3.95 (s, 2H) | 7.75 (d, 2H), 7.5 (m, 3H) | | 3.97 (br, 2H), 3.85 (m, 2H), 2.0 (br s, 4H) | 8.0 (s, 1H) |
| RG-120040 | 300 MHz | CDCl3 | 7.6 (d, 2H), 7.22 (d, 2H), 2.7 (q, 2H), 1.22 (t, 3H) | 7.45 (s, 2H), 7.05 (s, 1H), 2.27 (s, 6H) | | 2.1 (br, 4H), 1.8 (br, 4H) | |
| RG-120041 | 300 MHz | CDCl3 | 7.27 (t, 2H), 7.01 (t, 1H), 6.8 (d, 2H), 4.5 (s, 2H) | 7.35 (s, 2H), 7.1 (s, 1H), 2.30 (s, 6H) | | 2.05 (br s, 4H), 1.8 (m, 4H) | 7.95 (s, 1H) |
| RG-120044 | 300 MHz | CDCl3 | 7.4 (m, 5H) | 7.8 (d, 2H), 7.6 (d, 2H), 7.5 (m, 1H) | | 4.0 (br, 2H), 3.9 (t, 2H), 2.1 (br, 4H) | 7.7 (s, 1H) |
| RG-120046 | 300 MHz | CDCl3 | 7.3 (m, 3H), 7.05 (m, 2H), 3.5 (s, 2H) | 7.25 (s, 2H), 7.1 (s, 1H), 2.28 (s, 6H) | | 1.95 (br s, 4H), 1.75 (m, 4H) | |

TABLE 4-continued

Physical Characterization of Compounds

| Compound | NMR frequency | Solvent | R¹ | R⁴ | R¹ + R⁴ | R² + R³ | NH |
|---|---|---|---|---|---|---|---|
| RG-120048 | 300 MHz | CDCl3 | 7.27 (m, 2H), 7.0 (m, 1H), 6.75 (d, 2H), 4.5 (s, 2H) | 7.35 (s, 2H), 7.1 (s, 1H), 2.31 (s, 6H) | | 3.95 (m, 2H), 3.85 (m, 2H), 1.95 (br, 4H) | 7.9 (s, 1H) |
| RG-120049 | 300 MHz | CDCl3 | 7.15 (m, 1H), 6.9 (d, 1H), 6.65 (d, 1H), 3.80 (s, 3H), 2.5 (q, 2H), 1.0 (t, 3H) | 7.45 (s, 2H), 7.1 (s, 1H), 2.33 (s, 6H) | | 2.15 (br s, 4H), 1.85 (br s, 4H) | |
| RG-120050 | 300 MHz | CDCl3 | 7.30 (m, 3H), 7.12 (m, 2H), 4.4 (s, 2H), 3.9 (s, 2H) | 7.32 (s, 2H), 7.1 (s, 1H), 2.32 (s, 6H) | | 1.85 (m, 2H), 1.5 (s, 3H), 1.1 (t, 3H) | 7.9 (s, 1H) |
| RG-120052 | 300 MHz | CDCl3 | 7.3 (m, 3H), 7.15 (m, 2H), 4.4 (s, 2H), 3.97 (s, 2H) | 7.37 (s, 2H), 7.10 (s, 1H), 2.32 (s, 6H) | | 2.0 (br s, 4H), 1.8 (br s, 4H) | 7.93 (s, 1H) |
| RG-120054 | 300 MHz | CDCl3 | 7.5 (m, 2H), 7.4 (m, 3H) | 7.3 (s, 2H), 7.1 (s, 1H), 2.27 (s, 6H) | | 4.05 (m, 2H), 3.9 (m, 2H), 2.2 (m, 2H), 2.1 (m, 2H) | |
| RG-120063 | 300 MHz | CDCl3 | | 7.72 (m, 2H), 7.4 (m, 3H) | | 2.05 (br, 4H), 1.8 (br, 4H) | 3.55 (s, 1H) |
| RG-120069 | 300 MHz | CDCl3 | 7.1 (t, 1H), 6.9 (d, 1H), 6.65 (d, 1H), 3.80 (s, 3H), 2.65 (br, 2H), 1.05 (br t, 3H) | 7.41 (s, 2H), 7.1 (s, 1H), 2.33 (s, 6H) | | 1.95 (br, 2H), 1.65 (br s, 3H), 1.15 (br t, 3H), 1.05 (br t, 3H) | |
| RG-120071 | 300 MHz | CDCl3 | 7.47 (m, 1H), 7.2 (m, 1H), 6.52 (m, 1H) | 7.82 (m, 2H), 7.4 (m, 3H) | | 2.1 (br, 4H), 1.8 (br, 4H) | |
| RG-120082 | 300 MHz | CDCl3 | 7.45 (s, 1H), 7.2 (m, 1H), 6.5 (m, 1H) | 7.75 (d, 2H), 7.4 (d, 2H) | | 1.62 (s, 6H) | |
| RG-120084 | 300 MHz | CDCl3 | 7.25 (m, 3H), 7.0 (m, 2H), 3.45 (s, 2H) | 7.1 (s, 2H), 6.87 (s, 1H), 2.30 (s, 6H) | | 3.9 (m, 2H), 3.8 (m, 2H), 1.90 (br, 4H) | |
| RG-120089 | 300 MHz | CDCl3 | 7.8 (d, 2H), 7.4 (m, 3H) | 7.65 (d, 2H), 7.5 (m, 1H), 7.4 (m, 2H) | | 2.15 (br, 4H), 1.85 (br, 4H) | |
| RG-120090 | 300 MHz | CDCl3 | | 7.35 (s, 2H), 7.10 (s, 1H), 2.30 (s, 6H) | | 2.05 (m, 4H), 1.87 (m, 4H) | |
| RG-120092 | 300 MHz | CDCl3 | 7.10 (t, 1H), 6.85 (d, 1H), 6.6 (d, 1H), 3.80 (s, 3H), 2.5 (q, 2H), 1.0 (t, 3H) | 7.82 (d, 1H), 7.78 (d, 1H), 7.45 (m, 3H) | | 2.1 (m, 2H), 1.7–2.0 (m, 6H) | 7.18 (s, 1H) |
| RG-120099 | 300 MHz | CDCl3 | 7.73 (d, 2H), 7.42 (d, 2H), 7.15 (t, 1H), 3.81 (s, 3H), 2.5 (br, 2H), 1.0 (t, 3H) | 6.9 (d, 1H), 6.65 (d, 1H) | | 1.7 (br, 6H) | 7.2 (s, 1H) |
| RG-120106 | 300 MHz | CDCl3 | 7.92 (s, 1H), 7.22 (m, 1H), 6.5 (m, 1H) | 7.4 (s, 2H), 7.05 (s, 1H), 2.28 (s, 6H) | | 1.9 (m, 2H), 1.56 (s,3H), 1.13 (t, 3H) | 7.75 (s, 1H) |
| RG-120112 | 300 MHz | CDCl3 | 7.4 (m, 2H), 7.25 (m, 2H), 7.15 (t, 1H) | 7.5 (2s, 1H), 7.1 (s, 1H), 2.27 (s, 6H) | | 1.7–2.2 (m, 8H) | 6.3 (s, 1H), 7.8 (s, 1H) |
| RG-120117 | 300 MHz | CDCl3 | 7.35 (m, 3H), 7.2 (m, 2H), 4.45 (s, 2H), 4.0 (s, 2H) | 7.65 (d, 2H), 7.4 (d, 2H) | | 1.6 (s, 6H) | |
| RG-120120 | 300 MHz | CDCl3 | 7.23 (m, 3H), 7.05 (m, 2H), 3.45 (s, 2H) | 7.21 (s, 2H), 7.1 (s, 1H), 2.28 (s, 6H) | | 1.8 (br, 2H), 1.4 (br s, 3H), 1.05 (t, 3H) | 6.9 (s, 1H) |
| RG-120121 | 300 MHz | CDCl3 | 7.3 (m, 3H), 7.1 (m, 2H), 3.47 (s, 2H) | 7.55 (d, 2H), 7.35 (d, 2H) | | 1.47 (s, 6H) | 6.9 (s, 1H) |
| RG-120124 | 300 MHz | CDCl3 | 7.4 (d, 2H), 7.2 (d, 2H), 2.65 (q, 2H), 1.21 (t, 3H) | 7.8 (d, 2H), 7.55 (m, 3H) | - | 3.98 (m, 2H), 3.9 (m, 2H), 2.1 (br, 4H) | |

TABLE 4-continued

Physical Characterization of Compounds

| Compound | NMR frequency | Solvent | R¹ | R⁴ | R¹ + R⁴ | R² + R³ | NH |
|---|---|---|---|---|---|---|---|
| RG-120125 | 300 MHz | CDCl3 | 7.8 (d, 2H), 7.23 (d, 2H), 2.65 (q, 2H), 1.21 (t, 3H) | 7.6 (m, 3H), 7.4 (m, 2H) | | 2.1 (br, 4H), 1.8 (br, 4H) | |
| RG-120130 | 300 MHz | CDCl3 | 7.4 (m, 2H), 7.25 (m, 2H), 7.0 (m, 1H), 3.44 (s, 2H) | 7.8 (d, 1H), 7.65 (d, 2H), 7.5 (m, 2H) | | 3.8–4.0 (m, 4H), 1.85 (br m, 4H) | |
| RG-120132 | 300 MHz | CDCl3 | | | 7.1-7.7(m, 10H) | 1.8–2.3 (m, 8H) | 7.85 (s, 1H), 6.25 (s, 1H) |
| RG-120138 | 300 MHz | CDCl3 | 7.4 (m, 1H), 7.2 (m, 1H), 6.5 (m, 1H) | 7.4 (s, 2H), 7.07 (s, 1H), 2.29 (s, 6H) | | 3.95 (br, 2H), 3.85 (m, 2H), 2.05 (m, 4H) | 7.8 (s, 1H) |
| RG-120141 | 300 MHz | CDCl3 | 7.27 (t, 2H), 7.0 (t, 1H), 6.8 (d, 2H), 4.5 (s, 2H) | 7.32 (s, 2H), 7.1 (s, 1H), 2.3 (s, 6H) | | 1.8 (m, 2H), 1.45 (s, 3H), 0.9 (t, 3H) | 7.87 (s, 1H) |
| RG-120142 | 300 MHz | CDCl3 | 7.9 (d, 2H), 7.22 (d, 2H), 2.65 (q, 2H), 1.21 (t, 3H) | 7.45 (m, 2H), 7.4 (m, 2H), 7.6 (m, 5H) | | 1.66 (s, 6H) | |
| RG-120150 | 300 MHz | DMSO-d6 | 8.05 (br s, 1H), 7.99 (d, 1H), 7.92 (d, 1H), 7.75 (d, 1H), 7.3 (m, 1H) | 7.7 (m, 2H), 7.45 (m, 3H) | | 2.15 (br, 2H), 1.85 (br, 2H), 1.65 (br s, 4H) | 4.6 (s, 1H) |
| RG-120152 | 300 MHz | CDCl3 | 7.8 (m, 3H), 7.40 (m, 2H) | 7.45 (s, 2H), 7.05 (s, 1H), 2.27 (s, 6H) | | 2.05 (m, 4H), 1.85 (m, 4H) | |
| RG-120155 | 300 MHz | CDCl3 | 7.4 (m, 3H), 7.15 (m, 2H), 4.40 (s, 2H), 4.0 (s, 2H) | 7.77 (d, 2H), 7.3 (m, 3H) | | 2.05 (br s, 4H), 1.8 (br s, 4H) | 7.95 (s, 1H) |
| RG-120158 | 300 MHz | CDCl3 | 7.77 (d, 2H), 7.02 (t, 1H), 6.8 (d, 2H), 4.49 (s, 2H) | 7.42 (m, 3H), 7.3 (m, 2H) | | 2.05 (br s, 4H), 1.8 (m, 4H) | 7.95 (s, 1H) |
| RG-120159 | 300 MHz | CDCl3 | 7.1 (t, 1H), 6.9 (d, 1H), 6.55 (d, 1H), 2.4 (br, 2H), 0.95 (t, 3H) | 7.8 (m, 2H), 7.5 (m, 3H) | | 4.0 (m, 2H), 3.9 (m, 2H), 2.1 (m, 2H), 1.9 (m, 2H) | 7.22 (s, 1H) |
| RG-121517 | 500 MHz | CDCl3 | 6.55 (d, 1H), 6.45 (d, 1H), 4.3 (m, 4H), 2.55 (m, 2H), 1.05 (t, 3H) | 7.8 (m, 2H), 7.45 (m, 3H) | | 1.62 (s, 6H) | |
| RG-121518 | 500 MHz | CDCl3 | 6.73 (d, 1H), 6.64 (d, 1H), 4.3 (m, 4H), 2.6 (br, 2H), 1.14 (t, 3H) | 7.31 (s, 1H), 7.1 (s, 2H) | | 2.33 (s, 6H), 1.8 (m, 2H), 1.49 (s, 3H), 1.03 (t, 3H) | 7.4 (br s, 1H) |
| RG-121513 | 500 MHz | CDCl3 | 7.9 (t, 1H), 7.2 (d, 1H), 6.95 (d, 1H), 2.7 (q, 2H), 1.13 (t, 3H) | 7.37 (s, 2H), 7.0 (s, 1H), 2.3 (s, 6H) | | 1.9 (m, 2H), 1.57 (s, 3H), 1.22 (t, 3H) | |
| RG-121514 | 500 MHz | CDCl3 | 8.1 (d, 1H), 7.9 (t, 1H), 7.1 (d, 1H), 6.95 (d, 1H), 2.65 (q, 2H), 1.2 (t, 3H) | 7.8 (d, 2H), 7.4 (m, 3H) | | 2.1 (br s, 4H), 1.9 (m, 2H), 1.8 (m, 2H) | |
| RG-121515 | 500 MHz | CDCl3 | 8.0 (d, 1H [NH]), 7.9 (m, 1H), 7.1 (m, 1H), 6.95 (d, 2H), 2.7 (q, 2H), 1.2 (t, 3H) | 7.4 (s, 2H), 7.05 (s, 1H), 2.28 (s, 6H) | | 2.1 (br s, 4H), 1.87 (m, 2H), 1.75 (m, 2H) | |
| RG-121516 | 500 MHz | CDCl3 | 8.05 (d 1H [NH]), 7.9 (m, 1H), 7.1 (d, 1H), 6.9 (d, 1H), 2.65 (q, 2H), 1.2 (t, 3H) | 7.8 (m, 2H), 7.4 (m, 3H) | | 1.65 (s, 6H) | |

Example 2

Biological Testing of Compounds

The ligands of the present invention are useful in various applications including gene therapy, expression of proteins of interest in host cells, production of transgenic organisms, and cell-based assays.

27-63 Assay

Gene Expression Cassette

GAL4 DBD (1-147)-CƒEcR(DEF)/VP16AD-βRXREF-LmUSPEF: The wild-type D, E, and F domains from spruce budworm *Choristoneura fumiferana* EcR ("CfEcR-DEF"; SEQ ID NO: 1) were fused to a GAL4 DNA binding domain ("Gal4DBD1-147"; SEQ ID NO: 2) and placed under the control of a phosphoglycerate kinase promoter ("PGK"; SEQ ID NO: 3). Helices 1 through 8 of the EF domains from *Homo sapiens* RXRβ ("HsRXRβ-EF"; nucleotides 1-465 of SEQ ID NO: 4) and helices 9 through 12 of the EF domains of *Locusta migratoria* Ultraspiracle Protein ("LmUSP-EF"; nucleotides 403-630 of SEQ ID NO: 5) were fused to the transactivation domain from VP16 ("VP16AD"; SEQ ID NO: 6) and placed under the control of an elongation factor-1α promoter ("EF-1α"; SEQ ID NO: 7). Five consensus GAL4 response element binding sites ("5× GAL4RE"; comprising 5 copies of a GAL4RE comprising SEQ ID NO: 8) were fused to a synthetic TATA minimal promoter (SEQ ID NO: 9) and placed upstream of the luciferase reporter gene (SEQ ID NO: 10).

Stable Cell Line

CHO cells were transiently transfected with transcription cassettes for GAL4 DBD (1-147) CƒEcR(DEF) and for VP16AD βRXREF-LmUSPEF controlled by ubiquitously active cellular promoters (PGK and EF-1α, respectively) on a single plasmid. Stably transfected cells were selected by Zeocin resistance. Individually isolated CHO cell clones were transiently transfected with a GAL4 RE-luciferase reporter (pFR Luc). 27-63 clone was selected using Hygromycin.

Treatment with Ligand

Cells were trypsinized and diluted to a concentration of 2.5×104 cells mL. 100 μL of cell suspension was placed in each well of a 96 well plate and incubated at 37° C. under 5% $CO_2$ for 24 h. Ligand stock solutions were prepared in DMSO and diluted 300 fold for all treatments. Dose response testing consisted of 8 concentrations ranging from 33 μM to 0.01 μM.

Reporter Gene Assay

Luciferase reporter gene expression was measured 48 h after cell treatment using Bright-Glo™ Luciferase Assay System from Promega (E2650). Luminescence was detected at room temperature using a Dynex MLX microtiter plate luminometer.

Z3 Assay

Stable Cell Line

Dr. F. Gage provided a population of stably transformed cells containing CVBE and 6×EcRE as described in Suhr, S. T., Gil, E. B., Senut M. C., Gage, F. H. (1998) Proc. Natl. Acad. Sci. USA 95, 7999-804. Human 293 kidney cells, also referred to as HEK-293 cells, were sequentially infected with retroviral vectors encoding first the switch construct CVBE, and subsequently the reporter construct 6×EcRE Lac Z. The switch construct contained the coding sequence for amino acids 26-546 from *Bombyx mori* EcR (BE) (Iatrou) inserted in frame and downstream of the VP16 transactivation domain (VBE). A synthetic ATG start codon was placed under the control of cytomegalovirus (CVBE) immediate early promoter and flanked by long terminal repeats (LTR). The reporter construct contained six copies of the ecdysone response element (EcRE) binding site placed upstream of LacZ and flanked on both sides with LTR sequences (6×EcRE).

Dilution cloning was used to isolate individual clones. Clones were selected using 450 ug/mL G418 and 100 ng/mL puromycin. Individual clones were evaluated based on their response in the presence and absence of test ligands. Clone Z3 was selected for screening and SAR purposes.

Human 293 kidney cells stably transformed with CVBE and 6×EcRE LacZ were maintained in Minimum Essential Medium (Mediates, 10-010-CV) containing 10% FBS (Life Technologies, 26140-087), 450 gum G418 (Mediates, 30-234-CR), and 100 gnome promising (Sigma, P-7255), at 37° C. in an atmosphere containing 5% $CO_2$ and were subculture when they reached 75% confluence.

Treatment with Ligand

Z3 cells were seeded into 96-well tissue culture plates at a concentration of 2.5×10$^3$ cells per well and incubated at 37° C. in 5% $CO_2$ for twenty-four hours. Stock solutions of ligands were prepared in DMSO. Ligand stock solutions were diluted 100 fold in media and 50 μL of this diluted ligand solution (33 μM) was added to cells. The final concentration of DMSO was maintained at 0.03% in both controls and treatments.

Reporter Gene Assays

Reporter gene expression was evaluated 48 hours after treatment of cells, β-galactosidase activity was measured using Gal Screen™ bioluminescent reporter gene assay system from Tropix (GSY1000). Fold induction activities were calculated by dividing relative light units ("RLU") in ligand treated cells with RLU in DMSO treated cells. Luminescence was detected at room temperature using a Dynex MLX microtiter plate luminometer.

A schematic of switch construct CVBE, and the reporter construct 6×EcRE Lac Z is shown in FIG. 1. Flanking both constructs are long terminal repeats, G418 and puromycin are selectable markers, CMV is the cytomegalovirus promoter, VBE is coding sequence for amino acids 26-546 from *Bombyx mori* EcR inserted downstream of the VP16 transactivation domain, 6×EcRE is six copies of the ecdysone response element, lacZ encodes for the reporter enzyme β-galactosidase.

13B3 Assay

Gene Expression Cassette

GAL4 DBD-CƒEcR(DEF)/VP16AD-MmRXRE: The wild-type D, E, and F domains from spruce budworm *Choristoneura fumiferana* EcR ("CfEcR-DEF"; SEQ ID NO: 1) were fused to a GAL4 DNA binding domain ("Gal4DBD1-147"; SEQ ID NO: 2) and placed under the control of the SV40e promoter of pM vector (PT3119-5, Clontech, Palo Alto, Calif.). The D and E domains from *Mus Musculus* RXR ("MmRXR-DE"; SEQ ID NO: 11) were fused to the transactivation domain from VP16 ("VP16AD"; SEQ ID NO: 6) and placed under the control of the SV40e promoter of the pVP16 vector (PT3127-5, Clontech, Palo Alto, Calif.).

Stable Cell Line

CHO cells were transiently transfected with transcription cassettes for GAL4 DBD-CfEcR(DEF) and for VP16AD-MmRXRE controlled by SV40e promoters. Stably transfected cells were selected using Hygromycin. Individually isolated CHO cell clones were transiently transfected with a GAL4 RE-luciferase reporter (pFR-Luc, Stratagene, La Jolla, Calif.). The 13B3 clone was selected using Zeocin.

Treatment with Ligand

Cells were trypsinized and diluted to a concentration of $2.5 \times 10^4$ cells mL. 100 µL of cell suspension was placed in each well of a 96 well plate and incubated at 37° C. under 5% $CO_2$ for 24 h. Ligand stock solutions were prepared in DMSO and diluted 300 fold for all treatments. Dose response testing consisted of 8 concentrations ranging from 33 µM to 0.01 µJM.

Reporter Gene Assay

Luciferase reporter gene expression was measured 48 h after cell treatment using Bright-Glo™ Luciferase Assay System from Promega (E2650). Luminescence was detected at room temperature using a Dynex MLX microtiter plate luminometer.

The results of the assays are shown in Tables 5 and 6. Each assay was conducted in two separate wells, and the two values were averaged. Fold inductions were calculated by dividing relative light units ("RLU") in ligand treated cells with RLU in DMSO treated cells. $EC_{50}s$ were calculated from dose response data using a three-parameter logistic model. Relative Max FI was determined as the maximum fold induction of the tested ligand (an embodiment of the invention) observed at any concentration relative to the maximum fold induction of GS™-E ligand (3,5-Dimethyl-benzoic acid N-tert-butyl-N'-(2-ethyl-3-methoxy-benzoyl)-hydrazide) observed at any concentration.

TABLE 5

Biological Assay Results for Compounds: Fold Induction

| Compound | 13B3 assay 33/33.3 (µM) | 27-63 assay 33.3 (µM) | Z3 assay 33 (µM) |
|---|---|---|---|
| RG-103441 | 1.6 | | 0.8 |
| RG-103468 | 2.2 | | 1.1 |
| RG-120001 | 3.3 | | 0.3 |
| RG-120002 | 0.2 | 5.7 | 3.9 |
| RG-120005 | | | 0.8 |
| RG-120006 | 1.1 | | 0.5 |
| RG-120008 | 0.0 | | 567.3 |
| RG-120009 | 1.3 | | 0.8 |
| RG-120012 | 0.7 | | 0.7 |
| RG-120014 | 0.0 | | 1.1 |
| RG-120015 | 0.0 | | 0.8 |
| RG-120016 | 4.4 | 1146.6 | 226.9 |
| RG-120017 | 0.8 | | 0.9 |
| RG-120018 | 0.8 | | 0.7 |
| RG-120019 | | | 1.5 |
| RG-120020 | 1.3 | | 0.2 |
| RG-120021 | 0.0 | | 0.7 |
| RG-120022 | 0.0 | 0.3 | 0.1 |
| RG-120023 | 0.0 | 1.4 | 0.2 |
| RG-120024 | 2.1 | 6.3 | 3.8 |
| RG-120025 | 0.9 | | 0.8 |
| RG-120026 | 0.9 | 8.5 | 41.1 |
| RG-120029 | 1.5 | | 0.7 |
| RG-120033 | 0.9 | | 0.7 |
| RG-120035 | 1.2 | | 9.1 |
| RG-120037 | 0.3 | 0.4 | 0.5 |
| RG-120038 | 0.0 | | 0.2 |
| RG-120040 | 174.4 | 241.6 | 202.3 |

TABLE 5-continued

Biological Assay Results for Compounds: Fold Induction

| Compound | 13B3 assay 33/33.3 (µM) | 27-63 assay 33.3 (µM) | Z3 assay 33 (µM) |
|---|---|---|---|
| RG-120042 | 3.3 | | 19.3 |
| RG-120045 | 1412.3 | 2707.3 | 275.8 |
| RG-120046 | 1.3 | | 8.9 |
| RG-120047 | 973.9 | | 31.9 |
| RG-120048 | 0.0 | | 1.0 |
| RG-120049 | 2661.5 | 2070.7 | 310.0 |
| RG-120050 | 0.9 | | 3.5 |
| RG-120052 | 0.7 | | 4.9 |
| RG-120055 | 0.7 | 0.5 | 0.2 |
| RG-120056 | 0.1 | | 1.0 |
| RG-120057 | 0.6 | | 0.8 |
| RG-120058 | 0.3 | 0.3 | 1.7 |
| RG-120059 | 0.0 | | 0.6 |
| RG-120060 | 16.8 | | 108.5 |
| RG-120061 | 0.4 | 0.9 | 0.6 |
| RG-120062 | 0.2 | | 0.6 |
| RG-120066 | 1.4 | | 0.6 |
| RG-120067 | 2.6 | | 0.5 |
| RG-120069 | 477.7 | 1872.1 | |
| RG-120070 | 0.4 | | 0.7 |
| RG-120072 | 0.6 | | 1.3 |
| RG-120073 | 0.9 | | 0.5 |
| RG-120075 | 1.1 | | 0.7 |
| RG-120076 | 20.2 | 4091.3 | 0.2 |
| RG-120077 | 0.4 | | 14.6 |
| RG-120078 | 0.0 | | 0.4 |
| RG-120079 | 0.7 | | 0.6 |
| RG-120080 | 716.9 | | 310.4 |
| RG-120081 | 0.5 | | 0.6 |
| RG-120082 | 0.1 | | 0.8 |
| RG-120083 | 1.3 | | 0.8 |
| RG-120086 | 4.0 | | 111.6 |
| RG-120087 | 0.4 | | 0.4 |
| RG-120088 | 0.9 | | 8.2 |
| RG-120091 | 0.5 | | 1.5 |
| RG-120092 | | 2186.5 | |
| RG-120093 | 0.0 | 5.0 | 0.2 |
| RG-120094 | 0.6 | | 0.8 |
| RG-120096 | 0.2 | | 0.7 |
| RG-120098 | 0.3 | | 1.8 |
| RG-120099 | 0.0 | 1327.0 | 0.2 |
| RG-120101 | 1.2 | | 0.7 |
| RG-120102 | 0.5 | | 0.8 |
| RG-120105 | 0.5 | | 0.8 |
| RG-120108 | 0.0 | | 0.3 |
| RG-120109 | 0.0 | | 0.2 |
| RG-120110 | 0.8 | | 0.5 |
| RG-120111 | 0.6 | | 0.7 |
| RG-120113 | 3.4 | | 0.6 |
| RG-120114 | 1.1 | | 0.6 |
| RG-120115 | 0.8 | | 9.1 |
| RG-120117 | 1.2 | | 0.8 |
| RG-120118 | 0.8 | 13.4 | 1.4 |
| RG-120119 | 0.4 | | 0.8 |
| RG-120121 | 0.1 | | 0.7 |
| RG-120122 | 0.5 | | 0.6 |
| RG-120124 | 1.2 | 1.0 | 2.0 |
| RG-120125 | 82.6 | 509.9 | 253.6 |
| RG-120126 | 0.4 | | 2.4 |
| RG-120127 | 0.6 | | 0.7 |
| RG-120128 | 129.0 | 338.2 | 403.0 |
| RG-120129 | 0.9 | | 0.4 |
| RG-120134 | 0.3 | | 0.6 |
| RG-120135 | 0.4 | 0.7 | 0.7 |
| RG-120136 | 0.3 | | 0.6 |
| RG-120137 | 5.3 | 4.6 | 59.0 |
| RG-120140 | 1.4 | | 0.5 |
| RG-120142 | 0.3 | | 0.4 |
| RG-120144 | 0.1 | | 0.7 |
| RG-120145 | 1.4 | | 0.5 |
| RG-120147 | 1.1 | | 1.0 |
| RG-120148 | 0.0 | 0.7 | 1.1 |

TABLE 5-continued

Biological Assay Results for Compounds: Fold Induction

| | Fold Induction Average | | |
|---|---|---|---|
| Compound | 13B3 assay 33/33.3 (µM) | 27-63 assay 33.3 (µM) | Z3 assay 33 (µM) |
| RG-120149 | 1.1 | | 0.7 |
| RG-120151 | 0.3 | | 0.8 |
| RG-120152 | 264.3 | | 59.9 |
| RG-120153 | 0.8 | | 0.7 |
| RG-120156 | 1.4 | | 0.7 |
| RG-120157 | 0.0 | | 0.9 |
| RG-120159 | 0.1 | 3.7 | 0.2 |
| RG-120160 | 0.3 | | 0.6 |
| RG-120161 | 59.9 | | |
| RG-120162 | 0.9 | | 0.7 |
| RG-120163 | 1.1 | | 0.5 |
| RG-120164 | 1.7 | | 0.6 |
| RG-120326 | 0.0 | | |
| RG-121513 | | 1015.2 | |
| RG-121514 | | 1.7 | |
| RG-121515 | | 36.6 | |
| RG-121516 | | 7.9 | |
| RG-121517 | | 3514.1 | |
| RG-121518 | | 2336.5 | |

TABLE 6

Biological Assay Results for Compounds: EC50/Relative Max FI

| Compound | EC50 (µM)/Rel Max FI 13B3 assay | EC50 (µM)/Rel Max FI 27-63 assay | EC50 (µM)/Rel Max FI Z3 assay |
|---|---|---|---|
| RG-120002 | | >33/0 | |
| RG-120005 | | >33/0 | |
| RG-120016 | | ~20/0.71 | |
| RG-120019 | | >33/0 | |
| RG-120022 | | >33/0 | |
| RG-120023 | | >33/0 | |
| RG-120024 | | >33/0 | |
| RG-120026 | | >33/0 | |
| RG-120037 | | >33/0 | |
| RG-120040 | | ~20/0.13 | |
| RG-120042 | | >33/0 | |
| RG-120045 | | ~20/1.25 | |
| RG-120049 | 3.57/1.56 | 3.42/1.58 | 1.6/0.88 |
| RG-120055 | | >33/0 | |
| RG-120058 | | >33/0 | |
| RG-120060 | | >33/0.01 | |
| RG-120061 | | >33/0 | |
| RG-120069 | 2.95/1.02 | 3.31/1.11 | 1.68/0.8 |
| RG-120076 | >33.3/0.05 | ~20/1.4 | 12.43/0.9 |
| RG-120080 | 12.35/1.04 | 8.35/1.29 | 3.95/0.71 |
| RG-120092 | | 7.16/1.15 | |
| RG-120093 | | >33/0 | |
| RG-120096 | >33.3/0 | | >50/0 |
| RG-120099 | | ~20/0.64 | |
| RG-120115 | | >33/0 | |
| RG-120118 | | >33/0 | |
| RG-120124 | | >33/0 | |
| RG-120125 | >33.3/0.16 | ~20/0.27 | 10.02/0.67 |
| RG-120126 | >33.3/0 | | >50/0.04 |
| RG-120128 | | ~20/0.18 | |
| RG-120135 | | >33/0 | |
| RG-120137 | | >33/0 | |
| RG-120148 | | >33/0 | |
| RG-120159 | | >33/0 | |
| RG-120161 | 3.46/0.14 | | 2.14/0.08 |
| RG-121513 | | ~10/0.44 | |
| RG-121514 | | 3.89/0.5 | |
| RG-121515 | | ~5/0.17 | |

TABLE 6-continued

Biological Assay Results for Compounds: EC50/Relative Max FI

| Compound | EC50 (µM)/Rel Max FI 13B3 assay | EC50 (µM)/Rel Max FI 27-63 assay | EC50 (µM)/Rel Max FI Z3 assay |
|---|---|---|---|
| RG-121516 | | >33/0 | |
| RG-121517 | | ~20/1.55 | |
| RG-121518 | | 3.57/1.08 | |

Example 3

Insecticidal Activity of Compounds

The compound to be evaluated was dissolved in an appropriate solvent, usually a mix of acetone, methanol, and water. Test solutions were made by serial dilution of a stock test solution with acetone, methanol, and water. Initial evaluations were made at one or more concentrations on one or more of the following insects:

| Code Symbol | Common Name | Latin Name |
|---|---|---|
| BAW | Beet Armyworm | *Spodoptera exigua* |
| CL | Cabbage Looper | *Trichoplusia ni* |
| TBW | Tobacco Budworm | *Heliothis virescens* |

Feeding bioassays were conducted in bioassay trays containing insect diet. Treatments were made by applying 50 µL of test solution to the surface of the diet in each of 5 wells. After the test solution dried, each well was infested with a single neonate larva. The trays were held for six days and then the mortality rating was determined for each treatment.

Contact bioassays (green peach aphid, two-spotted spider mite, white fly) were conducted by applying a solution of the test compound to the inside surface of a Petri dish. The solution was allowed to air-dry, then each dish was infested and the larvae from each treatment were transferred to a bioassay tray. The trays were held for one to seven days, and the mortality rating was determined for each treatment.

Some of the tobacco budworm tests were conducted as follows. A test solution containing 600 ppm was made by dissolving a compound of the invention in a 1:1 acetone:methanol solution, then adding water to give a 5:5:90 acetone:methanol:water solution, and finally a surfactant was added at an equivalent of 7.37 g of surfactant per 100 L of test solution (1 ounce of surfactant per 100 gallons of test solution). Appropriate dilutions were prepared in water from the 600 ppm solution. A detached cotton leaf, *Gossypium hirsutum* was placed on moistened filter paper in a Petri dish (100×20 mms). The leaf was sprayed with the test solution using a rotating turntable sprayer and allowed to dry. The dish was infested with 10 first instar larvae of the tobacco budworm and covered with the lid. If the larvae were alive two days after treatment, fresh untreated cotton leaves were added. All treatments were maintained at 23.9-26.7° C. (75-80° F) under fluorescent light in a well-ventilated room. Percent mortality was determined at four days after treatment.

TABLE 7

Insecticidal Activity Assay Results for Compounds

| Compound | CfEcR (CDEF)/CfUSP, GST fusion protein CfEcR EC50 | Insect Toxicity (LC50 (ppm) or % control @ 150 ppm) | | | | |
|---|---|---|---|---|---|---|
| | | MTA | BAW | CL | TBW | WFN |
| RG-120096 | 6% @ 10 uM | 74 @ 150 | 0% @ 150 | 60% @ 150 | 0% @ 150 | 55% @ 150 |
| RG-120076 | 8.35 nM | 92 | 47 | 47 | >150 | >150 |
| RG-120128 | 28.5 nM | >150 | 47 | 17 | >150 | >150 |
| RG-120039 | 203 nM (28% @ 1 uM) | | | | | |
| RG-120126 | 136 nM (21% @ 1 uM) | 0% @ 150 | 0% @ 150 | 0% @ 150 | 0% @ 150 | 79% @ 150 |
| RG-120008 | 81% @ 1 uM | | | | | |
| RG-120080 | Kd = 11.9 nM | 0% @ 150 | 23 | 47 | >150 | 0% @ 150 |
| RG-120060 | Kd = 38 nM | 0% @ 150 | 23 | 47 | >150 | 0% @ 150 |
| RG-120161 | 62.4 nM | 110 | 87 | 17 | >150 | >150 |
| RG-120051 | 147 nM | | | | | |
| RG-120069 | 14.2 nM | 146 | 4.7 | 4.7 | >150 | >150 |
| RG-120125 | 57.9 nM | 167 | 98 | 23 | >150 | 150 |
| RG-120092 | 99% @ 1 uM | >150 | 47 | 13 | 98 | >150 |
| RG-120152 | 92% @ 1 uM | | | | | |
| RG-120035 | | 0% @ 150 | 40% @ 150 | 100% @ 150 | 0% @ 150 | 0% @ 150 |
| RG-120099 | | 0% @ 150 | 100% @ 150 | 40% @ 150 | 0% @ 150 | 0% @ 150 |
| RG-120015 | | 0% @ 150 | 80% @ 150 | 0% @ 150 | 0% @ 150 | 0% @ 150 |
| RG-120001 | | 0% @ 150 | 80% @ 150 | 20% @ 150 | 0% @ 150 | 0% @ 150 |
| RG-120021 | | 51% @ 150 | 100% @ 150 | 0% @ 150 | 0% @ 150 | 0% @ 150 |
| RG-120026 | | 40% @ 150 | 100% @ 150 | 0% @ 150 | 0% @ 150 | 0% @ 150 |
| RG-120042 | 481 nM (Plodia EC50); 29 uM (Kc EC50) | | | | | |
| RG-120115 | | inactive as insecticide | | | | |
| RG-120077 | | 0% @ 150 | 50% @ 150 | 100% @ 150 | 0% @ 150 | 0% @ 150 |

In addition, one of ordinary skill in the art is also able to predict that the ligands disclosed herein will also work to modulate gene expression in various cell types described above using gene expression systems based on group H and group B nuclear receptors.

What is claimed is:

1. A compound of the general formula:

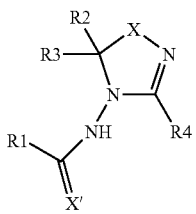

wherein X is O and X' is O or S;

R[1] is a) H, $(C_1-C_6)$alkyl, $(C_1-C_6)$haloalkyl, $(C_1-C_6)$cyanoalkyl, $(C_1-C_6)$alkoxycarbonyl$(C_1-C_6)$alkyl, $(C_1-C_6)$alkoxy, or benzyloxy;

b) unsubstituted or substituted phenyl wherein the substituents are independently 1 to 5 H; halo; nitro; cyano; hydroxy; amino (—NR$^a$R$^b$); $(C_1-C_6)$alkyl; $(C_1-C_6)$haloalkyl; $(C_1-C_6)$cyanoalkyl; $(C_1-C_6)$hydroxyalkyl; $(C_1-C_6)$alkoxy; phenoxy; $(C_1-C_6)$haloalkoxy; $(C_1-C_6)$alkoxy$(C_1-C_6)$alkyl; $(C_1-C_6)$alkoxy$(C_1-C_6)$alkoxy; $(C_1-C_6)$alkanoyloxy$(C_1-C_6)$alkyl; $(C_2-C_6)$alkenyl optionally substituted with halo, cyano, $(C_1-C_4)$ alkyl, or $(C_1-C_4)$alkoxy; $(C_2-C_6)$alkynyl optionally substituted with halo or $(C_1-C_4)$alkyl; formyl; carboxy; $(C_1-C_6)$alkylcarbonyl; $C_1-C_6)$haloalkylcarbonyl; benzoyl; $(C_1-C_6)$alkoxycarbonyl; $(C_1-C_6)$haloalkoxycarbonyl; $(C_1-C_6)$alkanoyloxy (—OCOR$^a$); carboxamido (—CONR$^a$R$^b$); amido (—NR$^a$COR$^b$); alkoxycarbonylamino (—NR$^a$CO$_2$R$^b$); alkylaminocarbonylamino (—NR$^a$CONR$^b$R$^c$); mercapto; $(C_1-C_6)$alkylthio; $(C_1-C_6)$alkylsulfonyl; $(C_1-C_6)$alkylsulfoxido (—S(O)R$^a$); sulfamido (—SO$_2$NR$^a$R$^b$); or unsubstituted or substituted phenyl wherein the substituents are independently 1 to 3 halo, nitro, $(C_1-C_6)$alkoxy, $(C_1-C_6)$alkyl, or amino; or when two adjacent positions on the phenyl ring are substituted with alkoxy groups, these groups, together with the carbon atoms to which they are attached, may be joined as a linkage (—OCH$_2$O—) or (—OCH$_2$CH$_2$O—) to form a 5- or 6-membered dioxolano or dioxano heterocyclic ring;

c) unsubstituted or substituted naphthyl wherein the substituents are independently 1 to 3 halo, nitro, $(C_1-C_6)$alkoxy, $(C_1-C_6)$alkyl, or amino;

d) unsubstituted or substituted benzothiophene-2-yl, benzothiophene-3-yl, benzofuran-2-yl, or benzofuran-3-yl wherein the substituents are independently 1 to 3 halo, nitro, hydroxy, $(C_1-C_6)$alkyl, $(C_1-C_6)$alkoxy, carboxy, or $(C_1-C_6)$alkoxycarbonyl (—CO$_2$R$^a$);

e) unsubstituted or substituted 2, 3, or 4-pyridyl wherein the substituents are independently 1 to 3 halo, cyano, nitro, hydroxy, $(C_1-C_6)$alkyl, $(C_1-C_6)$alkoxy, or $(C_1-C_6)$haloalkoxy;

f) unsubstituted or substituted 5-membered heterocycle selected from furyl, thiophenyl, triazolyl, pyrrolyl, isopyrrolyl, pyrazolyl, isoimidazolyl, thiazolyl, isothiazolyl, oxazolyl, or isooxazolyl wherein the substituents are independently 1 to 3 halo, nitro, hydroxy, $(C_1-C_6)$alkyl, $(C_1-C_6)$alkoxy, carboxy, $(C_1-C_6)$alkoxycarbonyl (—CO$_2$R$^a$), or unsubstituted or substituted phenyl wherein the substituents are independently 1 to 3 halo, nitro, $(C_1-C_6)$alkyl, $(C_1-C_6)$haloalkyl, $(C_1-C_6)$alkoxy, $(C_1-C_6)$haloalkoxy, carboxy, $(C_1-C_4)$alkoxycarbonyl (—CO$_2$R$^a$), or amino (—NR$^a$R$^b$);

g) aromatic-substituted or unsubstituted phenyl$(C_1-C_6)$alkyl, phenyl$(C_1-C_6)$alkoxy$(C_1-C_6)$alkyl, or phenoxy $(C_1-C_6)$alkyl wherein the aromatic substituents are independently 1 to 3 halo, nitro, $(C_1-C_6)$alkoxy, $(C_1-C_6)$alkyl, or amino; or h) aromatic-substituted phenylamino, phenyl$(C_1-C_6)$alkylamino, or phenylcarbonylamino wherein the aromatic substituents are independently 1 to 3 halo, nitro, $(C_1-C_6)$alkoxy, $(C_1-C_6)$alkyl, or amino;

wherein R$^a$, R$^b$, and R$^c$ are independently H, $(C_1-C_6)$alkyl, or phenyl;

R$^2$ and R$^3$ are independently H, $(C_1-C_6)$alkyl, $(C_1-C_6)$haloalkyl, $(C_1-C_6)$cyanoalkyl, $(C_1-C_6)$hydroxyalkyl, $(C_1-C_6)$alkoxy$(C_1-C_6)$alkyl, phenyl, or together as an alkane linkage (—(CH$_2$)$_x$—), an alkyloxylalkyl linkage (—(CH$_2$)$_y$O(CH$_2$)$_z$—), an alkylaminoalkyl linkage (—(CH$_2$)$_y$NR$^a$(CH$_2$)$_z$—), or an alkylbenzoalkyl linkage (—(CH$_2$)$_y$-1-benzo-2-(CH$_2$)$_z$—) form a ring with the carbon atom to which they are attached, wherein x=3 to 7, y=1 to 3, z=1 to 3, and R$^a$ is H, $(C_1-C_6)$alkyl, or phenyl; and R$^4$ is unsubstituted or substituted phenyl wherein the substituents are independently 1 to 5 H; halo; nitro; cyano; hydroxy; amino (—NR$^a$R$^b$); $(C_1-C_6)$alkyl; $(C_1-C_6)$haloalkyl; $(C_1-C_6)$cyanoalkyl; $(C_1-C_6)$hydroxyalkyl; $(C_1-C_6)$alkoxy; phenoxy; $(C_1-C_6)$haloalkoxy; $(C_1-C_6)$alkoxy$(C_1-C_6)$alkyl; $(C_1-C_6)$alkoxy$(C_1-C_6)$alkoxy; $(C_1-C_6)$alkanoyloxy$(C_1-C_6)$alkyl; $(C_2-C_6)$alkenyl optionally substituted with halo, cyano, $(C_1-C_4)$alkyl, or $(C_1-C_4)$alkoxy; $(C_2-C_6)$alkynyl optionally substituted with halo or $(C_1-C_4)$alkyl; formyl; carboxy; $(C_1-C_6)$alkylcarbonyl; $(C_1-C_6)$haloalkylcarbonyl; benzoyl; $(C_1-C_6)$alkoxycarbonyl; $(C_1-C_6)$haloalkoxycarbonyl; $(C_1-C_6)$alkanoyloxy (—OCOR$^a$); carboxamido (—CONR$^a$R$^b$); amido (—NR$^a$COR$^b$); alkoxycarbonylamino (—NR$^a$CO$_2$R$^b$); alkylaminocarbonylamino (—NR$^a$CONR R$^c$); mercapto; $(C_1-C_6)$alkylthio; $(C_1-C_6)$alkylsulfonyl; $(C_1-C_6)$alkylsulfoxido (—S(O)R$^a$); sulfamido (—SO$_2$NR$^a$R$^b$); or unsubstituted or substituted phenyl wherein the substituents are independently 1 to 3 halo, nitro, $(C_1-C_6)$alkoxy, $(C_1-C_6)$alkyl, or amino; or when two adjacent positions on the phenyl ring are substituted with alkoxy groups, these groups, together with the carbon atoms to which they are attached, may be joined to form a 5- or 6-membered dioxolano (—OCH$_2$O—) or dioxano (—OCH$_2$CH$_2$O—) heterocyclic ring; wherein R$^a$, R$^b$, and R$^c$ are independently H, (C$_1$-C$_6$) alkyl, or phenyl;

provided that R$^4$ is not 3-nitrophenyl or 4-nitrophenyl, and when R$^4$ is phenyl, then R$^1$ is not phenyl,
when R$^4$ is 3-chlorophenyl, then R$^1$ is not phenylamino, or
when R$^4$ is 4-chlorophenyl, then R$^1$ is not methyl.

2. The compound of claim 1 wherein:
X is O and X' is O or S;
R$^1$ is
   a) H, (C$_1$-C$_6$)alkyl, (C$_1$-C$_6$)haloalkyl, (C$_1$-C$_6$)cyanoalkyl, (C$_1$-C$_6$)alkoxycarbonyl(C$_1$-C$_6$)alkyl, (C$_1$-C$_6$)alkoxy, or benzyloxy;
   b) unsubstituted or substituted phenyl wherein the substituents are independently 1 to 5 H; halo; nitro; cyano; hydroxy; (C$_1$-C$_6$)alkyl; (C$_1$-C$_6$)haloalkyl; (C$_1$-C$_6$)cyanoalkyl; (C$_1$-C$_6$)hydroxyalkyl; (C$_1$-C$_6$)alkoxy; (C$_1$-C$_6$)haloalkoxy; (C$_1$-C$_6$)alkoxy(C$_1$-C$_6$)alkyl; (C$_1$-C$_6$)alkanoyloxy(C$_1$-C$_6$)alkyl; (C$_2$-C$_6$)alkenyl optionally substituted with halo, cyano, (C$_1$-C$_4$)alkyl, or (C$_1$-C$_4$)alkoxy; (C$_2$-C$_6$)alkynyl optionally substituted with halo or (C$_1$-C$_4$)alkyl; formyl; carboxy; (C$_1$-C$_6$)alkylcarbonyl; (C$_1$-C$_6$)haloalkylcarbonyl; benzoyl; (C$_1$-C$_6$)alkoxycarbonyl; (C$_1$-C$_6$)alkanoyloxy (—OCOR$^a$); carboxamido (—CONR$^a$R$^b$); amido (—NR$^a$COR$^b$); (C$_1$-C$_6$)alkylsulfonyl; (C$_1$-C$_6$)alkylsulfoxido (—S(O)R$^a$); sulfamido (—SO$_2$NR$^a$R$^b$); or unsubstituted or substituted phenyl wherein the substituents are independently 1 to 3 halo, nitro, (C$_1$-C$_6$)alkoxy, (C$_1$-C$_6$)alkyl, or amino; or when two adjacent positions on the phenyl ring are substituted with alkoxy groups, these groups, together with the carbon atoms to which they are attached, may be joined as a linkage (—OCH$_2$O—) or (—OCH$_2$CH$_2$O—) to form a 5- or 6-membered dioxolano or dioxano heterocyclic ring;
   c) unsubstituted or substituted benzothiophene-2-yl, or benzofuran-2-yl wherein the substituents are independently 1 to 3 halo, nitro, hydroxy, (C$_1$-C$_6$)alkyl, or (C$_1$-C$_6$)alkoxy;
   d) unsubstituted or substituted 2, 3, or 4-pyridyl wherein the substituents are independently 1 to 3 halo, cyano, nitro, hydroxy, (C$_1$-C$_6$)alkyl, (C$_1$-C$_6$)alkoxy, or (C$_1$-C$_6$) haloalkoxy;
   e) unsubstituted or substituted 5-membered heterocycle selected from furyl, thiophenyl, triazolyl, pyrazolyl, thiazolyl, isothiazolyl, oxazolyl, or isooxazolyl wherein the substituents are independently 1 to 3 halo, nitro, hydroxy, (C$_1$-C$_6$)alkyl, (C$_1$-C$_6$)alkoxy, carboxy, (C$_1$-C$_6$)alkoxycarbonyl (—CO$_2$R$^a$), or unsubstituted or substituted phenyl wherein the substituents are independently 1 to 3 halo, nitro, (C$_1$-C$_6$)alkyl, (C$_1$-C$_6$) haloalkyl, (C$_1$-C$_6$)alkoxy, (C$_1$-C$_6$)haloalkoxy, carboxy, or (C$_1$-C$_4$)alkoxycarbonyl (—CO$_2$R$^a$);
   f) aromatic-substituted or unsubstituted phenyl(C$_1$-C$_6$) alkyl, phenyl(C$_1$-C$_6$)alkoxy(C$_1$-C$_6$)alkyl, or phenoxy (C$_1$-C$_6$)alkyl wherein the aromatic substituents are independently 1 to 3 halo, nitro, (C$_1$-C$_6$) alkoxy, or (C$_1$-C$_6$)alkyl; or
   g) aromatic-substituted phenylamino, phenyl(C$_1$-C$_6$)alkylamino, or phenylcarbonylamino wherein the aromatic substituents are independently 1 to 3 halo, nitro, (C$_1$-C$_6$)alkoxy, or (C$_1$-C$_6$)alkyl;
wherein R$^a$ and R$^b$ are independently H, (C$_1$-C$_6$)alkyl, or phenyl;
R$^2$ and R$^3$ are independently H, (C$_1$-C$_6$)alkyl, (C$_1$-C$_6$)haloalkyl, (C$_1$-C$_6$)cyanoalkyl, (C$_1$-C$_6$)hydroxyalkyl, (C$_1$-C$_6$) alkoxy(C$_1$-C$_6$)alkyl, phenyl, or together as an alkane linkage (—(CH$_2$)$_x$—), an alkyloxylalkyl linkage (—(CH$_2$)$_y$O(CH$_2$)$_z$—), an alkylaminoalkyl linkage (—(CH$_2$)$_y$NR$^a$(CH$_2$)$_z$—), or an alkylbenzoalkyl linkage (—(CH$_2$)$_y$-1-benzo-2-(CH$_2$)$_z$—) form a ring with the carbon atom to which they are attached,
wherein x=3 to 7, y=1 to 3, z=1 to 3, and R$^a$ is H, (C$_1$-C$_6$)alkyl, or phenyl; and
R$^4$ is unsubstituted or substituted phenyl wherein the substituents are independently 1 to 5 H; halo; nitro; cyano; hydroxy; (C$_1$-C$_6$)alkyl; (C$_1$-C$_6$)haloalkyl; (C$_1$-C$_6$)cyanoalkyl; (C$_1$-C$_6$)hydroxyalkyl; (C$_1$-C$_6$)alkoxy; (C$_1$-C$_6$)haloalkoxy; (C$_1$-C$_6$)alkoxy(C$_1$-C$_6$)alkyl; (C$_1$-C$_6$)alkanoyloxy (C$_1$-C$_6$)alkyl; (C$_2$-C$_6$)alkenyl optionally substituted with halo, cyano, (C$_1$-C$_4$)alkyl, or (C$_1$-C$_4$)alkoxy; (C$_2$-C$_6$)alkynyl optionally substituted with halo or (C$_1$-C$_4$)alkyl; formyl; carboxy; (C$_1$-C$_6$)alkylcarbonyl; (C$_1$-C$_6$)haloalkylcarbonyl; benzoyl; (C$_1$-C$_6$)alkoxycarbonyl; (C$_1$-C$_6$)alkanoyloxy (—OCOR$^a$); carboxamido (—CONR$^a$R$^b$); amido (—NR$^a$COR$^b$); (C$_1$-C$_6$)alkylsulfonyl; (C$_1$-C$_6$)alkylsulfoxido (—S(O)R$^a$); sulfamido (—SO$_2$NR$^a$R$^b$); or unsubstituted or substituted phenyl wherein the substituents are independently 1 to 3 halo, nitro, (C$_1$-C$_6$)alkoxy, (C$_1$-C$_6$) alkyl, or amino; or when two adjacent positions on the phenyl ring are substituted with alkoxy groups, these groups, together with the carbon atoms to which they are attached, may be joined as a linkage (—OCH$_2$O—) or (—OCH$_2$CH$_2$O—) to form a 5- or 6-membered dioxolano or dioxano heterocyclic ring; wherein R$^a$ and R$^b$ are independently H, (C$_1$-C$_6$)alkyl, or phenyl;
provided that R$^4$ is not 3-nitrophenyl or 4-nitrophenyl, and when R$^4$ is phenyl, then R$^1$ is not phenyl,
when R$^4$ is 3-chlorophenyl, then R$^1$ is not phenylamino, or
when R$^4$ is 4-chlorophenyl, then R$^1$ is not methyl.

3. The compound of claim 2 wherein:
X is O;
X' is O or S;
R$^1$ is
   a) H, (C$_1$-C$_6$)alkyl, (C$_1$-C$_6$)haloalkyl, or (C$_1$-C$_6$)alkoxycarbonyl(C$_1$-C$_6$)alkyl;
   b) unsubstituted or substituted phenyl wherein the substituents are independently 1 to 5 H;
   halo; nitro; cyano; (C$_1$-C$_6$)alkyl; (C$_1$-C$_6$)haloalkyl; (C$_1$-C$_6$)alkoxy; (C$_1$-C$_6$)haloalkoxy; (C$_1$-C$_6$)alkylcarbonyl; (C$_1$-C$_6$)alkoxycarbonyl; carboxamido (—CONR$^a$R$^b$); amido (—NR$^a$COR$^b$); or phenyl; or when two adjacent positions on the phenyl ring are substituted with alkoxy groups, these groups, together with the carbon atoms to which they are attached, may be joined as a linkage (—OCH$_2$O—) or (—OCH$_2$CH$_2$O—) to form a 5- or 6-membered dioxolano or dioxano heterocyclic ring;
   c) unsubstituted or substituted benzothiophene-2-yl, or benzofuran-2-yl wherein the substituents are independently 1 to 3 halo, nitro, hydroxy, (C$_1$-C$_6$)alkyl, or (C$_1$-C$_6$)alkoxy;
   d) unsubstituted or substituted furyl or thiophenyl wherein the substituents are independently 1 to 3 halo, nitro, (C$_1$-C$_6$)alkyl, (C$_1$-C$_6$)alkoxy, carboxy, (C$_1$-C$_6$) alkoxycarbonyl (—CO$_2$R$^a$), or phenyl;
   e) aromatic-substituted or unsubstituted phenyl(C$_1$-C$_6$) alkyl, phenyl(C$_1$-C$_6$)alkoxy(C$_1$-C$_6$)alkyl, or phenoxy (C$_1$-C$_6$)alkyl wherein the aromatic substituents are independently 1 to 3 halo, nitro, (C$_1$-C$_6$) alkoxy, or (C$_1$-C$_6$)alkyl; or
   f) aromatic-substituted phenylamino, phenyl(C$_1$-C$_6$)alkylamino, or phenylcarbonylamino wherein the aromatic substituents are independently 1 to 3 halo, nitro, (C$_1$-C$_6$)alkoxy, or (C$_1$-C$_6$)alkyl;

wherein $R^a$ and $R^b$ are independently H, $(C_1\text{-}C_6)$alkyl, or phenyl;

$R^2$ and $R^3$ are independently H, $(C_1\text{-}C_6)$alkyl, $(C_1\text{-}C_6)$haloalkyl, $(C_1\text{-}C_6)$alkoxy$(C_1\text{-}C_6)$alkyl, phenyl, or together as an alkane linkage ($-(CH_2)_x-$), an alkyloxylalkyl linkage ($-(CH_2)_yO(CH_2)_z-$), an alkylaminoalkyl linkage ($-(CH_2)_yNR^a(CH_2)_z-$), or an alkylbenzoalkyl linkage ($-(CH_2)_y$-1-benzo-2-$(CH_2)_z-$) form a ring with the carbon atom to which they are attached, wherein x=3 to 7, y=1 to 3, z=1 to 3, and $R^a$ is H, $(C_1\text{-}C_6)$alkyl, or phenyl; and $R^4$ is unsubstituted or substituted phenyl wherein the substituents are independently 1 to 5 H; halo; nitro; cyano; $(C_1\text{-}C_6)$alkyl; $(C_1\text{-}C_6)$haloalkyl; $(C_1\text{-}C_6)$alkoxy; $(C_1\text{-}C_6)$haloalkoxy; $(C_1\text{-}C_6)$alkylcarbonyl; $(C_1\text{-}C_6)$alkoxycarbonyl; carboxamido ($-CONR^aR^b$); amido ($-NR^aCOR^b$); or phenyl; or when two adjacent positions on the phenyl ring are substituted with alkoxy groups, these groups, together with the carbon atoms to which they are attached, may be joined as a linkage ($-OCH_2O-$) or ($-OCH_2CH_2O-$) to form a 5- or 6-membered dioxolano or dioxano heterocyclic ring; wherein $R^a$ and $R^b$ are independently H, $(C_1\text{-}C_6)$alkyl, or phenyl;

provided that $R^4$ is not 3-nitrophenyl or 4-nitrophenyl, and when $R^4$ is phenyl, then $R^1$ is not phenyl, when $R^4$ is 3-chlorophenyl, then $R^1$ is not phenylamino, or when $R^4$ is 4-chlorophenyl, then $R^1$ is not methyl.

4. The compound of claim 3 wherein:

X and X' are O;

$R^1$ is phenyl, 4-chlorophenyl-, 4-ethylphenyl-, 2-ethyl-3,4-ethylenedioxyphenyl, 3-fluorophenyl-, 2-fluoro-4-ethylphenyl-, 2-methyl-3-methoxyphenyl-, 2-ethyl-3-methoxyphenyl, 3-methylphenyl-, 2-methoxyphenyl-, 2-nitrophenyl-, 3-nitrophenyl-, 2-furanyl-, benzyl-, benzothiophene-2-yl-, benzyloxymethyl, phenoxymethyl-, 3-toluoylamino-, benzylamino-, benzoylamino-, ethoxycarbonylethyl-, or 3-chloro-2,2,3,3-tetrafluoroethyl;

$R^2$ and $R^3$ are independently methyl, ethyl, or together as a tetramethylene ($-(CH2)_4-$), 4-pyrano ($-CH_2CH_2OCH_2CH_2-$), or methylenebenzoethylene ($-CH_2$-1-benzo-2-$CH_2CH_2-$) linkage form a ring with the carbon atom to which they are attached; and $R^4$ is phenyl, 4-biphenyl, 4-chlorophenyl, 2,4-dimethoxyphenyl, 3,5-dimethylphenyl, 2-methoxyphenyl, 3,4-methylenedioxyphenyl, 3-trifluoromethylphenyl, or 4-trifluromethoxyphenyl;

provided that when $R^4$ is phenyl, then $R^1$ is not phenyl.

5. The compound of claim 4 selected from the group consisting of:

1-Benzyl-3-[3-(3,5-dimethyl-phenyl)-5,5-dimethyl-[1,2,4]oxadiazol-4-yl]-urea;

1-Benzoyl-3-[3-(3,5-dimethyl-phenyl)-5,5-dimethyl-[1,2,4]oxadiazol-4-yl]-urea;

N-[3-(4-Chloro-phenyl)-5,5-dimethyl-[1,2,4]oxadiazol-4-yl]-4-ethyl-benzamide;

3-Chloro-N-[3-(4-chloro-phenyl)-5,5-dimethyl-[1,2,4]oxadiazol-4-yl]-2,2,3,3-tetrafluoro-propionamide;

N-[3-(4-Chloro-phenyl)-5,5-dimethyl-[1,2,4]oxadiazol-4-yl]-benzamide;

Benzo[b]thiophene-2-carboxylic acid[3-(4-chloro-phenyl)-5,5-dimethyl-[1,2,4]oxadiazol-4-yl]-amide;

N-[3-(4-Chloro-phenyl)-5,5-dimethyl-[1,2,4]oxadiazol-4-yl]-succinamic acid ethyl ester;

N-[3-(4-Chloro-phenyl)-5,5-dimethyl-[1,2,4]oxadiazol-4-yl]-2-phenoxy-acetamide;

2-Benzyloxy-N-[3-(4-chloro-phenyl)-5,5-dimethyl-[1,2,4]oxadiazol-4-yl]-acetamide;

Furan-2-carboxylic acid[3-(4-chloro-phenyl)-5,5-dimethyl-[1,2,4]oxadiazol-4-yl]-amide;

N-[3-(4-Chloro-phenyl)-5,5-dimethyl-[1,2,4]oxadiazol-4-yl]-2-phenyl-acetamide;

N-[3-(4-Chloro-phenyl)-5,5-dimethyl-[1,2,4]oxadiazol-4-yl]-2-ethyl-3-methoxy-benzamide;

N-[5,5-Dimethyl-3-(4-trifluoromethoxy-phenyl)-[1,2,4]oxadiazol-4-yl]-benzamide;

N-[5,5-Dimethyl-3-(4-trifluoromethoxy-phenyl)-[1,2,4]oxadiazol-4-yl]-4-ethyl-benzamide;

Benzo[b]thiophene-2-carboxylic acid[5,5-dimethyl-3-(4-trifluoromethoxy-phenyl)-[1,2,4]oxadiazol-4-yl]-amide;

N-[5,5-Dimethyl-3-(4-trifluoromethoxy-phenyl)-[1,2,4]oxadiazol-4-yl]-2-phenoxy-acetamide;

2-Benzyloxy-N-[5,5-dimethyl-3-(4-trifluoromethoxy-phenyl)-[1,2,4]oxadiazol-4-yl]-acetamide;

N-[5,5-Dimethyl-3-(4-trifluoromethoxy-phenyl)-[1,2,4]oxadiazol-4-yl]-2-phenyl-acetamide;

Furan-2-carboxylic acid[5,5-dimethyl-3-(4-trifluoromethoxy-phenyl)-[1,2,4]oxadiazol-4-yl]-amide;

N-[5,5-Dimethyl-3-(4-trifluoromethoxy-phenyl)-[1,2,4]oxadiazol-4-yl]-2-ethyl-3-methoxy-benzamide;

N-[5,5-Dimethyl-3-(3-trifluoromethyl-phenyl)-[1,2,4]oxadiazol-4-yl]-4-ethyl-benzamide;

N-[5,5-Dimethyl-3-(3-trifluoromethyl-phenyl)-[1,2,4]oxadiazol-4-yl]-benzamide;

3-Chloro-N-[5,5-dimethyl-3-(3-trifluoromethyl-phenyl)-[1,2,4]oxadiazol-4-yl]-2,2,3,3-tetrafluoro-propionamide;

N-[5,5-Dimethyl-3-(3-trifluoromethyl-phenyl)-[1,2,4]oxadiazol-4-yl]-succinamic acid ethyl ester;

2-Benzyloxy-N-[5,5-dimethyl-3-(3-trifluoromethyl-phenyl)-[1,2,4]oxadiazol-4-yl]-acetamide;

Furan-2-carboxylic acid[5,5-dimethyl-3-(3-trifluoromethyl-phenyl)-[1,2,4]oxadiazol-4-yl]-amide;

4-Ethyl-N-[3-(2-methoxy-phenyl)-5,5-dimethyl-[1,2,4]oxadiazol-4-yl]-benzamide;

N-[3-(2-Methoxy-phenyl)-5,5-dimethyl-[1,2,4]oxadiazol-4-yl]-benzamide;

N-[5,5-Dimethyl-3-(3-trifluoromethyl-phenyl)-[1,2,4]oxadiazol-4-yl]-2-ethyl-3-methoxy-benzamide;

N-[5,5-Dimethyl-3-(3-trifluoromethyl-phenyl)-[1,2,4]oxadiazol-4-yl]-2-phenyl-acetamide;

N-[5,5-Dimethyl-3-(3-trifluoromethyl-phenyl)-[1,2,4]oxadiazol-4-yl]-2-phenoxy-acetamide;

Benzo[b]thiophene-2-carboxylic acid[5,5-dimethyl-3-(3-trifluoromethyl-phenyl)-[1,2,4]oxadiazol-4-yl]-amide;

3-Chloro-2,2,3,3-tetrafluoro-N-[3-(2-methoxy-phenyl)-5,5-dimethyl-[1,2,4]oxadiazol-4-yl]-propionamide;

N-[3-(2-Methoxy-phenyl)-5,5-dimethyl-[1,2,4]oxadiazol-4-yl]-succinamic acid ethyl ester;

Benzo[b]thiophene-2-carboxylic acid[3-(2-methoxy-phenyl)-5,5-dimethyl-[1,2,4]oxadiazol-4-yl]-amide;

N-[3-(2-Methoxy-phenyl)-5,5-dimethyl-[1,2,4]oxadiazol-4-yl]-2-phenoxy-acetamide;

2-Benzyloxy-N-[3-(2-methoxy-phenyl)-5,5-dimethyl-[1,2,4]oxadiazol-4-yl]-acetamide;

N-[3-(2-Methoxy-phenyl)-5,5-dimethyl-[1,2,4]oxadiazol-4-yl]-2-phenyl-acetamide;

Furan-2-carboxylic acid[3-(2-methoxy-phenyl)-5,5-dimethyl-[1,2,4]oxadiazol-4-yl]-amide;

2-Ethyl-3-methoxy-N-[3-(2-methoxy-phenyl)-5,5-dimethyl-[1,2,4]oxadiazol-4-yl]-benzamide;

N-(3-Benzo[1,3]dioxol-5-yl-5,5-dimethyl-[1,2,4]oxadiazol-4-yl)-4-ethyl-benzamide;
N-(3-Benzo[1,3]dioxol-5-yl-5,5-dimethyl-[1,2,4]oxadiazol-4-yl)-benzamide;
N-(3-Benzo[1,3]dioxol-5-yl-5,5-dimethyl-[1,2,4]oxadiazol-4-yl)-succinamic acid ethyl ester;
Benzo[b]thiophene-2-carboxylic acid (3-benzo[1,3]dioxol-5-yl-5,5-dimethyl-[1,2,4]oxadiazol-4-yl)-amide;
N-(3-Benzo[1,3]dioxol-5-yl-5,5-dimethyl-[1,2,4]oxadiazol-4-yl)-2-phenoxy-acetamide;
N-(3-Benzo[1,3]dioxol-5-yl-5,5-dimethyl-[1,2,4]oxadiazol-4-yl)-2-benzyloxy-acetamide;
N-(3-Benzo[1,3]dioxol-5-yl-5,5-dimethyl-[1,2,4]oxadiazol-4-yl)-2-phenyl-acetamide;
Furan-2-carboxylic acid (3-benzo[1,3]dioxol-5-yl-5,5-dimethyl-[1,2,4]oxadiazol-4-yl)-amide;
N-(3-Benzo[1,3]dioxol-5-yl-5,5-dimethyl-[1,2,4]oxadiazol-4-yl)-2-ethyl-3-methoxy-benzamide;
N-[3-(2,4-Dimethoxy-phenyl)-5,5-dimethyl-[1,2,4]oxadiazol-4-yl]-4-ethyl-benzamide;
N-[3-(2,4-Dimethoxy-phenyl)-5,5-dimethyl-[1,2,4]oxadiazol-4-yl]-benzamide;
N-[3-(2,4-Dimethoxy-phenyl)-5,5-dimethyl-[1,2,4]oxadiazol-4-yl]-succinamic acid ethyl ester;
Benzo[b]thiophene-2-carboxylic acid[3-(2,4-dimethoxy-phenyl)-5,5-dimethyl-[1,2,4]oxadiazol-4-yl]-amide;
N-[3-(2,4-Dimethoxy-phenyl)-5,5-dimethyl-[1,2,4]oxadiazol-4-yl]-2-phenoxy-acetamide;
2-Benzyloxy-N-[3-(2,4-dimethoxy-phenyl)-5,5-dimethyl-[1,2,4]oxadiazol-4-yl]-acetamide;
N-[3-(2,4-Dimethoxy-phenyl)-5,5-dimethyl-[1,2,4]oxadiazol-4-yl]-2-phenyl-acetamide;
Furan-2-carboxylic acid[3-(2,4-dimethoxy-phenyl)-5,5-dimethyl-[1,2,4]oxadiazol-4-yl]-amide;
N-[3-(2,4-Dimethoxy-phenyl)-5,5-dimethyl-[1,2,4]oxadiazol-4-yl]-2-ethyl-3-methoxy-benzamide;
N-(3-Biphenyl-4-yl-5,5-dimethyl-[1,2,4]oxadiazol-4-yl)-4-ethyl-benzamide;
N-(3-Biphenyl-4-yl-5,5-dimethyl-[1,2,4]oxadiazol-4-yl)-2-ethyl-3-methoxy-benzamide;
4-Ethyl-N-(5-ethyl-5-methyl-3-phenyl-[1,2,4]oxadiazol-4-yl)-benzamide;
N-(5-Ethyl-5-methyl-3-phenyl-[1,2,4]oxadiazol-4-yl)-benzamide;
Benzo[b]thiophene-2-carboxylic acid (5-ethyl-5-methyl-3-phenyl-[1,2,4]oxadiazol-4-yl)-amide;
N-(5-Ethyl-5-methyl-3-phenyl-[1,2,4]oxadiazol-4-yl)-2-phenoxy-acetamide;
2-Benzyloxy-N-(5-ethyl-5-methyl-3-phenyl-[1,2,4]oxadiazol-4-yl)-acetamide;
N-(5-Ethyl-5-methyl-3-phenyl-[1,2,4]oxadiazol-4-yl)-2-phenyl-acetamide;
Furan-2-carboxylic acid (5-ethyl-5-methyl-3-phenyl-[1,2,4]oxadiazol-4-yl)-amide;
2-Ethyl-N-(5-ethyl-5-methyl-3-phenyl-[1,2,4]oxadiazol-4-yl)-3-methoxy-benzamide;
N-[3-(3,5-Dimethyl-phenyl)-5-ethyl-5-methyl-[1,2,4]oxadiazol-4-yl]-4-ethyl-benzamide;
N-[3-(3,5-Dimethyl-phenyl)-5-ethyl-5-methyl-[1,2,4]oxadiazol-4-yl]-benzamide;
3-Chloro-N-[3-(3,5-dimethyl-phenyl)-5-ethyl-5-methyl-[1,2,4]oxadiazol-4-yl]-2,2,3,3-tetrafluoro-propionamide;
N-[3-(3,5-Dimethyl-phenyl)-5-ethyl-5-methyl-[1,2,4]oxadiazol-4-yl]-succinamic acid ethyl ester;
Benzo[b]thiophene-2-carboxylic acid[3-(3,5-dimethyl-phenyl)-5-ethyl-5-methyl-[1,2,4]oxadiazol-4-yl]-amide;
N-[3-(3,5-Dimethyl-phenyl)-5-ethyl-5-methyl-[1,2,4]oxadiazol-4-yl]-2-phenoxy-acetamide;
2-Benzyloxy-N-[3-(3,5-dimethyl-phenyl)-5-ethyl-5-methyl-[1,2,4]oxadiazol-4-yl]-acetamide;
N-[3-(3,5-Dimethyl-phenyl)-5-ethyl-5-methyl-[1,2,4]oxadiazol-4-yl]-2-phenyl-acetamide;
Furan-2-carboxylic acid[3-(3,5-dimethyl-phenyl)-5-ethyl-5-methyl-[1,2,4]oxadiazol-4-yl]-amide;
N-[3-(3,5-Dimethyl-phenyl)-5-ethyl-5-methyl-[1,2,4]oxadiazol-4-yl]-2-ethyl-3-methoxy-benzamide;
4-Ethyl-N-(3-phenyl-1-oxa-2,4-diaza-spiro[4.4]non-2-en-4-yl)-benzamide;
N-(3-Phenyl-1-oxa-2,4-diaza-spiro[4.4]non-2-en-4-yl)-benzamide;
3-Chloro-2,2,3,3-tetrafluoro-N-(3-phenyl-1-oxa-2,4-diaza-spiro[4.4]non-2-en-4-yl)-propionamide;
N-(3-Phenyl-1-oxa-2,4-diaza-spiro[4.4]non-2-en-4-yl)-succinamic acid ethyl ester;
Benzo[b]thiophene-2-carboxylic acid (3-phenyl-1-oxa-2,4-diaza-spiro[4.4]non-2-en-4-yl)-amide;
2-Phenoxy-N-(3-phenyl-1-oxa-2,4-diaza-spiro[4.4]non-2-en-4-yl)-acetamide;
2-Benzyloxy-N-(3-phenyl-1-oxa-2,4-diaza-spiro[4.4]non-2-en-4-yl)-acetamide;
2-Phenyl-N-(3-phenyl-1-oxa-2,4-diaza-spiro[4.4]non-2-en-4-yl)-acetamide;
Furan-2-carboxylic acid (3-phenyl-1-oxa-2,4-diaza-spiro[4.4]non-2-en-4-yl)-amide;
2-Ethyl-3-methoxy-N-(3-phenyl-1-oxa-2,4-diaza-spiro[4.4]non-2-en-4-yl)-benzamide;
N-[3-(3,5-Dimethyl-phenyl)-1-oxa-2,4-diaza-spiro[4.4]non-2-en-4-yl]-4-ethyl-benzamide;
N-[3-(3,5-Dimethyl-phenyl)-1-oxa-2,4-diaza-spiro[4.4]non-2-en-4-yl]-benzamide;
3-Chloro-N-[3-(3,5-dimethyl-phenyl)-1-oxa-2,4-diaza-spiro[4.4]non-2-en-4-yl]-2,2,3,3-tetrafluoro-propionamide;
N-[3-(3,5-Dimethyl-phenyl)-1-oxa-2,4-diaza-spiro[4.4]non-2-en-4-yl]-succinamic acid ethyl ester;
Benzo[b]thiophene-2-carboxylic acid[3-(3,5-dimethyl-phenyl)-1-oxa-2,4-diaza-spiro[4.4]non-2-en-4-yl]-amide;
N-[3-(3,5-Dimethyl-phenyl)-1-oxa-2,4-diaza-spiro[4.4]non-2-en-4-yl]-2-phenoxy-acetamide;
2-Benzyloxy-N-[3-(3,5-dimethyl-phenyl)-1-oxa-2,4-diaza-spiro[4.4]non-2-en-4-yl]-acetamide;
N-[3-(3,5-Dimethyl-phenyl)-1-oxa-2,4-diaza-spiro[4.4]non-2-en-4-yl]-2-phenyl-acetamide;
Furan-2-carboxylic acid[3-(3,5-dimethyl-phenyl)-1-oxa-2,4-diaza-spiro[4.4]non-2-en-4-yl]-amide;
N-[3-(3,5-Dimethyl-phenyl)-1-oxa-2,4-diaza-spiro[4.4]non-2-en-4-yl]-2-ethyl-3-methoxy-benzamide;
4-Ethyl-N-(3-phenyl-1,8-dioxa-2,4-diaza-spiro[4.5]dec-2-en-4-yl)-benzamide;
N-(3-Phenyl-1,8-dioxa-2,4-diaza-spiro[4.5]dec-2-en-4-yl)-benzamide;
2-Phenoxy-N-(3-phenyl-1,8-dioxa-2,4-diaza-spiro[4.5]dec-2-en-4-yl)-acetamide;
2-Benzyloxy-N-(3-phenyl-1,8-dioxa-2,4-diaza-spiro[4.5]dec-2-en-4-yl)-acetamide;
2-Phenyl-N-(3-phenyl-1,8-dioxa-2,4-diaza-spiro[4.5]dec-2-en-4-yl)-acetamide;
2-Ethyl-3-methoxy-N-(3-phenyl-1,8-dioxa-2,4-diaza-spiro[4.5]dec-2-en-4-yl)-benzamide;

N-[3-(3,5-Dimethyl-phenyl)-1,8-dioxa-2,4-diaza-spiro[4.5]dec-2-en-4-yl]-4-ethyl-benzamide;
N-[3-(3,5-Dimethyl-phenyl)-1,8-dioxa-2,4-diaza-spiro[4.5]dec-2-en-4-yl]-benzamide;
N-[3-(3,5-Dimethyl-phenyl)-1,8-dioxa-2,4-diaza-spiro[4.5]dec-2-en-4-yl]-2-phenoxy-acetamide;
2-Benzyloxy-N-[3-(3,5-dimethyl-phenyl)-1,8-dioxa-2,4-diaza-spiro[4.5]dec-2-en-4-yl]-acetamide;
N-[3-(3,5-Dimethyl-phenyl)-1,8-dioxa-2,4-diaza-spiro[4.5]dec-2-en-4-yl]-2-phenyl-acetamide;
Furan-2-carboxylic acid[3-(3,5-dimethyl-phenyl)-1,8-dioxa-2,4-diaza-spiro[4.5]dec-2-en-4-yl]-amide;
N-[3-(3,5-Dimethyl-phenyl)-1,8-dioxa-2,4-diaza-spiro[4.5]dec-2-en-4-yl]-2-ethyl-3-methoxy-benzamide;
N-[3-(3,5-Dimethyl-phenyl)-1-oxa-2,4-diaza-spiro[4.5]-7,8-benzo-dec-2-en-4-yl]-3-methoxy-2-methyl-benzamide;
N-[3-(3,5-Dimethyl-phenyl)-1,8-dioxa-2,4-diaza-spiro[4.5]dec-2-en-4-yl]-3-methoxy-2-methyl-benzamide;
N-[3-(3,5-Dimethyl-phenyl)-5,5-dimethyl-[1,2,4]oxadiazol-4-yl]-3-methoxy-2-methyl-benzamide;
N-[3-(3,5-Dimethyl-phenyl)-5-ethyl-5-methyl-[1,2,4]oxadiazol-4-yl]-4-ethyl-2-fluoro-benzamide;
4-Ethyl-2-fluoro-N-(3-phenyl-1-oxa-2,4-diaza-spiro[4.4]non-2-en-4-yl)-benzamide;
N-[3-(3,5-Dimethyl-phenyl)-1-oxa-2,4-diaza-spiro[4.4]non-2-en-4-yl]-4-ethyl-2-fluoro-benzamide;
N-(5,5-Dimethyl-3-phenyl-[1,2,4]oxadiazol-4-yl)-4-ethyl-2-fluoro-benzamide;
5-Ethyl-2,3-dihydro-benzo[1,4]dioxine-6-carboxylic acid (5,5-dimethyl-3-phenyl-[1,2,4]oxadiazol-4-yl)-amide; and
5-Ethyl-2,3-dihydro-benzo[1,4]dioxine-6-carboxylic acid [3-(3,5-dimethyl-phenyl)-5-ethyl-5-methyl-[1,2,4]oxadiazol-4-yl]-amide.

* * * * *